United States Patent [19]

Satow et al.

[11] Patent Number: 5,039,331

[45] Date of Patent: Aug. 13, 1991

[54] CONDENSED HETEROCYCLIC DERIVATIVES AND HERBICIDES

[75] Inventors: Jun Satow; Kenzou Fukuda; Kaoru Itoh, all of Funabashi; Takashi Ikai, Tokyo; Koichi Suzuki, Shiraoka; Tsutomu Nawamaki, Shiraoka; Shigeomi Watanabe, Shiraoka, all of Japan

[73] Assignee: Nissan Chemical Industries, Ltd., Tokyo, Japan

[21] Appl. No.: 236,741

[22] Filed: Aug. 26, 1988

[30] Foreign Application Priority Data

Aug. 28, 1987 [JP] Japan .................. 62-214744
Nov. 27, 1987 [JP] Japan .................. 62-299549
Jun. 22, 1988 [JP] Japan .................. 63-154328

[51] Int. Cl.$^5$ .................. A01N 43/38; C07D 513/04
[52] U.S. Cl. .................. 71/90; 544/58.2; 544/105; 544/235
[58] Field of Search .............. 544/58.2, 105, 235; 71/90

[56] References Cited

U.S. PATENT DOCUMENTS 4,816,063  3/1989  Yamaguchi et al. .................. 71/90

FOREIGN PATENT DOCUMENTS 0273417  7/1988  European Pat. Off. .

OTHER PUBLICATIONS

Patent Abstracts of Japan, vol. 11, No. 167 (C-425) [2614], 28th May 1987; & JP-A-62 00 091 (Kumiai Chem. Ind.) 06-01-1987.

Primary Examiner—Richard L. Raymond
Attorney, Agent, or Firm—Oblon, Spivak, McClelland, Maier & Neustadt

[57] ABSTRACT

A condensed heterocyclic derivative having the formula:

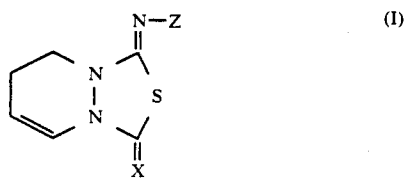

wherein X is an oxygen atom or a sulfur atom; and Z is

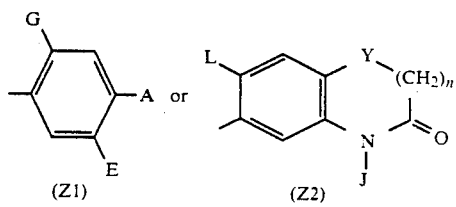

19 Claims, No Drawings

CONDENSED HETEROCYCLIC DERIVATIVES AND HERBICIDES

The present invention relates to novel condensed heterocyclic derivatives, a process for their production and selective herbicides containing such derivatives as active ingredients, which are useful particularly as herbicides for paddy field and upland field.

Heretofore, a number of herbicides have been practically used to protect important crop plants such as rice, soybean, peanut, sunflower, sorgo, wheat, corn, cotton and sugar beet from weeds and to increase the productivity of such important crop plants. In recent years, with a worldwide increase of population, it is evident that the productivity of such important crop plants gives a direct influence over the food economy of the world. From this viewpoint, it is increasingly important for those concerned with agriculture to develop herbicides which are capable of efficiently controlling weeds which hinder the cultivation of such important crop plants.

As such herbicides, it is desired to develop active agents which satisfy the following conditions.

They should have proper residual activities. (In recent years, there has been a problem that active agents having long residual life in soil give damages to the subsequently cultivated plants, and it is important that the residual activities after application should be proper). After the application, they should quickly kill weeds. (It is especially effective to control concurrently germinating weeds at the initial growing stage of crop plants to improve the subsequent growing conditions of the crop plants). The number of applications should be small. (This is important also with a view to saving the labor for the weed controlling operation.) In a cultivated field where crop plants and weeds are concurrently present, they should selectively kill only the weeds by the simultaneous foilage treatment of both the crop plants and the weeds. (Reflecting the trend for non-plowing cultivation, there is an increasing trend for foilage treatment during the growing stage rather than the conventional soil incorporation.) They should not adversely affect the crop yield. (It is important that they do not create an adverse effect to the yield such as the growth control, at the time of the herversting.) They should be effective against perennial weeds. (Major weeds of the world include many perennial weeds.) They should have high herbicidal effects at a low dose. (Especially from the viewpoint of the environmental protection, it is desired to kill weeds at a low dose of the active agent.)

However, conventional herbicides do not necessarily satisfy all of the above conditions.

On the other hand, it is already known that certain condensed heterocyclic compounds exhibit herbicidal activities. For example, in the Pesticide Manual, 8th edition, p 670, by The British Crop Protection Council (1987), Benazolin is disclosed as a herbicide having a condensed heterocyclic structure. However, such a compound is inadequate in the herbicidal effects or plant selectivity and can not necessarily be regarded as being suitable as a herbicide for paddy field or upland field.

Further, Japanese Unexamined Patent Publication No. 91/1987 disclosed a compound having the following formula:

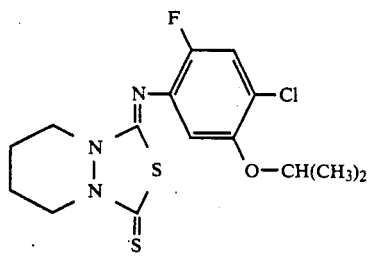

Such a compound exhibits herbicidal effects even at a low dose. However, the selectivity range between crop plants and weeds in the foilage treatment is narrow, and it is inadequate as a herbicide for upland field.

Under these circumstances, the present inventors have conducted extensive research to develop a herbicide having selectivity for important crop plants and showing excellent herbicidal effects at a low dose. As a result, they have found that condensed heterocyclic derivatives of the formula I given below (hereinafter referred to as the compounds of the present invention) exhibit high herbicidal activities as upland herbicides in both soil and foilage treatments against broad-leaved weeds including Solanaceae weeds such as *Solanum nigrum* and *Datura stramonium*, Malvaceae weeds such as *Abutilon theophrasti* or *Sida spinosa*, Convolvulaceae weeds such as *Ipomoea* spps. including *Ipomoea purpurea*, or *Calystegia* spps., Amaranthaceae weeds such as *Amaranthus lividus* or *Amaranthus retroflexus*, Compositae weeds such as *Xanthium pensylvanicum*, *Ambrosia artemisiaefolia*, *Helianthus annus*, *Galinsoga ciliata*, *Cirsium arvense*, *Senecio vulgaris* or *Erigeron annus*, Cruciferae weeds such as *Rorippa indicia*, *Sinapis arevnsis* or Capsella Bursapastoris, Polygonaceae weeds such as *Polygonum Blumei* or *Polygonum convolvulus*, Portulacaceae weeds such as *Portulaca oleracea*, Chenopodiaceae weeds such as *Chenopodium album*, *Chenopodium ficifolium* or *Kochia scoparia*, Caryophyllaceae weeds such as *Stellaria media*, Scrophulariaceae weeds such as *Veronica persica*, Commelinaceae weeds such as *Commelina communis*, Labiatae weeds such as *Lamium amplexicaule* or *Lamium purpureum*, Euphorbiaceae weeds such as *Euphorbia supina* or *Euphorbia maculata*, Rubiaceae weeds such as *Galium spurium* or *Rubia akane*, Violaceae weeds such as *Viola mandshurica*, Leguminosae weeds such as *Sesbania exaltata* or *Cassia obtusifolia* and against various upland weeds including graminaceous weeds such as *Sorgham bicolor*, *Panicum dichotomiflorum*, *Sorghum halepense*, *Echinochloa crus-galli*, *Digitaria adscendens*, *Avena fatua*, *Eleusine indicia*, *Setaria viridis* or *Alopecurus aegualis*, and Cyperaceous weeds such as *Cyperus rotundus* or *Cyperus esculentus*, and they also exhibit high herbicidal activities as paddy field herbicides at a low dose in both irrigated soil treatment and foilage treatment against paddy weeds including Alismataceae weeds such as *Alisma canaliculatum*, *Sagittaria trifolia* or *Sagittaria pygmaea*, Cyperaceae weeds such as *Cyperus difformis*, *Cyperus serotinus*, *Scirpus juncoides* or *Eleocharic kuroguwai*, Scrothulariaceae weeds such as *Lindemia pyxidaria*, Potenderiaceae weeds such as *Monochoria vaginalis*, Potamogetonaceae weeds such as *Potamogeton distinctus*, Lythraceae weeds such as *Rotala indica*, and Gramineae weeds such as *Echinochloa crus-galli*. Further, it has been found that the compounds of the present invention are highly safe against important crop plants such as rice, wheat, barely, sorgo, peanut, corn, soybean, cotton and sugar beet.

The present invention has been accomplished on the basis of these discoveries.

The present invention provides a condensed heterocyclic derivative having the formula:

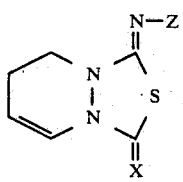
(I)

wherein X is an oxygen atom or a sulfur atom; and Z is

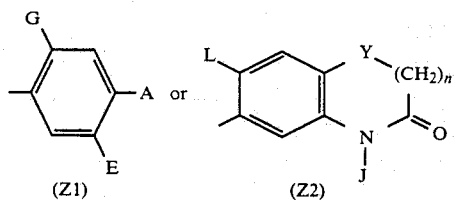

wherein G is a hydrogen atom or a halogen atom; A is a halogen atom or $NO_2$; E is a hydrogen atom, a halogen atom, $C\equiv N$, $NO_2$, $NH_2$, OH, SH, $OR_1$ (wherein $R_1$ is $C_1-C_5$ alkyl, $C_3-C_6$ cycloalkyl, $C_3-C_6$ cycloalkyl $(C_1-C_2)$ alkyl, $C_2-C_4$ alkenyl, $C_3-C_4$ alkynyl,

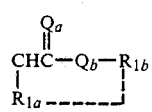

wherein each of Qa and Qb is an oxygen atom or a sulfur atom, $R_{1a}$ is a hydrogen atom or $C_{1-C3}$ alkyl, $R_{1b}$ is a hydrogen atom, $C_1-C_5$ alkyl, $C_2-C_5$ alkenyl, $C_3-C_5$ alkynyl, $C_2-C_3$ haloalkyl, $C_1-C_2$ alkoxy $(C_1-C_2)$ alkyl, $C_3-C_6$ cycloalkyl $(C_1-C_2)$ alkyl, $C_3-C_6$ cycloalkyl, $CH_2CO_2-(C_1-C_3$ alkyl) or $CH(CH_3)—CO_2—(C_1-C_2$ alkyl), or $R_{1a}$ and $R_{1b}$ together form an alkylene group which in turn forms, together with

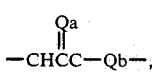

a 4–6 membered lactone ring,

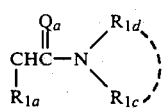

wherein $R_{1a}$ and Qa are defined above, each of $R_{1c}$ and $R_{1d}$ is a hydrogen atom, $C_1-C_5$ alkyl, $C_2-C_5$ alkenyl, $C_3-C_5$ alkynyl, $C_2-C_5$ haloalkyl, $C_3-C_6$ cycloalkyl or $C_3-C_6$ cycloalkyl $(C_1-C_2)$ alkyl, or $R_{1d}$ and $R_{1c}$ together form an alkylene group which in turn forms, together with the adjacent nitrogen atom, a 5–7 membered ring, $CH_2C\equiv N$, tetrahydropyranyl, tetrahydrothiopyranyl, $CH_2COR_{1e}$,

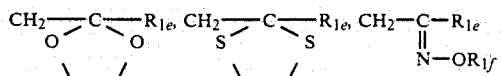

wherein $R_{1e}$ is $C_1-C_3$ alkyl, $R_{1f}$ is a hydrogen atom, $C_1-C_3$ alkyl, $CH_2CO_2—(C_1-C_3$ alkyl) or $COCH_3$, or $C_1-C_2$ alkoxy $(C_1-C_2)$ alkyl), $SR_3$ (wherein $R_3$ has the same meaning as $R_1$ defined above), $CO_2R_5$ (wherein $R_5$ is a hydrogen atom, $C_1-C_5$ alkyl, $C_3-C_6$ cycloalkyl or $C_3-C_6$ cycloalkyl $(C_1-C_2)$ alkyl). $NHR_6$ (wherein $R_6$ is $C_1-C_5$ alkyl, $C_3-C_6$ cycloalkyl, $C_3-C_6$ cycloalkyl $(C_1-C_2)$ alkyl, $C_2-C_4$ alkenyl or $C_3-C_4$ alkynyl) or $CH=NOR_7$ (wherein $R_7$ is a hydrogen atom, $C_1-C_5$ alkyl, $C_3-C_6$ cycloalkyl, $C_3-C_6$ cycloalkyl $(C_1-C_2)$ alkyl, $C_2-C_4$ alkenyl or $C_3-C_4$ alkynyl); L is a hydrogen atom or a halogen atom; Y is an oxygen atom or a sulfur atom; n is an integer of 0 or 1; J is a hydrogen atom, a halogen atom, $C_1-C_5$ alkyl, $C_3-C_6$ cycloalkyl, $C_3-C_6$ cycloalkyl $(C_1-C_2)$ alkyl, $C_2-C_4$ alkenyl, $C_3-C_4$ alkynyl, $C_1-C_5$ haloalkyl, $C_3-C_4$ haloalkenyl, $C_3-C_4$ haloalkynyl, $C_1-C_2$ alkoxy $(C_1-C_2)$ alkyl, $CH_2C\equiv N$, $CH_2CO_2R_8$ (wherein $R_8$ is a hydrogen atom, $C_1-C_5$ alkyl, $C_3-C_6$ cycloalkyl or $C_3-C_6$ cycloalkyl $C_1-C_2$) alkyl), or $CH_2CH_2CO_2R_9$ (wherein $R_9$ is a hydrogen atom $C_1-C_5$ alkyl, $C_3-C_6$ cycloalkyl or $C_3-C_6$ cycloalkyl $(C_1-C_2)$ alkyl).

The present invention also provides a process for producing the condensed heterocyclic derivative of the formula I which comprises reacting a thiosemicarbazone derivative of the formula:

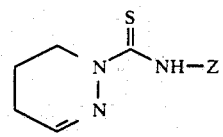
(II)

wherein Z is as defined in claim 1, with a compound of the formula:

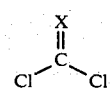
(III)

wherein X is as defined in claim 1.

Further, the present invention provides a herbicide which comprises a herbicidally effective amount of the condensed heterocyclic derivative of the formula I and an agricultural carrier or diluent.

It is a feature of the present invention that the compounds of the present invention include those having a wide range of selectivity in the foilage treatment of the crop plants and weeds, particularly in the selectivity between soybean and weeds, or peanut and weeds, as compared with the conventional compounds, and they have highly safe against such crop plants.

Further, among these compounds, some exhibit high safety against corn, or some exhibits high safety against rice.

On the other hand, the compounds of the present invention exhibit high herbicidal effects promptly at a low dose as compared with the conventional herbicides. Therefore, some of the compounds are useful also as herbicides for orchards, grasslands, lawns or non-agricultural fields.

The compounds of the present invention represented by the formula I are novel compounds.

Heretofore, Hans Kefer, disclosed in Synthesis, 81 (1972) that in the synthesis of an N-acyllactam, an enamide is obtainable by acylation in the presence of a base:

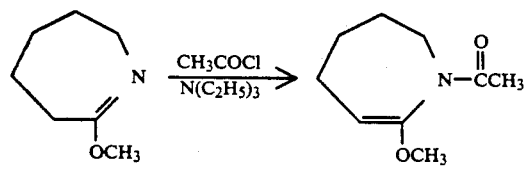

Further, Wolfgang Oppolzer, et al. disclose in Tetrahedron Letters, 981, (1979), a process for synthesizing a dienamide by acylating an imine derivative:

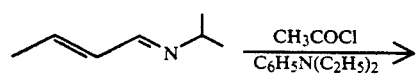

However, as in the case of the compounds of the present invention, a process for cyclizing and synthesizing an enamide structure by acylating a thiosemicarbazone derivative i.e. a novel compound of the formula II, has not been known and is a novel process.

Now, the process for the production of the compounds of the present invention will be described in detail.

The compound of the present invention represented by the formula I can readily be prepared by reacting a thiosemicarbazone derivative of the formula II with from 1.0 to 2.0 equivalent of a compound of the formula III in a solvent in the presence of from 2.0 to 4.0 equivalent of a base at a temperature of from 0° to 200° C., for example, at 20° C. or at a reflux temperature for from 30 minutes to 48 hours.

The solvent may be an aliphatic hydrocarbon such as hexane, heptane, ligroin or petroleum ether, an aromatic hydrocarbon such as benzene, toluene or xylene, a halogenated hydrocarbon such as chloroform, methylene chloride or chlorobenzene, an ether such as diethyl ether, dioxane, ethylene glycol dimethyl ether or THF, a ketone such as acetone or methyl ethyl ketone, a nitrile such as acetonitrile or isobutyronitrile, a tertiary amine such as pyridine or N,N-diethylaniline, an acid amide such as formamide or N,N-dimethylformamide, a sulfur compound such as dimethyl sulfoxide or sulforane, or a mixture thereof.

The base may be an organic base such as pyridine, triethylamine, 1,4-diazabicycle[2.2.2]octane or N,N-diethylaniline, or an inorganic base such as sodium hydroxide, potassium hydroxide, sodium carbonate, potassium carbonate or sodium hydride.

When the compound of the formula III is phosgene i.e. X in the formula III being an oxygen atom, phosgene per ce may be used for the reaction. However, a so-called phosgene dimer i.e. $ClCO_2CCl_3$ (trichloromethyl chloroformate) may be used so that it acts as phosgene in the reaction system.

After completion of the reaction, the solvent is distilled off to some extent, and then the solution is poured into water to obtain crude crystals. Otherwise, after an addition of water, the reaction solution is extracted with an organic solvent, and the extract is washed, if necessary, with a dilute alkaline aqueous solution, a dilute acidic aqueous solution or water and then subjected to usual aftertreatment such as drying or concentration to obtain a crude product.

The crude product may then be subjected to purification such as recrystallization, column chromatography, fractional liquid chromatography or fractional thin layer chromatography to obtain the desired compound of the present invention.

The compound of the present invention can be obtained by the synthesis route represented by Scheme (1) which includes the above process.

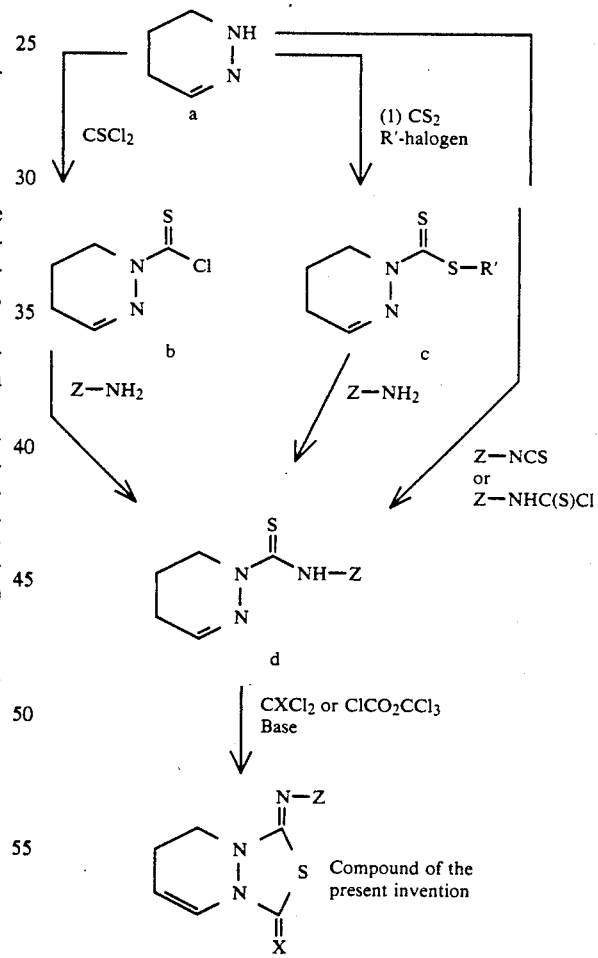

In Scheme (1), Z and X are defined above, and R' is a usual leaving group such as a lower alkyl group, a substituted benzyl group or $CH_2CO_2H$.

The starting compound 1,4,5,6-tetrahydropyridazine (a) can be prepared by the methods disclosed in e.g. Heyns Kurt, et al., Chem. Ber., 109 (11), 3707 (1976), N. Viswanathan, A. R. Sidhays, Tetrahedron Lett., 52, 5025, (1979), and David L. Klopotek, et al., J. Org.

Chem., 45 (9), 1665 (1980) or similar methods, or by entirely new methods as shown by Schemes (2) to (4).

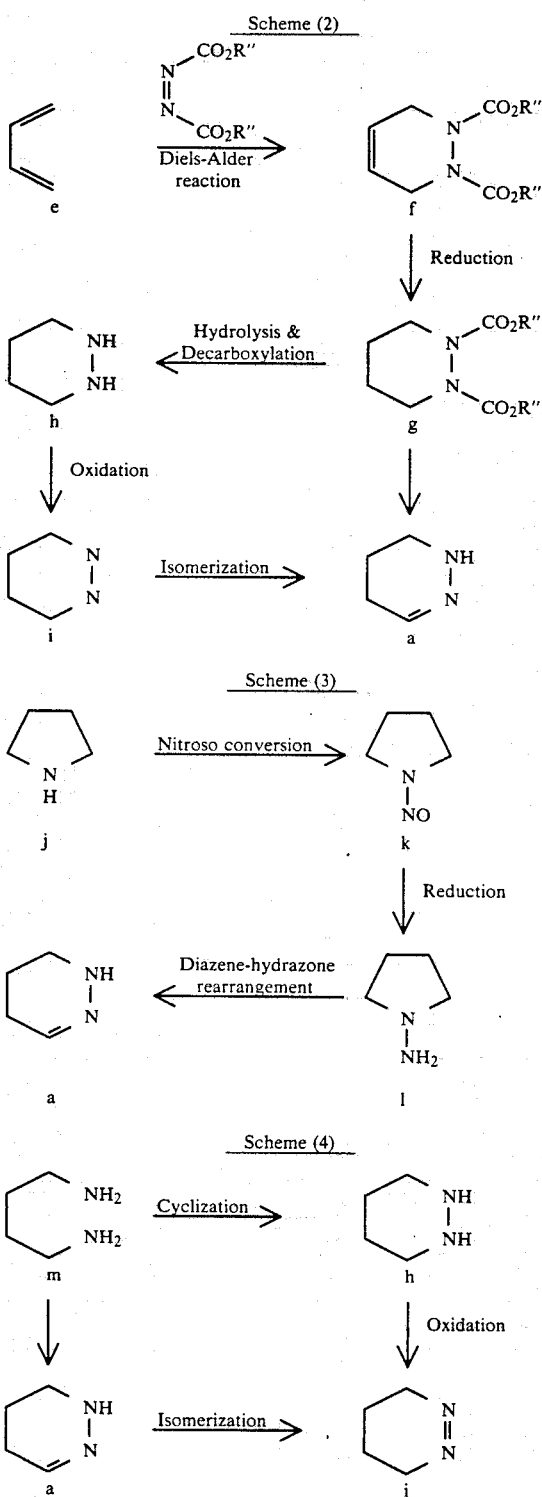

The step of g→a in Scheme (2), the steps of k→l and l→a in Scheme (3) and the step of m→a in Scheme (4) are novel processes. In scheme (2), R" is a lower alkyl group.

The starting materials and reagents used in the above methods are either known or can be prepared by the above-mentioned methods or other methods similar to such known methods.

Now, the syntheses of the compounds of the present invention and their intermediates will be described in detail as Examples and Reference Examples. However, it should be understood that the present invention is by no means restricted to such specific Examples.

EXAMPLE 1

Preparation of 9-(7-fluoro-3-oxo-4-propargyl-2H-1,4-benzoxazin-6-ylimino)-8-thia-1,6-diazabicyclo-[4.3.0]4-nonene-7-one (Compound No. 1074 of the present invention)

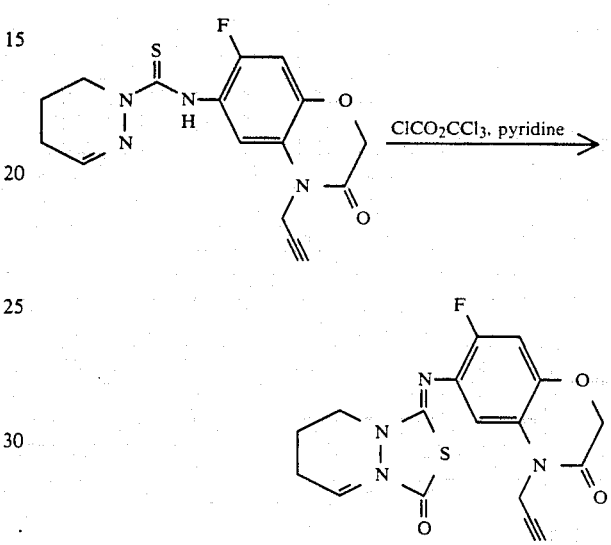

A mixed solution comprising 1.00 g of 1-(7-fluoro-3-oxo-4-propargyl-2H-1,4-benzoxazin-6-ylthiocarbamoyl)-1,4,5,6-tetrahydropyridazine, 0.50 g of pyridine and 10 ml of dichloromethane, was cooled to 0° C., and 0.21 ml of trichloromethyl chloroformate was added thereto. Twelve hours later, ice water was added thereto, and the organic layer was separated, washed with water and then with a saturated sodium chloride aqueous solution and dried over anhydrous sodium sulfate. Then, the solvent was distilled off to obtain a crude product. This crude product was purified by silica gel column chromatography (developing solvent: chloroform) to obtain 0.30 g of the above-identified compound as white crystals.

EXAMPLE 2

Preparation of 9-(7-fluoro-3-oxo-4-propargyl-2H-1,4-benzoxazin-6-ylimino)-8-thia-1,6-diazabicyclo[4.3.0]4-nonene-7-thione (Compound No. 1302 of the present invention)

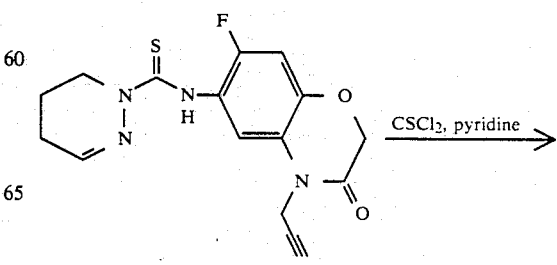

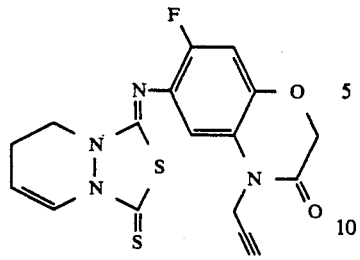

A mixed solution comprising 0.38 g of 1-(7-fluoro-3-oxo-4-propargyl-2H-benzoxazin-6-ylthiocarbamoyl)-1,4,5,6-tetrahydropyridazine, 0.24 g of pyridine and 5 ml of dichloromethane, was cooled to 0° C., and 0.10 ml of thiophosgene was added thereto. Twelve hours later, ice water was added thereto, and the organic layer was separated, washed with water and then with a saturated sodium chloride aqueous solution and dried over anhydrous sodium sulfate. The solvent was distilled off to obtain a crude product. This crude product was purified by silica gel column chromatography (developing solvent: chloroform) to obtain 0.10 g of the above-identified compound as white crystals.

EXAMPLE 3

Preparation of 9-(4-chloro-2-fluoro-5-isopropoxyphenylimino)-8-thia-1,6-diazabicyclo[4.3.0]4-nonene-7-one (Compound No. 15 of the present invention)

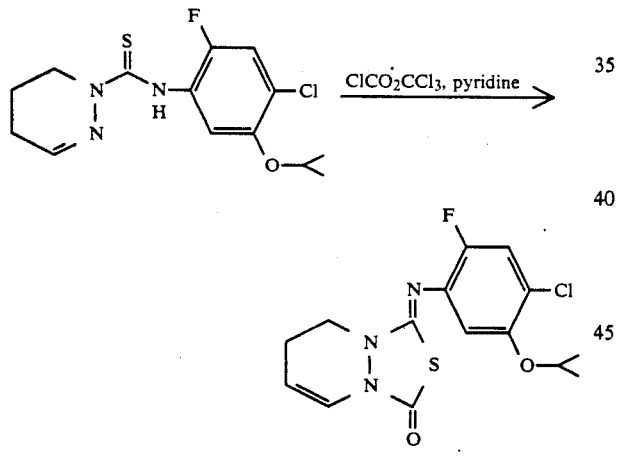

In the same manner as in Example 1, the above-identified compound was obtained as brown oil from 1-(4-chloro-2-fluoro-5-isopropoxyphenylthiocarbamoyl)-1,4,5,6-tetrahydropyridazine.

EXAMPLE 4

Preparation of 9-(4-chloro-2-fluoro-5-isopropoxyphenylimino)-8-thia-1,6-diazabicyclo[4.3.0]-4-nonene 7-thione (Compound No. 137 of the present invention)

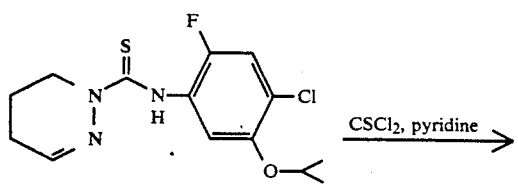

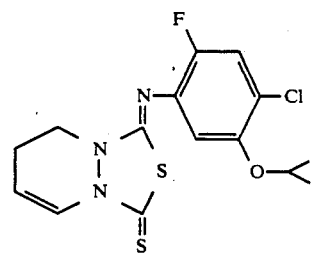

In the same manner as in Example 2, the above-identified compound was obtained as brown oil from 1-(4-chloro-2-fluoro-5-isopropoxyphenylthiocarbamoyl)-1,4,5,6-tetrahydropyridazine.

EXAMPLE 5

Preparation of 9-(4-chloro-2-fluoro-5-methoxycarbonylmethylthiophenylimino)-8-thia-1,6-diazabicyclo[4.3.0]4-nonene-7-one (Compound No. 61 of the present invention)

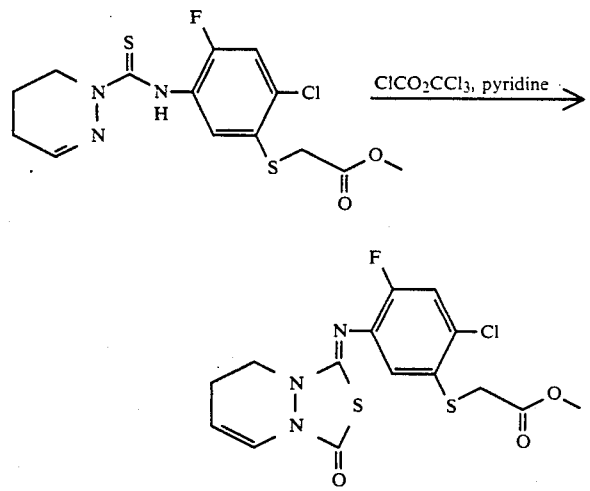

In the same manner as in Example 1, the above-identified compound was obtained as yellow oil from 1-(4-chloro-2-fluoro-5-methoxycarbonylmethylthiophenylthiocarbamoyl)-1,4,5,6-tetrahydropyridazine.

EXAMPLE 6

Preparation of 9-(4-chloro-2-fluoro-5-methoxycarbonylmethylthiophenylimino)-8-thia-1,6-diazabicyclo[4.3.0]4-nonene-7-thione (Compound No. 183 of the present invention)

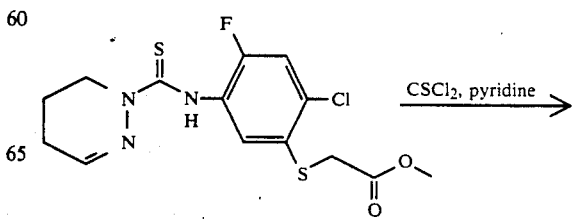

-continued

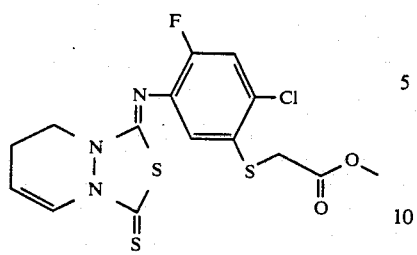

In the same manner as in Example 2, the above-identified compound was obtained as red oil from 1-(4-chloro-2-fluoro-5-methoxycarbonylmethylthiophenyl-thiocarbamoyl)-1,4,5,6-tetrahydropyridazine.

EXAMPLE 7

Preparation of 9-(4-chloro-3-methoxycarbonylmethylthiophenylimino)-8-thia-1,6-diazabicyclo[4.3.0]4-nonene-7-thione (Compound No. 308 of the present invention)

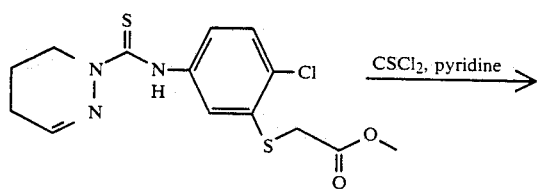

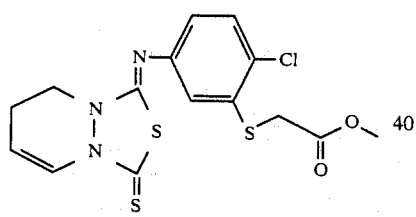

In the same manner as in Example 2, the above-identified compound was obtained as yellow crystals from 1-(4-chloro-3-methoxycarbonylmethylthiophenylthiocarbamoyl)-1,4,5,6-tetrahydropyridazine.

EXAMPLE 8

Preparation of 9-[4-chloro-2-fluoro-5-(2-tetrahydropyranylthio)-phenylimino]-8-thia-1,6-diazabicyclo-[4.3.0]4-nonene-7-one (Compound No. 607 of the present invention)

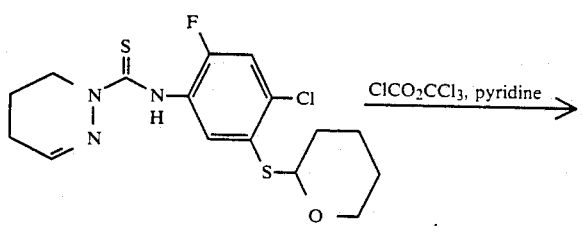

-continued

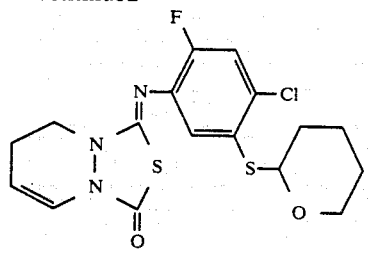

In the same manner as in Example 1, the above-identified compound was obtained as yellow oil from 1-[4-chloro-2-fluoro-5-(2-tetrahydropyranyl)thiophenylthiocarbamoyl]-1,4,5,6-tetrahydropyridazine.

EXAMPLE 9

Preparation of 9-(4-chloro-2-fluoro-5-mercaptophenylimino)-8-thia-1,6-diazabicyclo[4.3.0]4-nonene-7-one (Compound No. 11 of the present invention)

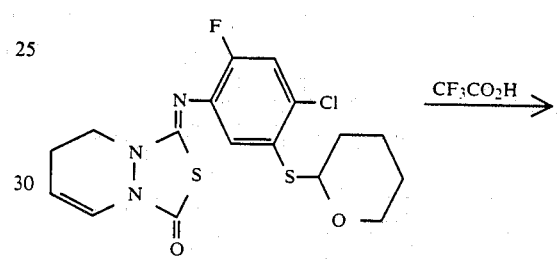

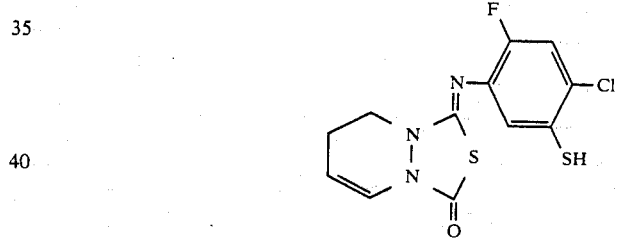

0.53 g of 9-[4-chloro-2-fluoro-5-(2-tetrahydropyranyl)thiophenylimino-8-thia-1,6-diazabicyclo[4.3.0]-4-nonene-7-one was dissolved in trifluoroacetic acid and heated at 50° C. for 5 hours. After distilling off trifluoroacetic acid, the residue was purified by fractional chromatography (developing solvent: hexane/ethyl acetate=2/1) to obtain 0.12 g of the above-identified compound as yellow oil.

EXAMPLE 10

Preparation of 9-(4-chloro-2-fluoro-5-methoxycarbonylmethylthiophenylimino)-8-thia-1,6-diazabicyclo-[4.3.0]-4-nonene-7-one (Compound No. 61 of the present invention)

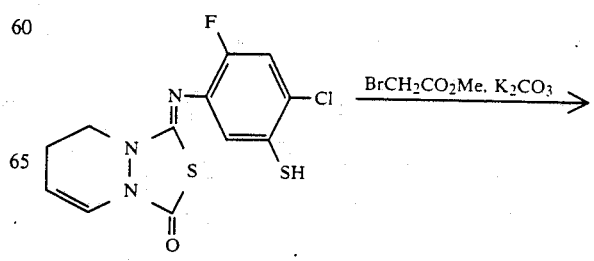

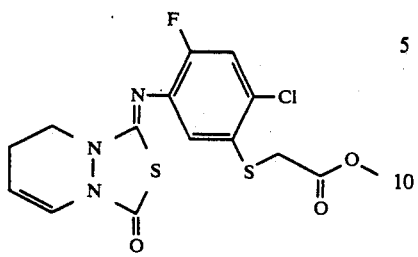

To a solution containing 0.50 g of 9-(4-chloro-2-fluoro-5-mercaptophenylimino)-8-thia-1,6-diazabicyclo]4.3.0]4-nonene-7-one and 0.21 g of anhydrous potassium carbonate in 5 ml of acetonitrile, 0.16 g of methyl chloroacetate was dropwise added at room temperature. Two hours layer, acetonitrile was distilled off, and the residue was dissolved in chloroform, washed with water and then with a saturated sodium chloride aqueous solution and dried over anhydrous sodium sulfate. Then, chloroform was distilled off to obtain a crude product. This crude product was purified by silica gel column chromatography (developing solvent: chloroform) to obtain 0.42 g of the above-identified compound as yellow oil.

EXAMPLE 11

Preparation of 9-[4-chloro-2-fluoro-5-(tetrahydro-2-oxo-3-franyl)thiophenylimino-8-thia-1,6-diazabicyclo-[4.3.0]4-nonene-7-one (Compound No. 686) of the present invention)

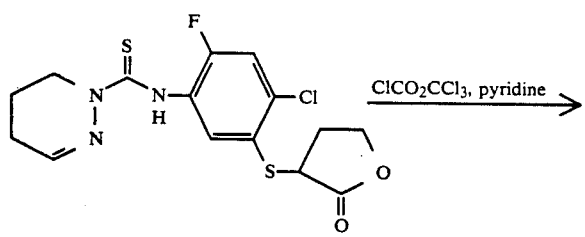

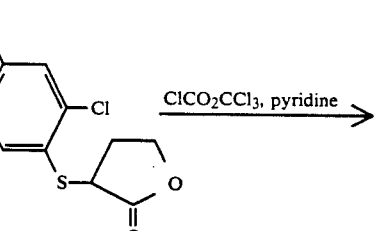

In the same manner as in Example 1, the above-identified compound was obtained as white crystals from 1-[4-chloro-2-fluoro-5-(tetrahydro-2-oxo-3-franyl)thiophenylthiocarbamoyl]-1,4,5,6-tetrahydropyridazine.

EXAMPLE 12

Preparation of 9-[4-chloro-2-fluoro-5-(2-acetoxyiminopropoxy)-phenylimino[4-thia-1,6-diazabicyclo[4.3.0]4-nonene-7-one (Compound No. 582 of the present invention)

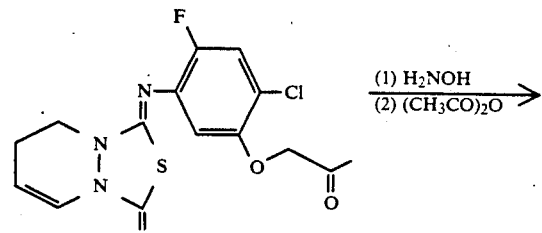

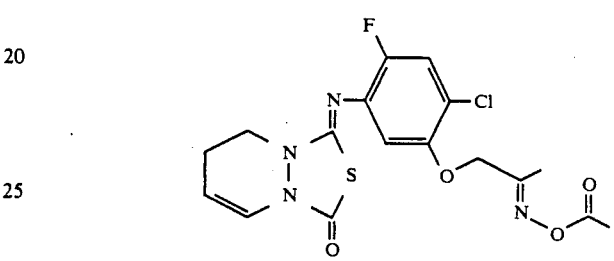

To a solution comprising 1.09 g of 9-[4-chloro-2-fluoro-5-(2-oxopropoxy)phenylimino]-8-thia-1,6-diazabicyclo[4.3.0]4-nonene-7-one, 0.35 g of pyridine and 10 ml of ethanol, 0.31 g of hydroxylamine hydrochloride was added. Three hours later, ethanol was distilled off, and the residue was extracted with ethyl acetate. The extract was washed with water and then with a saturated sodium chloride aqueous solution and dried over anhydrous sodium sulfate. Then, ethyl acetate was distilled off to obtain an oxime. Then, the oxime was dissolved in 7 ml of pyridine, and 0.21 g of acetic anhydride was added thereto. The mixture was left overnight, and then, pyridine was distilled off. The residue was dissolved in ethyl acetate, washed with a saturated sodium chloride aqueous solution and dried over anhydrous sodium sulfate. Then, ethyl acetate was distilled off to obtain a crude product. This crude product was purified by fractional chromatography to obtain 0.61 g of the above-identified compound as white crystals.

EXAMPLE 13

Preparation of 9-[4-chloro-2-fluoro-5-(1,3-dithiolan-2-methyl-2-ylmethoxy)phenylimino[-8-thia-1,6-diazabicyclo-[4.3.0]4-nonene-7-one (Compound No. 584 of the present invention)

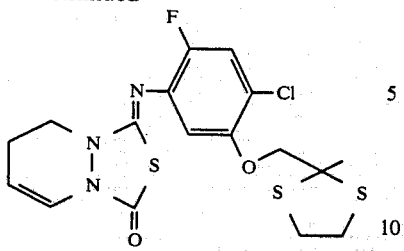

To a solution comprising 0.50 g of 9-[4-chloro-2-fluoro-5-(2-oxopropoxy)phenylimino[-thia-1,6-diazabicyclo[4.3.0]4-nonene-7-one, 0.17 ml of ethanedithiol and 5 ml of dichloromethane, 0.03 ml of a boron trifluoride/ether complex was added, and the mixture was stirred at room temperature for three hours. Ice water was added thereto, and then, the dichloromethane layer was separated, washed with a saturated sodium chloride aqueous solution and dried over anhydrous sodium sulfate. Then, dichloromethane was distilled off to obtain a crude product. The crude product was purified by fractional chromatography to obtain 0.47 g of the above-identified compound as yellow oil.

EXAMPLE 14

Preparation of 9-(4-chloro-2-fluoro-5-ethoxycarbonylphenylimino)-8-thia-1,6-diazabicyclo[4.3.0]4-nonene-7-one (Compound No. 80 of the present invention)

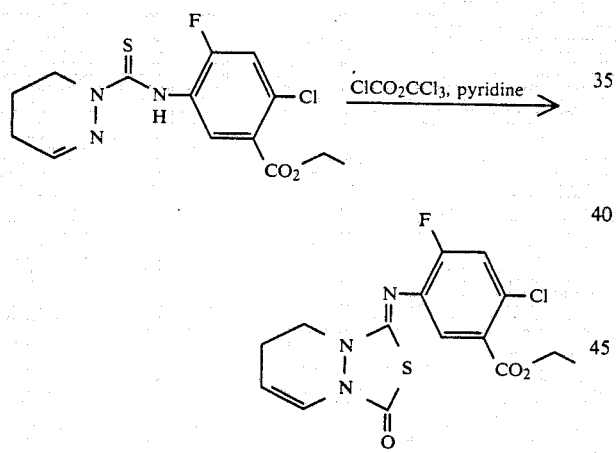

In the same manner as in Example 1, the above-identified compound was obtained as white crystals from 1-(4-chloro-2-fluoro-5-ethoxycarbonylphenylthiocarbamoyl)-1,4,5,6-tetrahydropyridazine.

Now, the physical properties of the compounds prepared in the same manner as in the preceding Examples 1 to 14 are shown in Table A together with the physical properties of the compounds of Example 1 to 14.

TABLE A

| Compound No. | $^1H$—NMR $\delta$ (ppm) [solvent] Physical properties |
|---|---|
| 11 | 2.32~2.70(2H, m), 4.04(2H, t, J=6Hz), 4.10~4.60(1H, m), 5.34(1H, dt, J=8, 4Hz), 6.89(1H, dt, J=8, 2Hz), 7.16(1H, d, J=8Hz), 7.18(1H, d, J=10Hz) [CDCl$_3$]oil |
| 15 | 1.36(6H, d, J=6Hz), 2.2~2.7(2H, m), 4.01(2H, t, J=6Hz), 4.38(1H, h, J=6Hz), 5.28(1H, dt, J=8, 4Hz), 6.51(1H, d, J=8Hz), 6.83(1H, dt, J=8, 2Hz), 7.07(1H, d, J=10 |

TABLE A-continued

| Compound No. | $^1H$—NMR $\delta$ (ppm) [solvent] Physical properties |
|---|---|
|  | Hz) [CDCl$_3$]oil |
| 28 | 2.24~2.72(2H, m), 3.77(3H, s), 4.04(2H, t, J=6Hz), 4.64(2H, s), 5.34(1H, dt, J=8, 4Hz), 6.53(1H, d, J=8Hz), 6.91(1H, dt, J=8, 2Hz), 7.19(1H, d, J=10Hz) [CDCl$_3$] mp = 112~114° C. |
| 29 | 1.26(3H, t, J=7Hz), 2.29~2.80(2H, m), 4.22 (2H, q, J=7Hz), 4.16(2H, t, J=6Hz), 4.62(2H, s), 5.31(1H, dt, J=8, 4Hz), 6.52(1H, d, J=8Hz), 6.87(1H, dt, J=8, 2Hz), 7.13(1H, d, J=10Hz), [CDCl$_3$] $n_D^{20}$ = 1.6090 |
| 35 | 1.34~1.96(8H, m), 2.28~2.72(2H, m), 4.02(2H, t, J=6Hz), 4.61(2H, s), 5.06~5.53(2H, m), 6.54(1H, d, J=8Hz), 6.88 (1H, dt, J=8, 2Hz), 7.13(1H, d, J=10Hz) [CDCl$_3$] $n_D^{20}$ = 1.5949 |
| 61 | 2.30~2.74(2H, m), 3.63(2H, s), 3.69 (3H, s), 4.06(2H, t, J=6Hz), 5.34(1H, dt, J=8, 4Hz), 6.91(1H, dt, J=8, 2Hz), 7.10 1H, d, J=8Hz), 7.20(1H, d, J=10Hz) [CDCl$_3$] $n_D^{22.0}$ = 1.6252 |
| 62 | 1.21(3H, t, J=7Hz), 2.31~2.75(2H, m), 3.61(2H, s), 4.07(2H, t, J=6Hz), 4.14(2H, q, J=7Hz), 3.36(1H, dt, J=8, 4Hz), 6.91(1H, dt, J=8, 2Hz), 7.11(1H, d, J=8Hz), 7.18(1H, d, J=10Hz) [CDCl$_3$] $n_D^{22.0}$ = 1.6260 |
| 64 | 1.19(6H, d, J=6Hz), 2.17~2.71(2H, m), 3.54(2H, s), 4.02(2H, t, J=6Hz), 4.93 (1H, h, J=6Hz), 5.29(1H, dt, J=8, 4Hz), 6.82(1H, dt, J=8, 2Hz), 7.00(1H, d, J=8Hz), 7.09(1H, d, J=8Hz), [CDCl$_3$]oil |
| 65 | 0.90(3H, br, t, J=6Hz), 1.0~1.9(4H, m), 2.3~2.8(2H, m), 3.58(2H, s), 4.03(2H, t, J=5Hz), 4.05(2H, t, J=6Hz), 5.29(1H, dt, J=8, 4Hz), 6.81(1H, dt, J=8, 2Hz), 7.00(1H, d, J=8Hz), 7.07(1H, d, J=10Hz) [CDCl$_3$] $n_D^{22.0}$ = 1.6194 |
| 68 | 1.16~2.16(8H, m), 2.30~2.80(2H, m), 3.58(2H, s), 4.06(2H, t, J=6Hz), 4.96~5.40(1H, m), 5.34(1H, dt, J=8, 4Hz), 6.90(1H, dt, J=8, 2Hz), 7.10(1H, d, J=8Hz), 7.17(1H, d, J=10Hz) [CDCl$_3$] $n_D^{22.0}$ = 1.6116 |
| 80 | 1.36(3H, t, J=7Hz), 2.26~2.71(2H, m), 4.02(2H, t, J=6Hz), 4.33(2H, q, J=7Hz), 5.35(1H, dt, J=8, 4Hz), 6.76(1H, dt, J=8, 2Hz), 7.06(1H, d, J=9Hz), 7.37(1H, d, J=8Hz) [CDCl$_3$] mp = 97~99° C. |
| 86 | 1.40~2.25(8H, m), 2.27~2.75(2H, m), 4.06(2H, t, J=5.5Hz), 5.1~5.56(1H, m), 5.31(1H, dt, J=8, 4Hz), 6.86(1H, dt, J=8, 2Hz), 7.16(1H, d, J=10Hz), 7.47(1H d, J=9Hz), [CDCl$_3$]oil |
| 137 | 1.33(6H, d, J=6Hz), 2.3~2.8(2H, m), 4.10(2H, t, J=6Hz), 4.41(1H, h, J=6Hz), 5.65(1H, dt, J=8, 4Hz), 6.54(1H, d, J=8Hz), 7.12(1H, d, J=10Hz), 7.53(1H, dt, J=8, 2 Hz), [CDCl$_3$]oil |
| 150 | 2.23~2.83(2H, m), 3.80(3H, s), 4.15 (2H, t, J=6Hz), 4.68(2H, s), 5.69(1H, dt, J=8, 4Hz), 6.5(1H, d, J=8Hz), 7.18(1H, d, J=10Hz), 7.60(1H, dt, J=8, 2Hz), [CDCl$_3$] mp = 130~131 ° C. |
| 151 | 1.29(3H, t, J=7Hz), 2.31~2.80(2H, m), 4.13(2H, t, J=6Hz), 4.25(2H, q, J=7Hz), 4.64(2H, s), 5.68(1H, dt, J=8, 4Hz), 6.53(1H, d, J=8Hz), 7.16(1H, d, J=10Hz), 7.56(1H, dt, J=8, 2Hz), [CDCl$_3$]oil |
| 157 | 1.31~2.10(8H, m), 2.35~2.80(2H, m), 4.14(2H, t, J=6Hz), 4.60(2H, s), 5.10~5.47(1H, m), 5.80(1H, dt, J=8, 4Hz), 6.53(1H, d, J=8Hz), 7.17(1H, d, J=10Hz), 7.59(1H, dt, J=8, 2Hz) [CDCl$_3$]oil |
| 183 | 2.38~2.78(2H, m), 3.62(2H, s), 3.70(3H, s), 4.14(2H, t, J=6Hz), 5.69(1H, dt, J=8, 4Hz), 7.07(1H, dt, J=8, 2Hz), 7.19(1H, d, J=10Hz), 7.57(1H, dt, J=8, 2Hz), [CDCl$_3$]oil |
| 184 | 1.21(3H, t, J=7Hz), 2.20~2.76(2H, m), |

TABLE A-continued

| Compound No. | 1H—NMR δ (ppm) [solvent] Physical properties |
|---|---|
|  | 3.61(2H, s), 4.07(2H, d, J=6Hz), 4.16 (2H, q, J=7Hz), 5.67(1H, dt, J=8, 4Hz), 7.06(1H, d, J=8Hz), 7.16(1H, d, J=10Hz), 7.54(1H, dt, J=8, 2Hz) [CDCl₃]oil |
| 190 | 1.40~2.05(8H, m), 2.35~2.80(2H, m), 3.56(2H, s), 4.13(2H, t, J=6Hz), 4.97~5.35(1H, m), 5.79(1H, dt, J=8, 4Hz), 7.08(1H, d, J=8Hz), 7.18(1H, d, J=10Hz), 7.58(1H, dt, J=8, 2Hz) [CDCl₃]oil |
| 201 | 2.37~2.86(2H, m), 4.03(3H, s), 4.28 (2H, t, J=6Hz, 5.83(1H, dt, J=8, 4Hz), 7.41(1H, d, J=10Hz), 7.74(1H, d, J=9Hz), 7.79(1H, dt, J=8, 4Hz), [CDCl₃] mp = 151~155° C. |
| 202 | 1.38(3H, t, J=7Hz), 2.36~3.41(2H, m), 4.14(2H, t, J=5Hz), 4.36(2H, q, J=7Hz), 5.67(1H, dt, J=8, 4Hz), 7.20(1H, d, J=10 Hz), 7.49(1H, d, J=9Hz), 7.57(1H, dt, J=8, 2Hz) [CDCl₃] mp = 147~151° C. |
| 208 | 1.25~2.24(8H, m), 2.31~2.73(2H, m), 4.09(2H, t, J=6Hz), 5.1~5.45(1H, m), 5.59(1H, dt, J=8, 4Hz), 7.05(1H, d, J=9Hz), 7.31(1H, d, J=8.2Hz), 7.42(1H, dt, J=8, 2Hz) [CDCl₃]oil |
| 276 | 2.3~2.7(2H, m), 3.68(3H, s), 3.68(2H, s), 3.68(3H, s), 3.97(2H, t, J=6Hz), 5.29(1H, dt, J=8, 4Hz), 6.70(1H, dd, J=10, 2Hz), 6.85(1H, dt, J=8, 2Hz), 6.93 (1H, d, J=2Hz), 7.28(1H, d, J=8Hz), [CDCl₃] $n_D^{22}$ = 1.6522 |
| 308 | 2.4~2.8(2H, m), 3.70(3H, s), 3.85(2H, s), 4.13(2H, t, J=6Hz), 5.80(1H, dt, J=8, 4Hz), 6.76(1H, dd, J=10, 2Hz), 6.92(1H, d, J=2Hz), 7.35(1H, d, J=8Hz), 7.55(1H, dt, J=8, 2Hz) [CDCl₃] mp = 96~98° C. |
| 340 | 2.25~2.73(2H, m), 3.69(5H, s), 4.06 (2H, t, J=5.5Hz), 5.31(1H, dt, J=8, 4Hz), 6.87(1H, dt, J=8, 2Hz), 6.95(1H, s), 7.40(1H, s) [CDCl₃]oil |
| 344 | 1.30~2.01(8H, m), 2.35~2.79(2H, m), 3.60(2H, s), 4.08(2H, t, J=6Hz), 5.05~5.55(2H, m), 6.93(1H, dt, J=8, 2Hz), 6.98(1H, s), 7.42(1H, s) [CDCl₃]oil |
| 376 | 1.05~2.20(8H, m), 2.31~2.85(2H, m), 3.62(2H, s), 4.13(2H, t, J=6Hz), 4.96~5.35(1H, m), 5.66(1H, dt, J=8, 4Hz), 6.95(1H, s), 7.40(1H, s), 7.53(1H, dt, J=8, 2Hz) [CDCl₃]oil |
| 408 | 1.05~2.06(8H, m), 2.15~2.66(2H, m), 3.54(2H, s), 4.02(2H, t, J=6Hz), 4.90~5.49(2H, m), 6.65~7.26(3H, m) [CDCl₃]oil |
| 440 | 1.12~2.17(8H, m), 2.27~2.77(2H, m), 3.53(2H, s), 4.10(2H, t, J=6Hz), 5.02~5.35(1H, m), 5.65(1H, dt, J=8, 4Hz), 6.92~7.37(2H, m), 7.58(1H, dt, J=8, 2Hz) [CDCl₃]oil |
| 468 | 2.36~2.79(2H, m), 3.79(3H, s), 3.93 (2H, s), 4.20(2H, t, J=6Hz), 5.55(1H, dt, J=8, 4Hz), 7.05(1H, dt, J=8, 2Hz), 7.22 (1H, d, J=8Hz), 8.17(1H, d, J=10Hz) [CDCl₃] mp = 142~145° C. |
| 500 | 2.50~2.80(2H, m), 3.75(3H, s), 4.23 (2H, t, J=6Hz), 5.84(1H, dt, J=8, 4Hz), 7.09(1H, d, J=8Hz), 7.58(1H, dt, J=8, 2Hz), 8.05(1H, d, J=10Hz), [d₆-DMSO] mp = 156~160° C. |
| 570 | 1.65(3H, d, J=7Hz), 2.3~2.7(2H, m), 3.75(3H, s), 4.06(2H, t, J=6Hz), 4.68 (1H, q, J=7Hz), 5.33(1H, dt, J=8, 4Hz), 6.54(1H, d, J=8Hz), 6.89(1H, dt, J=8, 2 Hz), 7.14(1H, d, J=10Hz) [CDCl₃] $n_D^{22}$ = 1.5843 |
| 577 | 2.30(3H, s), 2.30~2.65(2H, m), 4.02 (2H, t, J=6Hz), 4.49(2H, s), 5.31(1H, dt, J=8, 4Hz), 6.39(1H, d, J=8Hz), 6.84 (1H, dt, J=8, 2Hz), 7.10(1H, d, J=10Hz) [CDCl₃] mp = 116~118° C. |
| 579 | 1.95(3H, s), 2.34~2.73(2H, m), 3.14 (1H, s), 4.08(2H, t, J=6Hz), 4.87(2H, s), 5.42(1H, dt, J=8, 4Hz), 6.62(1H, d, J=8Hz), 6.94(1H, dt, J=8, 2Hz), 4.21(1H, d, J=10 Hz) [d₆-DMSO] mp = 174~176° C. |
| 580 | 1.95(3H, s), 2.30~2.73(2H, m), 3.85 (3H, s), 4.04(2H, t, J=6Hz), 4.51(2H, s), 5.30(1H, dt, J=8, 4Hz), 6.60(1H, d, J=8Hz), 6.88(1H, dt, J=8, 2Hz), 7.11(1H, d, J=10 Hz) [CDCl₃] mp = 121~123° C. |
| 582 | 2.20(3H, s), 2.23(3H, s), 2.33~2.73 (2H, m), 4.11(2H, t, J=6Hz), 4.95(2H, s), 5.40(1H, dt, J=8, 4Hz), 6.58(1H, d, J=8Hz), 6.94(1H, dt, J=8, 2Hz), 7.21(1H, d, J=10Hz) [CDCl₃] mp = 117~120° C. |
| 583 | 1.61(3H, s), 2.38~2.77(2H, m), 3.98 (2H, s), 4.15(4H, s), 4.15(2H, t, J=6Hz), 5.45(1H, dt, J=8, 4Hz), 6.70(1H, d, J=8Hz), 7.07(1H, dt, J=8, 2Hz), 7.30(1H, d, J=10Hz) [CDCl₃] mp = 95~98° C. |
| 584 | 1.93(3H, s), 2.29~2.73(2H, m), 3.39 (4H, s), 4.10(2H, s), 4.10(2H, t, J=6Hz), 5.41(1H, dt, J=8, 4Hz), 6.68(1H, d, J=8Hz), 7.00(1H, dt, J=8, 2Hz), 7.27(1H, d, J=10 Hz) [CDCl₃]oil |
| 606 | 2.2~2.7(2H, m), 3.77(2H, s), 4.11(2H, t, J=6Hz), 5.33(1H, dt, J=8, 4Hz), 6.85 (1H, dt, J=8, 2Hz), 7.21(1H, d, J=8Hz), 7.24(1H, d, J=10Hz) [CDCl₃] mp = 95~98° C. |
| 607 | 1.42~2.24(8H, m), 2.34~2.75(2H, m), 4.12(2H, t, J=6Hz), 5.39(1H, br t, J=4 Hz), 5.40(1H, dt, J=8, 4Hz), 7.01(1H, dt, J=8, 2Hz), 7.26(1H, d, J=8Hz), 7.27(1H, d. J=10Hz) [CDCl₃]oil |
| 612 | 1.45(3H, d, J=7Hz), 2.31~2.75(2H, m), 3.70(3H, s), 4.05(2H, t, J=5.5Hz), 5.08 (1H, q, J=7Hz), 5.32(1H, dt, J=8, 4Hz), 6.89(1H, dt, J=8, 2Hz), 7.12(1H, d, J=8Hz), 7.18(1H, d, J=9.4Hz) [CDCl₃] $n_D^{20}$ = 1.5982 |
| 613 | 1.21(3H, t, J=7Hz), 1.43(3H, d, J=7Hz), 2.31~2.70(2H, m), 3.67(2H, s), 4.02 (2H, t, J=6Hz), 4.12(2H, q, J=7Hz), 5.03(1H, q, J=7Hz), 5.28(1H, dt, J=8, 4Hz), 6.81(1H, dt, J=8, 2Hz), 7.04(1H, d, J=8Hz), 7.10(1H, d, J=10Hz) [CDCl₃]oil |
| 618 | 2.3~2.7(2H, m), 2.57(1H, t, J=2Hz), 3.68(2H, s), 4.05(2H, t, J=6Hz), 4.69 (2H, d, J=2Hz), 5.34(1H, dt, J=8, 4Hz), 6.89(1H, dt, J=8, 2Hz), 7.12(1H, d, J=8Hz), 7.20(1H, d, J=10Hz) [CDCl₃] $n_D^{20}$ = 1.6202 |
| 620 | 2.18~2.73(2H, m), 3.28(3H, s), 3.38~3.74(2H, m), 3.63(2H, s), 3.78~4.38 (4H, m), 5.27(1H, dt, J=8, 4Hz), 6.79 (1H, dt, J=8, 2Hz), 6.99(1H, d, J=8Hz), 7.07(1H, d, J=9.2Hz) [CDCl₃]oil |
| 639 | 1.5(3H, d, J=7Hz), 2.3~2.83(2H, m), 3.67(3H, s), 3.86(1H, q, J=7Hz), 4.09 (2H, t, J=5Hz), 5.36(1H, dt, J=8, 4Hz), 6.91(1H, dt, J=8, 2Hz), 7.22(1H, d, J=8Hz), 7.24(1H, d, J=10Hz) [CDCl₃] $n_D^{19}$ = 1.6241 |
| 640 | 1.16(3H, t, J=7Hz), 1.48(3H, d, J=7Hz), 2.32~2.71(2H, m), 3.81(1H, q, J=7Hz), 4.02(2H, t, J=6Hz), 4.06(2H, q, J=7Hz), 5.29(1H, dt, J=8, 4Hz), 6.82(1H, dt, J=8, 2Hz), 7.09(1H, d, J=8Hz), 7.11(1H, d, J=10Hz) [CDCl₃]oil |
| 644 | 1.20~2.05(8H, m), 1.46(3H, d, J=7.2Hz) 2.30~2.70(2H, m), 3.77(1H, q, J=7Hz), 4.02(2H, t, J=5.6Hz), 4.9~5.21(1H, m) 5.29(1H, dt, J=8, 4Hz), 6.81(1H, dt, J=8, 2Hz), 7.11(2H, d, J=9Hz) [CDCl₃] $n_D^{20}$ = 1.6021 |
| 661 | 1.05(3H, t, J=8Hz), 1.83(2H, dq, J=8Hz), 2.30~2.80(2H, m), 3.52(1H, t, J=8Hz), 3.65(3H, s), 4.07(2H, t, J=6Hz), 5.35 (1H, dt, J=8, 4Hz), 6.88(1H, dt, J=8, 2Hz), 7.16(1H, d, J=8Hz), 7.19(1H, d, J=10Hz), |

TABLE A-continued

| Compound No. | ¹H—NMR δ (ppm) [solvent] Physical properties |
|---|---|
| 675 | [CDCl₃]oil<br>1.00(3H, t, J=8Hz), 1.32~1.87(6H, m), 1.89(2H, dq, J=8Hz), 2.32~2.82(2H, m), 3.17~4.02(4H, m), 4.13(1H, t, J=8Hz), 4.17(2H, t, J=6Hz), 5.50(1H, dt, J=8, 4Hz), 7.06(1H, dt, J=8, 2Hz), 7.39(1H, d, J=8Hz), 7.41(1H, d, J=8Hz) [CDCl₃]oil |
| 686 | 1.86~3.06(4H, m), 2.74~4.28(3H, m), 4.34(2H, t, J=7Hz), 5.35(1H, dt, J=8, 4Hz), 6.90(1H, dt, J=8, 2Hz), 7.24(1H, d, J=10 Hz), 7.31(1H, d, J=9Hz) [CDCl₃] mp = 43~45° C. |
| 731 | 1.63(3H, d, J=7Hz), 2.3~2.7(2H, m), 3.74(3H, s), 4.10(2H, t, J=6Hz), 4.66 (1H, q, J=7Hz), 5.66(1H, dt, J=8, 4Hz), 6.49(1H, d, J=8Hz), 7.12(1H, d, J=10Hz), 7.53(1H, dt, J=8, 2Hz) [CDCl₃]oil |
| 738 | 2.27(3H, s), 2.32~2.82(2H, m), 4.08 (2H, br t, J=6Hz), 4.49(2H, s), 5.62 (1H, dt, J=8, 4Hz), 6.37(1H, d, J=8Hz), 7.08(1H, d, J=10Hz), 7.44(1H, dt, J=8, 2 Hz) [CDCl₃]oil |
| 767 | 2.3~2.8(2H, m), 3.64(2H, s), 4.13(2H, t, J=6Hz), 5.69(1H, dt, J=8, 4Hz), 7.25 (1H, d, J=8Hz), 7.26(1H, d, J=10Hz), 7.56(1H, dt, J=8, 2Hz) [CDCl₃] mp = 145~147° C. |
| 773 | 1.46(3H, d, J=7Hz), 2.31~2.83(2H, m), 3.70(3H, s), 4.12(2H, t, J=7Hz), 5.09 (1H, q, J=7Hz), 5.67(1H, dt, J=8, 4Hz), 7.12(1H, d, J=8.2Hz), 7.17(1H, d, J=10Hz), 7.58(1H, dt, J=8, 4Hz) [CDCl₃]oil |
| 774 | 1.15(3H, t, J=7Hz), 1.37(3H, d, J=7Hz), 2.28~2.66(2H, m), 3.59(2H, s), 4.03 (2H, t, J=6Hz), 4.05(2H, q, J=7Hz), 4.96 (1H, q, J=7Hz), 5.55(1H, dt, J=8, 4Hz), 6.98(1H, d, J=8Hz), 7.04(1H, d, J=10Hz), 7.43(1H, dt, J=8, 2Hz) [CDCl₃]oil |
| 779 | 2.3~2.8(2H, m), 2.50(1H, t, J=2Hz), 3.65(2H, s), 4.12(2H, t, J=6Hz), 4.68 (2H, d, J=2Hz), 5.67(1H, dt, J=8, 4Hz), 7.09(1H, d, J=8Hz), 7.18(1H, d, J=10Hz), 7.56(1H, dt, J=8, 2Hz) [CDCl₃]oil |
| 781 | 2.35~2.76(2H, m), 3.31(3H, s), 3.42~ 3.90(2H, m), 3.66(2H, s), 3.99~4.38 (4H, m), 5.68(1H, dt, J=8, 4Hz), 7.08(1H, d, J=8.2Hz), 7.18(1H, d, J=10Hz), 7.55 (1H, dt, J=8, 2Hz) [CDCl₃]oil |
| 800 | 1.5(3H, t, J=7Hz), 2.29~2.87(2H, m), 3.65(3H, s), 3.83(1H, q, J=7Hz), 4.13 (2H, t, J=5Hz), 5.70(1H, dt, J=8, 4Hz) 7.16(1H, d, J=9Hz), 7.20(1H, d, J=8.5Hz) 7.55(1H, dt, J=8, 2Hz) [CDCl₃]oil |
| 805 | 1.09~2.19(8H, m), 1.48(3H, d, J=7Hz), 2.29~2.84(2H, m), 3.79(1H, q, J=7Hz), 4.11(2H, t, J=5.5Hz), 4.89~5.35(1H, m), 5.65(1H, dt, J=8, 4Hz), 7.15(2H, d, J=8.2 Hz), 7.53(1H, dt, J=8, 2Hz) [CDCl₃]oil |
| 822 | 1.07(3H, t, J=8Hz), 1.92(2H, dq, J=8Hz), 2.40~2.80(2H, m), 3.67(1H, t, J=8Hz), 3.70(3H, s), 4.18(2H, t, J=6Hz), 5.72 (1H, dt, J=8, 4Hz), 7.20(1H, d, J=8Hz), 7.25(1H, d, J=10Hz), 7.65(1H, dt, J=8, 2 Hz) [CDCl₃]oil |
| 836 | 0.98(3H, t, J=8Hz), 1.30~1.70(6H, m), 1.83(2H, dq, J=8Hz), 2.35~2.75(2H, m), 3.20~3.76(4H, m), 4.05(1H, t, J=8Hz), 4.15(2H, t, J=6Hz), 5.72(1H, dt, J=8, 4Hz), 7.23(1H, dt, J=8, 2Hz), 7.24(1H, d, J=8Hz), 7.25(1H, d, J=10Hz) [CDCl₃]oil |
| 847 | 1.85~3.07(4H, m), 2.82~4.56(5H, m), 5.69(1H, dt, J=8, 4Hz), 7.21(1H, d, J=10 Hz), 7.29(1H, d, J=8Hz), 7.56(1H, dt, J= 8, 2Hz) [CDCl₃] mp = 54~57° C. |
| 1074 | 2.33(1H, t, J=2Hz), 2.4~2.6(2H, m), 4.10(2H, t, J=6Hz), 4.61(4H, br s), 5.35(1H, dt, J=8, 4Hz), 6.78(1H, d, J=8Hz), 6.80(1H, d, J=10Hz), 6.75~7.05(1H, m) [CDCl₃] mp = 137~138° C. |
| 1302 | 2.31(1H, t, J=2Hz), 2.5~2.8(2H, m), 4.10(2H, t, J=6Hz), 4.55(4H, br s), 5.61(1H, dt, J=8, 4Hz), 6.68(1H, d, J=8Hz), 6.80(1H, d, J=10Hz), 7.47(1H, dt, J=8, 2 Hz) [CDCl₃] mp = 208~210° C. |
| 609 | 1.39(9H, s), 2.31~2.68(2H, m), 3.51(2H, s), 4.01(2H, t, J=6Hz), 5.26(1H, dt, J=8, 4Hz), 6.78(1H, dt, J=8, 2Hz), 6.97(1H, d, J=8Hz), 7.04(1H, d, J=10Hz), [CDCl₃]oil |
| 770 | 1.44(9H, s), 2.31~2.81(2H, m), 3.60(2H, s), 4.19(2H, t, J=6Hz), 5.77(1H, dt, J=8, 4Hz), 7.20(1H, d, J=8Hz), 7.30(1H, d, J=10Hz), 7.71(1H, dt, J=8, 2Hz), [CDCl₃]oil |

REFERENCE EXAMPLE 1

Preparation of 1-(7-fluoro-3-oxo-4-propargyl-2H-benzoxazin-6-ylthiocarbamoyl)-1,4,5,6-tetrahydropyridazine

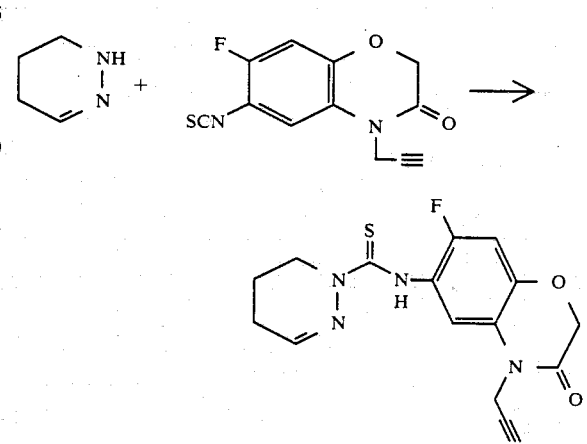

0.32 g of 1,4,5,6-tetrahydropyridazine was dissolved in 20 ml of benzene, and 1.00 g of 7-fluoro-4-propargyl-2H-benzoxazin-3(4H)-one-6-ylisothiocyanate was added thereto. The mixture was stirred at room temperature for 3 hours. After the reaction, benzene was distilled off to obtain a crude product. This crude product was purified by silica gel column chromatography (developing solvent: chloroform) to obtain 0.38 g of the above-identified compound as yellow crystals.

Melting point: 151°–155° C.

¹H-NMR(CDCl₃) δ: 1.94(2H, br t,J=6Hz), 2.1~2.4(2H,m),2.28(1H,t,J=2Hz), 4.30(2H,br,t,J=6Hz),4.61(2H,d, J=2Hz),4.62(2H,s),6.69(1H,d,J=10 Hz), 6.93(1H,t,J=2Hz), 8.02(1H,d, J=8Hz), 9.49(1H,br s)

REFERENCE EXAMPLE 2

Preparation of 1-(4-chloro-2-fluoro-5-isopropoxyphenylthiocarbamoyl)-1,4,5,6-tetrahydropyridazine

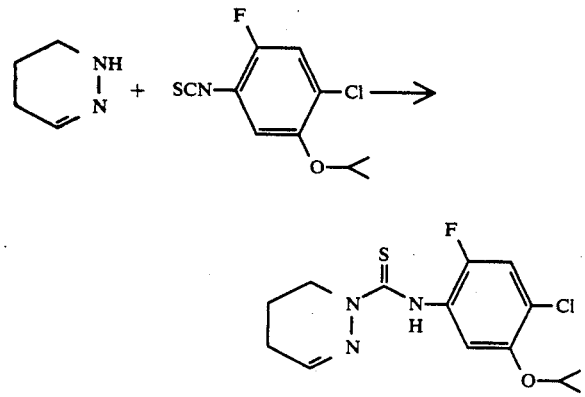

In the same manner as in Reference Example 1, the above-identified compound was obtained as white crystals from 1,4,5,6-tetrahydropyridazine and 4-chloro-2-fluoro-5-isopropoxyphenylisothiocyanate.

Melting point: 82°–83.5° C.

$^1$H-NMR(CDCl$_3$) δ: 1.35(6H,d,J=6Hz), 1.90(2H,br,t,J=6Hz), 2.0~2.4(2H,m),3.31(2H,br,t,J=6Hz), 4.54(1H, h,J=6Hz), 6.85(1H,br,t,J=2Hz), 7.08(1H,d,J=10Hz), 8.11(1H,d,J=8 Hz), 8.75(1H,br s)

REFERENCE EXAMPLE 3

Preparation of 1-(2-fluoro-5-methoxycarbonylmethylthio-4-nitrophenylthiocarbamoyl)-1,4,5,6-tetrahydropyridazine

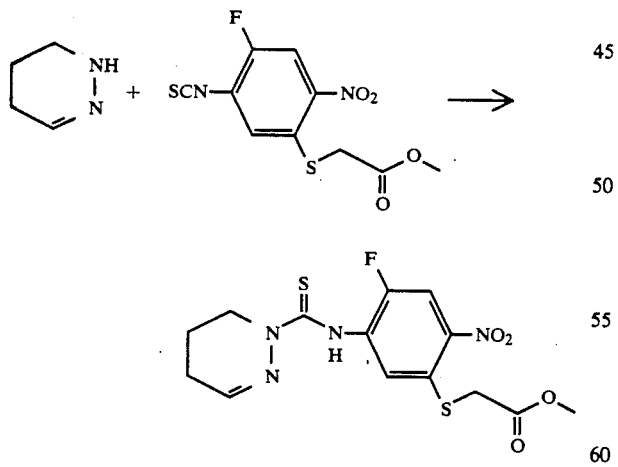

In the same manner as in Reference Example 1, the above-identified compound was obtained as yellow crystals from 1,4,5,6-tetrahydropyridazine and 2-fluoro-4-methoxycarbonylmethylthio-4-nitrophenylisothiocyanate.

Melting point: 184°–186° C.

REFERENCE EXAMPLE 4

Preparation of 1-(4-bromo-2-fluoro-5-cyclopentyloxycarbonylmethylthiophenylthiocarbamoyl)-1,4,5,6-tetrahydropyridazine

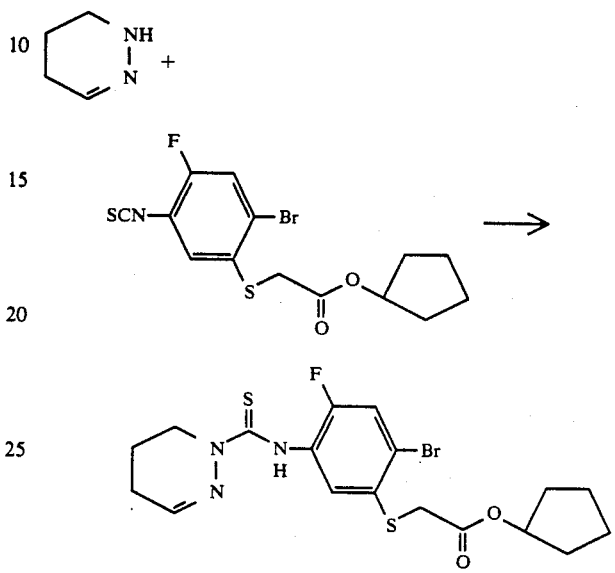

In the same manner as in Reference Example 1, the above-identified compound was obtained as brown oil from 1,4,5,6-tetrahydropyridazine and 4-bromo-2-fluoro-5-cyclopentyloxycarbonylmethylthiophenylisothiocyanate.

$^1$H-NMR(CDCl$_3$) δ: 1.38~2.53(12H,m), 3,63 (2H,s), 4.38(2H,t,J=5Hz), 5.08~5.38 (1H,m), 7.01~7.55(3H,m), 8.08(1H, br s)

REFERENCE EXAMPLE 5

Preparation of 1-[4-chloro-2-fluoro-5-(2-tetrahydropyranyl)thiophenylthiocarbamoyl]-1,4,5,6-tetrahydropyridazine

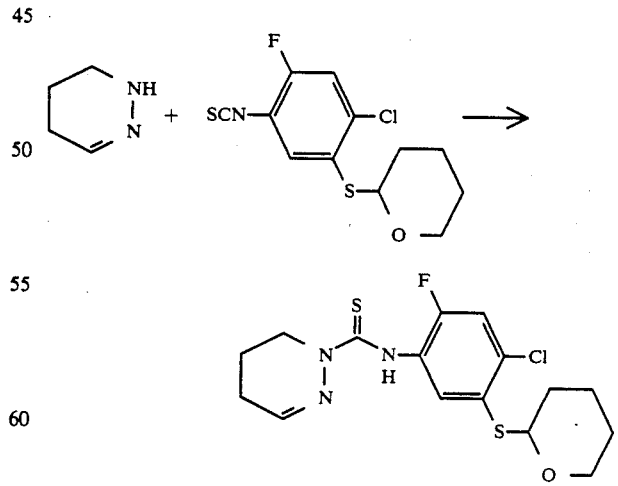

In the same manner as in Reference Example 1, the above-identified compound was obtained as white crystals from 1,4,5,6-tetrahydropyridazine and 4-chloro-2-fluoro-5-(2-tetrahydropyranyl)thiophenylisothiocynate.

Melting point: 101°–104° C.

$^1$H-NMR(CDCl$_3$) δ: 1.36~2.53(10H,m), 4.20~4.53(2H,m), 5.20~5.52(1H,m), 7.06(1H, t, J=2Hz), 7.22(1H,d,J=10Hz), 8.81(1H,d, J=8Hz), 9.87(1H,br s)

REFERENCE EXAMPLE 6

Preparation of 4-chloro-2-fluoro-5-(2-tetrahydropyranyl)thiophenylisothiocynate

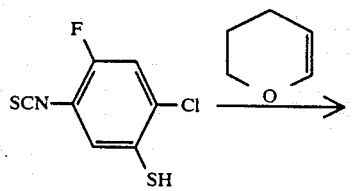

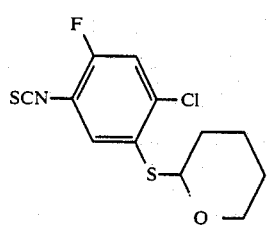

2.00 g of 4-chloro-2-fluoro-5-mercaptophenylisothiocyanate was dissolved in 20 ml of dichloromethane, and 0.77 g of dihydropyran was added thereto. Two hours later dichloromethane was distilled off to obtain 2.77 g of the above-identified compound as yellow oil.

REFERENCE EXAMPLE 7

Preparation of 4-chloro-2-fluoro-5-mercaptophenylisothiocyanate

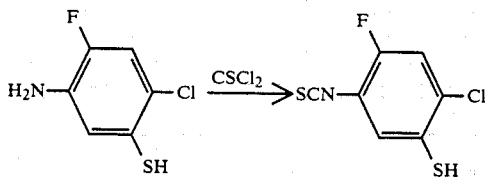

2.00 g of 4-chloro-2-fluoro-5-mercaptoaniline was dissolved in chloroform, and 1.12 ml of thiophosgene was dropwise added at 0° C. After the dropwise addition, the temperature was raised to room temperature and then, the mixture was refluxed. After refluxing for six hours, chloroform was distilled off to obtain 2.47 g of the above-identified compound as brown oil.

REFERENCE EXAMPLE 8

Preparation of 4-chloro-2-fluoro-5-(2-tetrahydropyranyl)oxyphenylisothiocyanate

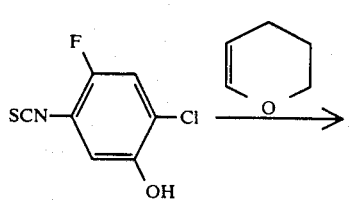

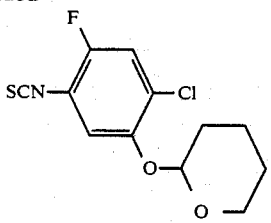

A dichloromethane solution containing 0.10 g of 4-chloro-2-fluoro-5-hydroxyphenylisothiocynate and 0.04 g of 2,3-dihydropyran, was stirred at room temperature for 5 hours. Then, dichloromethane was distilled off, and the residue was washed with diisopropyl ether to obtain 0.11 g of the above-identified compound as white crystals.

$^1$H-NMR(CDCl$_3$) δ: 1.30~2.23(8H,m), 3.27~4.13(2H,m), 5.34(1H, br s), 7.00(1H,d,J=8 Hz), 7.16(1H,d,J=10Hz)

REFERENCE EXAMPLE 9

Preparation of 4-chloro-2-fluoro-5-hydroxyphenylisothiocyanate

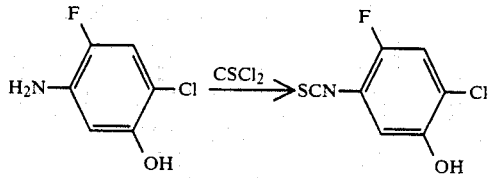

1.00 g of 4-chloro-2-fluoro-5-hydroxyaniline was dissolved in 10 ml of ethyl acetate, and 0.61 ml of thiophosgene was dropwise added at 0° C. After the dropwise addition, the temperature was raised to room temperature, and the mixture was refluxed. After refluxing for 6 hours, ethyl acetate was distilled off to obtain a crude product of crystals. This crude product was washed with hexane to obtain 0.70 g of the above-identified compound as gray crystals.

$^1$H-NMR(d$_6$-DMSO) δ: 6.79(1H,d,J=7Hz), 7.10 (1H,d,J=9Hz), 9.32(1H,br s)

REFERENCE EXAMPLE 10

Preparation of 1-(4-chloro-2-fluoro-5-cyclopentyloxycarbonylphenylthiocarbamoyl)-1,4,5,6-tetrahydropyridazine

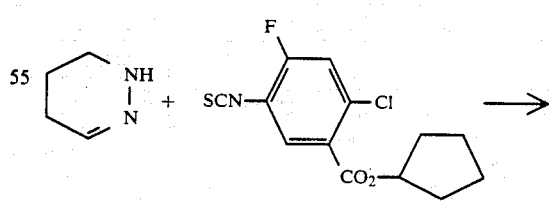

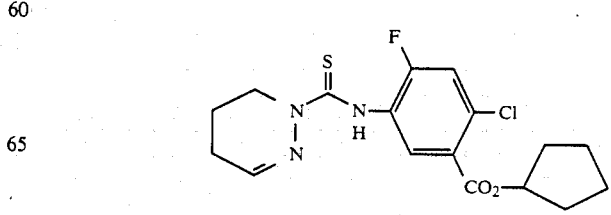

In the same manner as in Reference Example 1, the above-identified compound was obtained as slightly yellow crystals from 1,4,5,6-tetrahydropyridazine and 4-chloro-2-fluoro-5-cyclopentyloxycarbonylphenylisothiocyanate.

Melting point: 117°–120° C.

$^1$H-NMR(CDCl$_3$) δ: 1.40~2.61(12H,m), 4.25 (2H,t,J=5.5Hz), 5.1~5.56(1H,m), 6.88 (1H,br t, J=3Hz), 7.05(1H,d,J=10Hz), 8.70(1H,d,J=8Hz), 9.54(1H,br s)

REFERENCE EXAMPLE 11

Preparation of 1-(4-chloro-3-methoxycarbonylmethylthiophenylthiocarbamoyl)-1,4,5,6-tetrahydropyridazine

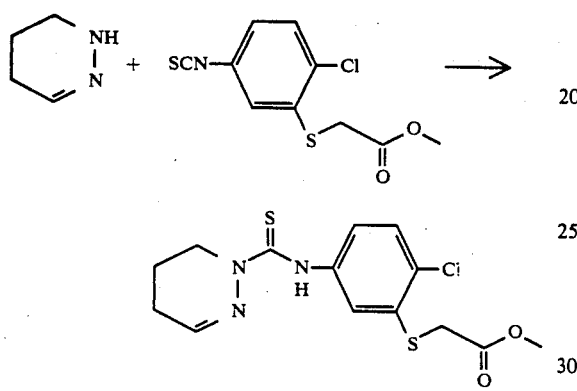

In the same manner as in Reference Example 1, the above-identified compound was obtained as white crystals from 1,4,5,6-tetrahydropyridazine and 4-chloro-3-methoxycarbonylmethylthiophenylisothiocyanate.

Melting point: 77°–80° C.

$^1$H-NMR(CDCl$_3$) δ: 1.60~2.48(4H,m), 3.73 (2H,s), 3.73(3H,s), 4.33(2H,t,J=6Hz), 7.05(1H,t,J=2Hz), 7.40(2H,br s), 7.93 (1H,br s), 9.90(1H, br s)

REFERENCE EXAMPLE 12

Preparation of 2-fluoro-5-methoxycarbonylmethylthio-4-nitroaniline

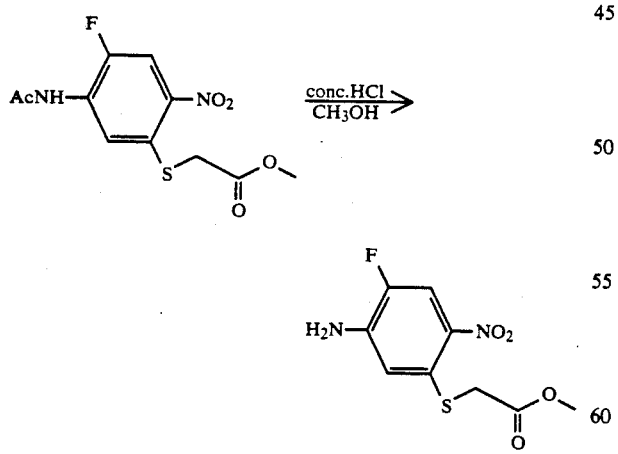

A solution comprising 6.09 g of 2-fluoro-5-methoxycarbonylmethylthio-4-nitroacetoanilide, 17 ml of concentrated hydrochloric acid and 84 ml of methanol, was refluxed for 5 hours. Methanol was distilled off, and the residue was diluted with water and neutralized with a 5% NaOH aqueous solution. Precipitated crystals were collected by filtration and washed with methanol to obtain 5.52 g of the above-identified compound as yellow crystals.

Melting point: 199°–202° C.

$^1$H-NMR(CDCl$_3$) δ: 3.80(3H,s), 3.88(2H,s), 6.58(2H,br s), 6.8(1H,d,J=10Hz), 8.02(1H, d, J=12Hz)

REFERENCE EXAMPLE 13

Preparation of 2-fluoro-5-methoxycarbonylmethylthio-4-nitroacetanilide

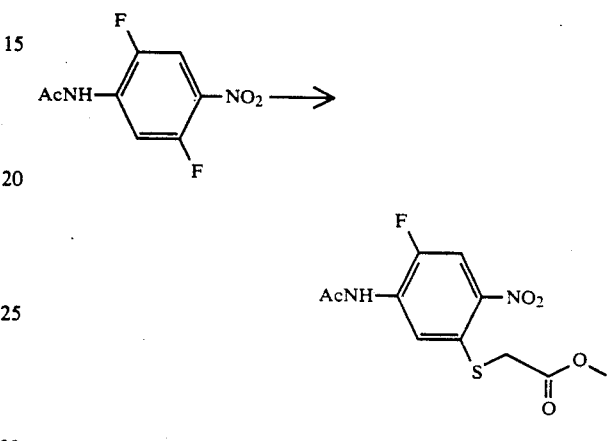

To a solution comprising 5.00 g of 2,5-difluoro-4-nitroacetanilide, 3.20 g of anhydrous potassium carbonate and 50 ml of dimethylformamide, 2.45 g of methyl thioglycolate was dropwise added. Three hours later, N,N-dimethylformamide was distilled off, and the residue was dissolved in ethyl acetate. The solution was washed with water and then with a saturated sodium chloride aqueous solution and dried over anhydrous sodium sulfate. Then, ethyl acetate was distilled off to obtain a crude product. The crude product was washed with diisopropyl ether to obtain 6.50 g of the above-identified compound as white crystals.

REFERENCE EXAMPLE 14

Preparation of 2,5-difluoro-4-nitroacetanilide

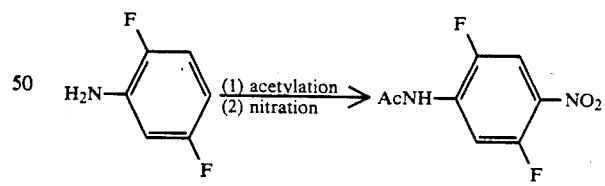

20.5 g of 2,5-difluoroaniline was dissolved in 68 ml of benzene, and 17.8 g of acetic anhydride was dropwise added. Fifteen hours later, benzene was distilled off, and the residue was washed with ethyl ether to obtain 25.6 g of 2,5-difluoroacetanilide as white crystals. Then, this compound was dissolved in 98% sulfuric acid, and 60% nitric acid was dropwise added at a temperature of not higher than 0° C. After the dropwise addition, the mixture was stirred for three hours at room temperature, and poured on ice. Precipitated crystals were collected by filtration and dried to obtain 25.9 g of the above-identified compound as yellow crystals.

Melting point: 182°–185° C.

$^1$H-NMR(CDCl$_3$) δ: 2.21(3H,s), 7.78(1H,dd,J=11.8Hz), 8.29(1H,dd,J=13.7Hz), 10.07(1H, br s)

REFERENCE EXAMPLE 15

Preparation of 1,4,5,6-tetrahydropyridazine

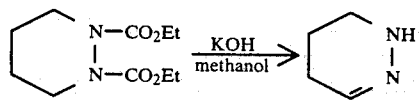

A mixture comprising 84.5 g of diethyl hexahydropyridazine-1,2-dicarboxylate, 96.9 g of potassium hydroxide and 857 ml of methanol, was refluxed for 24 hours. After the reaction, white solid was removed by filtration and methanol was distilled off to obtain a crude product. This crude product was distilled (57°-60° C./20 mmHg) to obtain 20.0 g of the above-identified compound as colorless transparent oil.

$^1$H-NMR(CDCl$_3$) δ: 1.8~2.3(4H,m), 3.04(2H, br t,J=5Hz), 3.2~3.7(1H,m), 6.68(1H,br t,J=2Hz)

REFERENCE EXAMPLE 16

Preparation of 1,4,5,6-tetrahydropyridazine

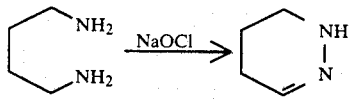

A solution comprising 100 g of 1,4-diaminobutane and 600 ml of water was heated to 70° C., and while maintaining the temperature, 1,700 g of an aqueous sodium hypochlorite solution (10%) was dropwise added over a period of 1.5 hours. After the dropwise addition, the mixture was stirred at 70° C. for 2 hours. The mixture was cooled to room temperature, and extracted with chloroform. The extract was dried over anhydrous sodium sulfate. Then, chloroform was distilled off to obtain a crude product. This crude product was distilled (57°-60° C./20 mmHg) to obtain 10.0 g of the above-identified compound as colorless transparent oil.

REFERENCE EXAMPLE 17

Preparation of 1,4,5,6-tetrahydropyridazine

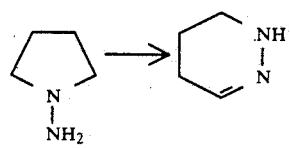

5.00 g of N-aminopyrrolidine was dissolved in 15 ml of chloroform, and the solution was stirred at room temperature for two weeks. Chloroform was distilled off and the residue was distilled, (57°-60° C./20 mmHg) to obtain 3.50 g of the above-identified compound as colorless oil.

REFERENCE EXAMPLE 18

Preparation of 1-aminopyrrolidine

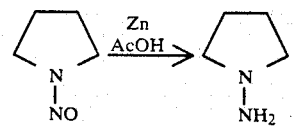

To a mixture comprising 146 g of 1-nitrosopyrrolidine, 340 g of zinc powder and 1,560 ml of water, 1,522 ml of 85% acetic acid was dropwise added. Two hours later, insoluble substances were filtered off, and the residue was neutralized with a 40% sodium hydroxide aqueous solution and extracted with chloroform. The extract solutions obtained by the extracting operation of five times were put together and washed with a saturated sodium chloride aqueous solution, and then dried over anhydrous sodium sulfate. Chloroform was distilled off to obtain 124 g of the above-identified compound as colorless oil.

$^1$H-NMR(CDCl$_3$) δ: 1.52~2.17(4H,m), 2.43~2.94(4H,m), 3.52(1H,br s)

Now, the physical properties of the compounds prepared in the same manner as in Reference Examples 1-5, 10 and 11 (thiosemicarbazone derivatives of the formula II) will be presented in Table B together with the results of the above Reference Examples.

The Z portion of the formula in Table B corresponds to the Z portion of the compound of the present invention shown in Table 1 (see the formula I), and the Z portion in Table B is indicated by the compound No. of the present invention.

TABLE B

| Z | $^1$H-NMR (solvent) | δ (ppm) Physical properties |
|---|---|---|
| 15-137 | | 1.35(6H, d, J=6Hz), 1.90(2H, brt, J=6Hz), 2.0~2.4(2H, m), 4.31(2H, brt, J=6Hz), 4.54(1H, h, J=6Hz), 6.85(1H, brt, J=2Hz), 7.08(1H, d, J=10Hz), 8.11(1H, d, J=8Hz), 8.75(1H, brs) (CDCl$_3$) mp=82~83.5° C. |
| 28-150 | | 1.64~2.61(4H, m), 3.71(3H, s), 4.26(2H, brt, J=6Hz), 4.8(2H, s), 7.14(1H, t, J=2Hz), 7.32(1H, d, J=10Hz), 7.74(1H, d, J=8Hz), 9.94(1H, brs) (d$_6$-DMSO) mp=181~184° C. |
| 29-151 | | 1.30(3H, t, J=7Hz), 1.67~2.47(4H, m), 4.25(2H, q, J=7Hz), 4.30(2H, brt, J=6Hz), 7.01(1H, t, J=2Hz), 7.15(1H, d, J=10Hz), 8.44(1H, d, J=8Hz), 9.98(1H, brs) (CDCl$_3$) mp=132~135° C. |
| 35-157 | | 1.38~2.47(12H, m), 4.30(2H, brt, J=6Hz), 4.61(2H, s), 5.08~5.40(1H, m), 6.98(1H, t, J=2Hz), 7.07(1H, d, J=10Hz), 8.39(1H, d, J=8Hz), 9.89(1H, brs) (CDCl$_3$) mp=121~124° C. |
| 61-183 | | 1.5~2.56(4H, m), 3.61(3H, s), 3.80(2H, s), 4.20(2H, brt, J=6Hz), 7.05(1H, brt, J=2Hz), 7.32(1H, d, J=10Hz), 7.79(1H, d, J=8Hz), 9.81(1H, brs) (CDCl$_3$) mp=116~118° C. |
| 62-184 | | 1.23(3H, t, J=7Hz), 1.70~2.56(4H, m), 3.69(2H, s), 4.16(2H, q, J=7Hz), 4.31(2H, brt, J=6Hz), 7.06(1H, brt, J=2Hz), 7.22(1H, d, J=10Hz), 8.68(1H, d, J=8Hz), |

TABLE B-continued

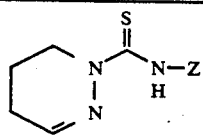

| Z | ¹H-NMR (solvent) δ (ppm) Physical properties |
|---|---|
| 64 | 9.87(1H, s) (CDCl₃) mp=149~151° C. 1.20(6H, d, J=7Hz), 1.64~2.48(4H, m), 3.63(2H, s), 4.27(2H, brt, J=6Hz), 4.94(1H, h, J=7Hz), 6.90(1H, t, J=2Hz), 7.07(1H, d, J=10Hz), 8.46(1H, d, J=8Hz), 9.69(1H, brs) (CDCl₃) oil |
| 65 | 0.88(3H, brt, J=6Hz), 1.15~2.48(8H, m), 3.66(2H, s), 4.08(2H, brt, J=6Hz), 4.28(2H, brt, J=6Hz), 6.90(1H, t, J=2Hz), 7.06(1H, d, J=10Hz), 8.46(1H, d, J=8Hz), 9.61(1H, brs) (CDCl₃) oil |
| 68-190 | 1.37~2.52(12H, m), 3.67(2H, s), 4.31(2H, brt, J=6Hz), 4.98~5.37(1H, m), 7.02(1H, brt, J=2Hz), 7.18(1H, d, J=10Hz), 8.60(1H, d, J=8Hz), 9.83(1H, brs) (CDCl₃) oil |
| 201 | 1.51~2.52(4H, m), 3.87(3H, s), 4.29(2H, brt, J=6Hz), 6.94(1H, brt, J=3Hz), 7.15(1H, d, J=10Hz), 8.79(1H, d, J=8Hz), 9.61(1H, brs) (CDCl₃) mp=151~154° C. |
| 80-202 | 1.35(3H, t, J=7.5Hz), 1.64~2.50(4H, m), 4.36(2H, q, J=4Hz), 7.06(1H, brt, J=3Hz), 7.27(1H, d, J=10Hz), 8.95(1H, d, J=8Hz), 9.84(1H, brs) (CDCl₃) mp=107~110° C. |
| 86-208 | 1.4~2.55(12H, m), 4.25(2H, brt, J=5Hz), 5.1~5.46(1H, m), 6.88(1H, t, J=3Hz), 7.04(1H, d, J=9Hz), 8.79(1H, d, J=8Hz), 9.53(1H, brs) (CDCl₃) mp=117~120° C. |
| 276-308 | 1.60~2.48(4H, m), 3.73(2H, s), 3.73(3H, s), 4.33(2H, t, J=6Hz), 7.05(1H, t, J=2Hz), 7.40(2H, brs), 7.93(1H, brs), 9.90(1H, brs) mp=77~80° C. |
| 340 | 1.49~2.54(4H, m), 4.26(5H, s), 4.35(2H, brt, J=5.5Hz), 7.06(1H, brt, J=2Hz), 7.35(1H, s), 8.70(1H, s) (CDCl₃) mp=140~142° C. |
| 344-376 | 1.29~2.84(12H, m), 3.74(2H, s), 4.35(2H, brt, J=6Hz), 4.99~5.35(1H, m), 7.09(1H, brt, J=3Hz), 7.44(1H, s), 8.79(1H, s) (CDCl₃) mp=112~115° C. |
| 408-440 | 1.38~2.53(12H, m), 3.63(2H, s), 4.38(2H, t, J=5.5Hz), 5.08~5.38(1H, m), 7.01~7.55(3H, m), 8.08(1H, brs) (CDCl₃) oil |
| 570-731 | 1.69(3H, d, J=7Hz), 1.74~2.54(4H, m), 3.85(3H, s), 4.40(2H, t, J=6Hz), 4.86(1H, q, J=7Hz), 7.14(1H, t, J=2Hz), 7.29(1H, d, J=10Hz), 8.53(1H, d, J=8Hz), 10.13(1H, brs) (CDCl₃) mp=118~121° C. |
| 577-738 | 1.65~2.60(4H, m), 2.26(3H, s), 4.27(2H, brt, J=6Hz), 4.71(2H, s), 7.11(1H, t, J=2Hz), 7.25(1H, d, J=10Hz), 7.92(1H, d, J=8Hz), 9.94(1H, brs) (CDCl₃) mp=145~148° C. |
| 606-767 | 1.68~2.67(4H, m), 3.91(2H, s), 4.31(2H, brt, J=6Hz), 7.13(1H, t, J=2Hz), 7.36(1H, d, J=10Hz), 8.53(1H, d, J=8Hz), 9.98(1H, brs) (d₆-DMSO) mp=153~156° C. |
| 607 | 1.36~2.53(10H, m), 4.20~4.53(2H, m), 4.36(2H, t, J=6Hz), 5.20~5.52(1H, m), 7.06(1H, t, J=2Hz), 7.22(1H, d, J=10Hz), 8.81(1H, d, J=8Hz), 9.87(1H, brs) (CDCl₃) mp=101~104° C. |
| 612-773 | 1.44(3H, t, J=7Hz), 1.69~2.51(4H, m), 3.68(3H, s), 3.74(2H, s), 4.30(2H, brt, J=5Hz), 5.08(1H, q, J=7Hz), 6.98(1H, t, J=2Hz), 7.14(1H, d, J=10Hz), 8.51 (1H, d, J=8Hz), 9.77(1H, brs) (CDCl₃) oil |
| 613-774 | 1.20(3H, t, J=7Hz), 1.47(3H, d, J=7Hz), 1.68~2.38(4H, m), 3.73(2H, s), 4.13(2H, q, J=7Hz), 4.23(2H, t, J=6Hz), 5.13(1H, q, J=7Hz), 6.91(1H, t, J=2Hz), |

TABLE B-continued

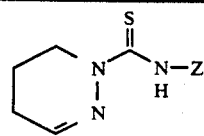

| Z | ¹H-NMR (solvent) δ (ppm) Physical properties |
|---|---|
| | 7.08(1H, d, J=10Hz), 8.43(1H, d, J=8Hz), 9.61(1H, brs) (CDCl₃) oil |
| 675-836 | 1.01(3H, t, J=7Hz), 1.42~1.75(6H, m), 1.77~2.55(6H, m), 3.27~3.80(4H, m), 4.10(1H, t, J=7Hz), 4.37(2H, t, J=6Hz), 7.08(1H, t, J=2Hz), 7.23(1H, d, J=10Hz), 8.74(1H, d, J=8Hz), 9.87(1H, brs) (CDCl₃) oil |
| 686-847 | 1.49~3.18(6H, m), 3.82~4.66(5H, m), 7.04(1H, brt, J=2Hz), 7.22(1H, d, J=11Hz), 8.64(1H, d, J=8Hz), 9.83(1H, brs) (CDCl₃) oil |
| 1074-1302 | 1.94(2H, brt, J=6Hz), 2.1~2.4(2H, m), 2.28(1H, t, J=2Hz), 4.30(2H, brt, J=6Hz), 4.61(2H, d, J=2Hz), 4.62(2H, s), 6.69(1H, d, J=10Hz), 6.93(1H, t, J=2Hz), 8.02(1H, d, J=8Hz), 9.49(1H, brs) (CDCl₃) mp=151~155° C. |
| 609-770 | 1.46(9H, s), 1.67~2.43(4H, m), 3.67(2H, s), 4.36(2H, brt, J=6Hz), 6.80(1H, t, J=2Hz), 7.11(1H, t, J=4Hz), 7.32(1H, d, J=3Hz), 9.83(1H, brs) (CDCl₃) oil |
| 640 | 1.29(3H, t, J=8Hz), 1.47(3H, d, J=8Hz), 1.77~2.17(2H, m), 1.97~2.50(2H, m), 3.85(1H, q, J=8Hz), 4.10(2H, q, J=8Hz), 4.33(2H, brt, J=6Hz), 6.94(1H, t, J=2Hz), 7.12(1H, d, J=10Hz), 8.04(1H, d, J=8Hz), 9.63(1H, brs) (CDCl₃) oil |
| 644-805 | 1.53(3H, d, J=7Hz), 1.55~2.82(8H, m), 2.80~3.51(4H, m), 3.88(1H, q, J=7Hz), 4.33(2H, brt, J=6Hz), 5.00~5.29(1H, m), 7.01(1H, t, J=3Hz), 7.19(1H, d, J=10Hz), 8.61(1H, d, J=8Hz), 9.73(1H, brs) (CDCl₃) oil |
| 661-822 | 1.05(3H, t, J=7Hz), 1.66~2.49(6H, m), 4.16(1H, t, J=7Hz), 4.33(2H, t, J=6Hz), 7.02(1H, d, J=10Hz), 7.20(1H, d, J=10Hz), 8.67(1H, d, J=8Hz), 9.77(1H, brs), (CDCl₃) oil |
| 675-836 | 1.01(3H, t, J=7Hz), 1.42~1.75(6H, m), 1.77~2.55(6H, m), 3.27~3.80(4H, m), 4.10(1H, t, J=7Hz), 4.37(2H, t, J=6Hz), 7.08(1H, t, J=2Hz), 7.23(1H, d, J=10Hz), 8.74(1H, d, J=8Hz), 9.87(1H, brs) (CDCl₃) oil |
| 686-847 | 1.49~3.18(6H, m), 3.82~4.66(5H, m), 7.04(1H, brt, J=2Hz), 7.22(1H, d, J=11Hz), 8.64(1H, d, J=8Hz), 9.83(1H, brs) (CDCl₃) oil |
| 1074-1302 | 1.94(2H, brt, J=6Hz), 2.1~2.4(2H, m), 2.28(1H, t, J=2Hz), 4.30(2H, brt, J=6Hz), 4.61(2H, d, J=2Hz), 4.62(2H, s), 6.69(1H, d, J=10Hz), 6.93(1H, t, J=2Hz), 8.02(1H, d, J=8Hz), 9.49(1H, brs) (CDCl₃) mp=15~155° C. |
| 609-770 | 1.46(9H, s), 1.67~2.43(4H, m), 3.67(2H, s), 4.36(2H, brt, J=6Hz), 6.80(1H, t, J=2Hz), 7.11(1H, t, J=4Hz), 7.32(1H, d, J=3Hz), 9.83(1H, brs) (CDCl₃) oil |

Now, Examples of the compounds of the present invention will be presented in Table 1 (Z=Z1) and in Table 2 (Z=Z2) together with the compounds prepared in the foregoing Examples. However, it should be understood that the compound of the present invention is by no means restricted by these specific Examples.

TABLE 1

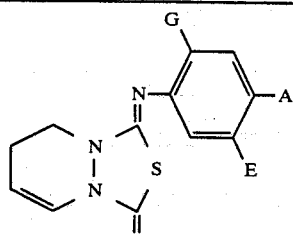

| No. | X | G | A | E |
|---|---|---|---|---|
| 1 | O | F | Cl | H |
| 2 | O | F | Cl | CH$_3$ |
| 3 | O | F | Cl | C$_2$H$_5$ |
| 4 | O | F | Cl | F |
| 5 | O | F | Cl | Cl |
| 6 | O | F | Cl | Br |
| 7 | O | F | Cl | C≡N |
| 8 | O | F | Cl | NO$_2$ |
| 9 | O | F | Cl | NH$_2$ |
| 10 | O | F | Cl | OH |
| 11 | O | F | Cl | SH |
| 12 | O | F | Cl | OCH$_3$ |
| 13 | O | F | Cl | OC$_2$H$_5$ |
| 14 | O | F | Cl | OCH$_2$CH$_3$ |
| 15 | O | F | Cl | OCH(CH$_3$)$_2$ |
| 16 | O | F | Cl | OCH$_2$(CH$_2$)$_2$CH$_3$ |
| 17 | O | F | Cl | 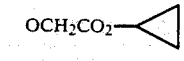 |
| 18 | O | F | Cl | 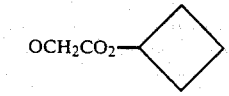 |
| 19 | O | F | Cl | 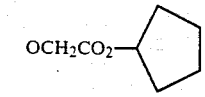 |
| 20 | O | F | Cl | 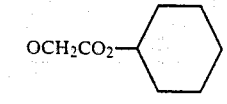 |
| 21 | O | F | Cl | 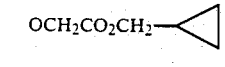 |
| 22 | O | F | Cl | 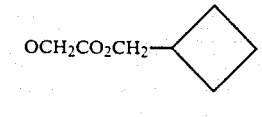 |
| 23 | O | F | Cl | 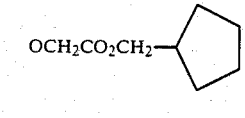 |
| 24 | O | F | Cl | 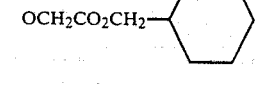 |
| 25 | O | F | Cl | OCH$_2$CH=CH$_2$ |
| 26 | O | F | Cl | OCH$_2$C≡CH |
| 27 | O | F | Cl | OCH$_2$CO$_2$H |
| 28 | O | F | Cl | OCH$_2$CO$_2$CH$_3$ |
| 29 | O | F | Cl | OCH$_2$CO$_2$C$_2$H$_5$ |
| 30 | O | F | Cl | OCH$_2$CO$_2$CH$_2$CH$_2$CH$_3$ |
| 31 | O | F | Cl | OCH$_2$CO$_2$CH(CH$_3$)$_2$ |
| 32 | O | F | Cl | OCH$_2$CO$_2$CH$_2$(CH$_2$)$_2$CH$_3$ |

TABLE 1-continued

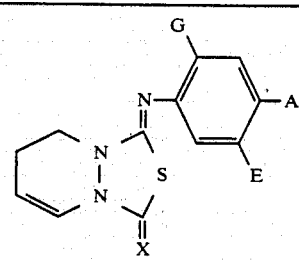

| No. | X | G | A | E |
|---|---|---|---|---|
| 33 | O | F | Cl | OCH$_2$CO$_2$-△ |
| 34 | O | F | Cl | OCH$_2$CO$_2$-□ |
| 35 | O | F | Cl | OCH$_2$CO$_2$-⬠ |
| 36 | O | F | Cl | OCH$_2$CO$_2$-⬡ |
| 37 | O | F | Cl | OCH$_2$CO$_2$CH$_2$-△ |
| 38 | O | F | Cl | OCH$_2$CO$_2$CH$_2$-□ |
| 39 | O | F | Cl | OCH$_2$CO$_2$CH$_2$-⬠ |
| 40 | O | F | Cl | OCH$_2$CO$_2$CH$_2$-⬡ |
| 41 | O | F | Cl | OCH$_2$OCH$_3$ |
| 42 | O | F | Cl | OCH$_2$OC$_2$H$_5$ |
| 43 | O | F | Cl | OCH$_2$CH$_2$OCH$_3$ |
| 44 | O | F | Cl | OCH$_2$CH$_2$OC$_2$H$_5$ |
| 45 | O | F | Cl | SCH$_3$ |
| 46 | O | F | Cl | SC$_2$H$_5$ |
| 47 | O | F | Cl | SCH$_2$CH$_2$CH$_3$ |
| 48 | O | F | Cl | SCH(CH$_3$)$_2$ |
| 49 | O | F | Cl | SCH$_2$(CH$_2$)$_2$CH$_3$ |
| 50 | O | F | Cl |  |
| 51 | O | F | Cl | 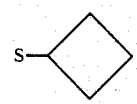 |

TABLE 1-continued

[Structure: bicyclic ring system with N-N, containing C=X, S, and C=N-aryl where aryl has G, A, E substituents]

| No. | X | G | A | E |
|---|---|---|---|---|
| 52 | O | F | Cl | S-cyclopentyl |
| 53 | O | F | Cl | S-cyclohexyl |
| 54 | O | F | Cl | SCH$_2$-cyclopropyl |
| 55 | O | F | Cl | SCH$_2$-cyclobutyl |
| 56 | O | F | Cl | SCH$_2$-cyclopentyl |
| 57 | O | F | Cl | SCH$_2$-cyclohexyl |
| 58 | O | F | Cl | SCH$_2$CH=CH$_2$ |
| 59 | O | F | Cl | SCH$_2$C≡CH |
| 60 | O | F | Cl | SCH$_2$CO$_2$H |
| 61 | O | F | Cl | SCH$_2$CO$_2$CH$_3$ |
| 62 | O | F | Cl | SCH$_2$CO$_2$C$_2$H$_5$ |
| 63 | O | F | Cl | SCH$_2$CO$_2$CH$_2$CH$_2$CH$_3$ |
| 64 | O | F | Cl | SCH$_2$CO$_2$CH(CH$_3$)$_2$ |
| 65 | O | F | Cl | SCH$_2$CO$_2$CH$_2$(CH$_2$)$_2$CH$_3$ |
| 66 | O | F | Cl | SCH$_2$CO$_2$-cyclopropyl |
| 67 | O | F | Cl | SCH$_2$CO$_2$-cyclobutyl |
| 68 | O | F | Cl | SCH$_2$CO$_2$-cyclopentyl |
| 69 | O | F | Cl | SCH$_2$CO$_2$-cyclohexyl |
| 70 | O | F | Cl | SCH$_2$CO$_2$CH$_2$-cyclopropyl |
| 71 | O | F | Cl | SCH$_2$CO$_2$CH$_2$-cyclobutyl |
| 72 | O | F | Cl | SCH$_2$CO$_2$CH$_2$-cyclopentyl |
| 73 | O | F | Cl | SCH$_2$CO$_2$CH$_2$-cyclohexyl |
| 74 | O | F | Cl | SCH$_2$OCH$_3$ |
| 75 | O | F | Cl | SCH$_2$OC$_2$H$_5$ |
| 76 | O | F | Cl | SCH$_2$CH$_2$OCH$_3$ |
| 77 | O | F | Cl | SCH$_2$CH$_2$OC$_2$H$_5$ |
| 78 | O | F | Cl | CO$_2$H |
| 79 | O | F | Cl | CO$_2$CH$_3$ |
| 80 | O | F | Cl | CO$_2$C$_2$H$_5$ |
| 81 | O | F | Cl | CO$_2$CH$_2$CH$_2$CH$_3$ |
| 82 | O | F | Cl | CO$_2$CH(CH$_3$)$_2$ |
| 83 | O | F | Cl | CO$_2$CH$_2$(CH$_2$)$_2$CH$_3$ |
| 84 | O | F | Cl | CO$_2$-cyclopropyl |
| 85 | O | F | Cl | CO$_2$-cyclobutyl |
| 86 | O | F | Cl | CO$_2$-cyclopentyl |
| 87 | O | F | Cl | CO$_2$-cyclohexyl |
| 88 | O | F | Cl | CO$_2$CH$_2$-cyclopropyl |
| 89 | O | F | Cl | CO$_2$CH$_2$-cyclobutyl |
| 90 | O | F | Cl | CO$_2$CH$_2$-cyclopentyl |

TABLE 1-continued

[Structure: bicyclic ring system with N-N, S, and =X group, substituted phenyl with G, A, E substituents]

| No. | X | G | A | E |
|---|---|---|---|---|
| 91 | O | F | Cl | CO₂CH₂-cyclohexyl |
| 92 | O | F | Cl | NHCH₃ |
| 93 | O | F | Cl | NHC₂H₅ |
| 94 | O | F | Cl | NHCH₂CH₂CH₃ |
| 95 | O | F | Cl | NHCH(CH₃)₂ |
| 96 | O | F | Cl | NHCH₂(CH₂)₂CH₃ |
| 97 | O | F | Cl | NH-cyclopropyl |
| 98 | O | F | Cl | NH-cyclobutyl |
| 99 | O | F | Cl | NH-cyclopentyl |
| 100 | O | F | Cl | NH-cyclohexyl |
| 101 | O | F | Cl | NHCH₂-cyclopropyl |
| 102 | O | F | Cl | NHCH₂-cyclobutyl |
| 103 | O | F | Cl | NHCH₂-cyclopentyl |
| 104 | O | F | Cl | NHCH₂-cyclohexyl |
| 105 | O | F | Cl | NHCH₂CH=CH₂ |
| 106 | O | F | Cl | NHCH₂C≡CH |
| 107 | O | F | Cl | CH=N—OH |
| 108 | O | F | Cl | CH=N—OCH₃ |
| 109 | O | F | Cl | CH=N—OC₂H₅ |
| 110 | O | F | Cl | CH=N—OCH₂CH₂CH₃ |
| 111 | O | F | Cl | CH=N—OCH(CH₃)₂ |
| 112 | O | F | Cl | CH=N—OCH₂(CH₂)₂CH₃ |
| 113 | O | F | Cl | CH=N—O-cyclopropyl |
| 114 | O | F | Cl | CH=N—O-cyclobutyl |
| 115 | O | F | Cl | CH=N—O-cyclopentyl |
| 116 | O | F | Cl | CH=N—O-cyclohexyl |
| 117 | O | F | Cl | CH=N—OCH₂-cyclopropyl |
| 118 | O | F | Cl | CH=N—OCH₂-cyclobutyl |
| 119 | O | F | Cl | CH=N—OCH₂-cyclopentyl |
| 120 | O | F | Cl | CH=N—OCH₂-cyclohexyl |
| 121 | O | F | Cl | CH=N—OCH₂CH=CH₂ |
| 122 | O | F | Cl | CH=N—OCH₂C≡CH |
| 123 | S | F | Cl | H |
| 124 | S | F | Cl | CH₃ |
| 125 | S | F | Cl | C₂H₅ |
| 126 | S | F | Cl | F |
| 127 | S | F | Cl | Cl |
| 128 | S | F | Cl | Br |
| 129 | S | F | Cl | C≡N |
| 130 | S | F | Cl | NO₂ |
| 131 | S | F | Cl | NH₂ |
| 132 | S | F | Cl | OH |
| 133 | S | F | Cl | SH |
| 134 | S | F | Cl | OCH₃ |
| 135 | S | F | Cl | OC₂H₅ |
| 136 | S | F | Cl | OCH₂CH₂CH₃ |
| 137 | S | F | Cl | OCH(CH₃)₂ |
| 138 | S | F | Cl | OCH₂(CH₂)₂CH₃ |
| 139 | S | F | Cl |  |

TABLE 1-continued

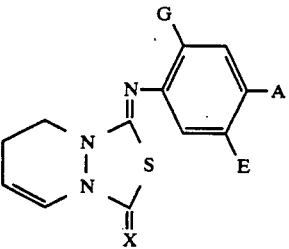

| No. | X | G | A | E |
|---|---|---|---|---|
| 140 | S | F | Cl | 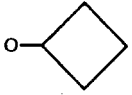 |
| 141 | S | F | Cl | 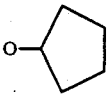 |
| 142 | S | F | Cl | 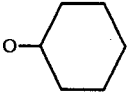 |
| 143 | S | F | Cl | 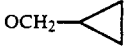 |
| 144 | S | F | Cl | 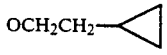 |
| 145 | S | F | Cl | 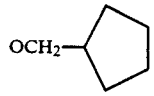 |
| 146 | S | F | Cl | 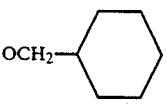 |
| 147 | S | F | Cl | OCH$_2$CH=CH$_2$ |
| 148 | S | F | Cl | OCH$_2$C≡CH |
| 149 | S | F | Cl | OCH$_2$CO$_2$H |
| 150 | S | F | Cl | OCH$_2$CO$_2$CH$_3$ |
| 151 | S | F | Cl | OCH$_2$CO$_2$C$_2$H$_5$ |
| 152 | S | F | Cl | OCH$_2$CO$_2$CH$_2$CH$_2$CH$_3$ |
| 153 | S | F | Cl | OCH$_2$CO$_2$CH(CH$_3$)$_2$ |
| 154 | S | F | Cl | OCH$_2$CO$_2$CH$_2$(CH$_2$)$_2$CH$_3$ |
| 155 | S | F | Cl | 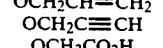 |
| 156 | S | F | Cl | 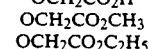 |
| 157 | S | F | Cl | 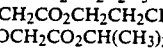 |
| 158 | S | F | Cl | 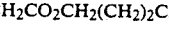 |
| 159 | S | F | Cl | 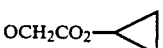 |
| 160 | S | F | Cl |  |
| 161 | S | F | Cl | 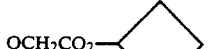 |
| 162 | S | F | Cl | 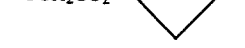 |
| 163 | S | F | Cl | OCH$_2$OCH$_3$ |
| 164 | S | F | Cl | OCH$_2$OC$_2$H$_5$ |
| 165 | S | F | Cl | OCH$_2$CH$_2$OCH$_3$ |
| 166 | S | F | Cl | OCH$_2$CH$_2$OC$_2$H$_5$ |
| 167 | S | F | Cl | SCH$_3$ |
| 168 | S | F | Cl | SC$_2$H$_5$ |
| 169 | S | F | Cl | SCH$_2$CH$_3$ |
| 170 | S | F | Cl | SCH(CH$_3$)$_2$ |
| 171 | S | F | Cl | SCH$_2$(CH$_2$)$_2$CH$_3$ |
| 172 | S | F | Cl | 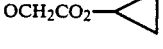 |
| 173 | S | F | Cl | 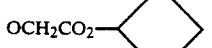 |
| 174 | S | F | Cl |  |
| 175 | S | F | Cl | 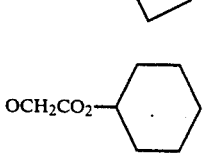 |
| 176 | S | F | Cl | 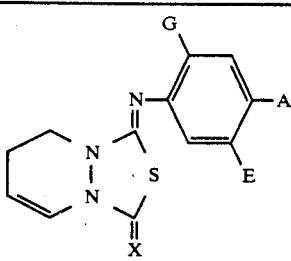 |
| 177 | S | F | Cl | 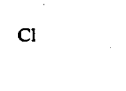 |

TABLE 1-continued

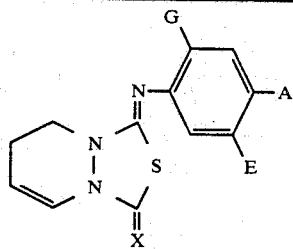

| No. | X | G | A | E |
|---|---|---|---|---|
| 178 | S | F | Cl | SCH₂-cyclopentyl |
| 179 | S | F | Cl | SCH₂-cyclohexyl |
| 180 | S | F | Cl | SCH$_2$CH=CH$_2$ |
| 181 | S | F | Cl | SCH$_2$C≡CH |
| 182 | S | F | Cl | SCH$_2$CO$_2$H |
| 183 | S | F | Cl | SCH$_2$CO$_2$CH$_3$ |
| 184 | S | F | Cl | SCH$_2$CO$_2$C$_2$H$_5$ |
| 185 | S | F | Cl | SCH$_2$CO$_2$CH$_2$CH$_2$CH$_3$ |
| 186 | S | F | Cl | SCH$_2$CO$_2$CH(CH$_3$)$_2$ |
| 187 | S | F | Cl | SCH$_2$CO$_2$CH$_2$(CH$_2$)$_2$CH$_3$ |
| 188 | S | F | Cl | SCH$_2$CO$_2$-cyclopropyl |
| 189 | S | F | Cl | SCH$_2$CO$_2$-cyclobutyl |
| 190 | S | F | Cl | SCH$_2$CO$_2$-cyclopentyl |
| 191 | S | F | Cl | SCH$_2$CO$_2$-cyclohexyl |
| 192 | S | F | Cl | SCH$_2$CO$_2$CH$_2$-cyclopropyl |
| 193 | S | F | Cl | SCH$_2$CO$_2$CH$_2$-cyclobutyl |
| 194 | S | F | Cl | SCH$_2$CO$_2$CH$_2$-cyclopentyl |
| 195 | S | F | Cl | SCH$_2$CO$_2$CH$_2$-cyclohexyl |
| 196 | S | F | Cl | SCH$_2$OCH$_3$ |
| 197 | S | F | Cl | SCH$_2$OC$_2$H$_5$ |
| 198 | S | F | Cl | SCH$_2$CH$_2$OCH$_3$ |

TABLE 1-continued

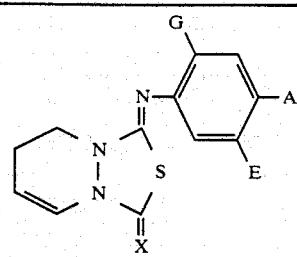

| No. | X | G | A | E |
|---|---|---|---|---|
| 199 | S | F | Cl | SCH$_2$CH$_2$OC$_2$H$_5$ |
| 200 | S | F | Cl | CO$_2$H |
| 201 | S | F | Cl | CO$_2$CH$_3$ |
| 202 | S | F | Cl | CO$_2$C$_2$H$_5$ |
| 203 | S | F | Cl | CO$_2$CH$_2$CH$_2$CH$_3$ |
| 204 | S | F | Cl | CO$_2$CH(CH$_3$)$_2$ |
| 205 | S | F | Cl | CO$_2$CH$_2$(CH$_2$)$_2$CH$_3$ |
| 206 | S | F | Cl | CO$_2$-cyclopropyl |
| 207 | S | F | Cl | CO$_2$-cyclobutyl |
| 208 | S | F | Cl | CO$_2$-cyclopentyl |
| 209 | S | F | Cl | CO$_2$-cyclohexyl |
| 210 | S | F | Cl | CO$_2$CH$_2$-cyclopropyl |
| 211 | S | F | Cl | CO$_2$CH$_2$-cyclobutyl |
| 212 | S | F | Cl | CO$_2$CH$_2$-cyclopentyl |
| 213 | S | F | Cl | CO$_2$CH$_2$-cyclohexyl |
| 214 | S | F | Cl | NHCH$_3$ |
| 215 | S | F | Cl | NHC$_2$H$_5$ |
| 216 | S | F | Cl | NHCH$_2$CH$_2$CH$_3$ |
| 217 | S | F | Cl | NHCH(CH$_3$)$_2$ |
| 218 | S | F | Cl | NHCH$_2$(CH$_2$)$_2$CH$_3$ |
| 219 | S | F | Cl | NH-cyclopropyl |
| 220 | S | F | Cl | NH-cyclobutyl |

TABLE 1-continued

[Structure: bicyclic ring system with G, A, E substituents on phenyl ring attached via N to the ring system containing X]

| No. | X | G | A | E |
|---|---|---|---|---|
| 221 | S | F | Cl | NH-cyclopentyl |
| 222 | S | F | Cl | NH-cyclohexyl |
| 223 | S | F | Cl | NHCH₂-cyclopropyl |
| 224 | S | F | Cl | NHCH₂-cyclobutyl |
| 225 | S | F | Cl | NHCH₂-cyclopentyl |
| 226 | S | F | Cl | NHCH₂-cyclohexyl |
| 227 | S | F | Cl | NHCH$_2$CH=CH$_2$ |
| 228 | S | F | Cl | NHCH$_2$C≡CH |
| 229 | S | F | Cl | CH=N—OH |
| 230 | S | F | Cl | CH=N—OCH$_3$ |
| 231 | S | F | Cl | CH=N—OC$_2$H$_5$ |
| 232 | S | F | Cl | CH=N—OCH$_2$CH$_2$CH$_3$ |
| 233 | S | F | Cl | CH=N—OCH(CH$_3$)$_2$ |
| 234 | S | F | Cl | CH=N—OCH$_2$(CH$_2$)$_2$CH$_3$ |
| 235 | S | F | Cl | CH=N—O-cyclopropyl |
| 236 | S | F | Cl | CH=N—O-cyclobutyl |
| 237 | S | F | Cl | CH=N—O-cyclopentyl |
| 238 | S | F | Cl | CH=N—O-cyclohexyl |
| 239 | S | F | Cl | CH=N—OCH$_2$-cyclopropyl |
| 240 | S | F | Cl | CH=N—OCH$_2$-cyclobutyl |
| 241 | S | F | Cl | CH=N—OCH$_2$-cyclopentyl |
| 242 | S | F | Cl | CH=N—OCH$_2$-cyclohexyl |
| 243 | S | F | Cl | CH=N—OCH$_2$CH=CH$_2$ |
| 244 | S | F | Cl | CH=N—OCH$_2$C≡CH |
| 245 | O | H | Cl | SCH$_2$CO$_2$-cyclopentyl |
| 246 | O | H | Cl | OCH$_2$C≡CH |
| 247 | O | H | Br | OCH(CH$_3$)$_2$ |
| 248 | O | H | Br | CO$_2$C$_2$H$_5$ |
| 249 | O | H | I | CH=N—OCH$_3$ |
| 250 | O | Cl | Cl | NHCH$_2$-cyclohexyl |
| 251 | O | Cl | Br | OCH$_2$OCH$_3$ |
| 252 | O | Cl | I | SCH(CH$_3$)$_2$ |
| 253 | O | Br | Cl | OCH$_2$CO$_2$-cyclopentyl |
| 254 | O | Br | Br | SCH$_2$C≡CH |
| 255 | O | Br | I | CH=N—OCH$_2$C≡CH |
| 256 | O | I | Cl | OCH$_2$CH=CH$_2$ |
| 257 | O | I | Br | SCH$_2$CH=CH$_2$ |
| 258 | O | I | I | C≡N |
| 259 | S | H | Cl | SCH$_2$CO$_2$-cyclopentyl |
| 260 | S | H | Cl | OCH$_2$C≡CH |
| 261 | S | H | Br | OCH(CH$_3$)$_2$ |
| 262 | S | H | Br | CO$_2$C$_2$H$_5$ |
| 263 | S | H | I | CH=N—OCH$_3$ |

TABLE 1-continued

Structure (left, Nos. 264–302): G and A on benzene ring with N= linkage to bicyclic N-N-S ring with =X; E substituent at position shown.

| No. | X | G | A | E |
|---|---|---|---|---|
| 264 | S | Cl | Cl | NHCH₂-cyclohexyl |
| 265 | S | Cl | Br | OCH₂OCH₃ |
| 266 | S | Cl | I | SCH(CH₃)₂ |
| 267 | S | Br | Cl | OCH₂CO₂-cyclopentyl |
| 268 | S | Br | Br | SCH₂C≡CH |
| 269 | S | Br | I | CH=N—OCH₂C≡CH |
| 270 | S | I | Cl | OCH₂CH=CH₂ |
| 271 | S | I | Br | SCH₂CH=CH₂ |
| 272 | S | I | I | C≡N |
| 273 | O | H | Cl | OCH(CH₃)₂ |
| 274 | O | H | Cl | SCH₂C≡CH |
| 275 | O | H | Cl | SCH₂CO₂H |
| 276 | O | H | Cl | SCH₂CO₂CH₃ |
| 277 | O | H | Cl | SCH₂CO₂C₂H₅ |
| 278 | O | H | Cl | SCH₂CO₂CH(CH₃)₂ |
| 279 | O | H | Cl | SCH₂CO₂CH₂(CH₂)₂CH₃ |
| 280 | O | H | Cl | SCH₂CO₂-cyclopentyl |
| 281 | O | H | Cl | SCH(CH₃)CO₂CH₃ |
| 282 | O | H | Cl | SCH(CH₃)CO₂C₂H₅ |
| 283 | O | H | Cl | SCH₂C(O)N(CH₃)₂ |
| 284 | O | H | Cl | SCH₂C(O)N(C₂H₅)₂ |
| 285 | O | H | Cl | SH |
| 286 | O | H | Cl | OH |
| 287 | O | H | Cl | CO₂H |
| 288 | O | H | Cl | tetrahydropyran-2-ylthio (S-CH in tetrahydropyran with O) |
| 289 | O | H | Cl | OCH₂CO₂H |
| 290 | O | H | Cl | OCH₂CO₂CH₃ |
| 291 | O | H | Cl | OCH₂CO₂C₂H₅ |
| 292 | O | H | Cl | OCH(CH₃)CO₂CH₃ |
| 293 | O | H | Cl | OCH(CH₃)CO₂C₂H₅ |
| 294 | O | H | Cl | SCH(C₂H₅)CO₂CH₃ |
| 295 | O | H | Cl | SCH(C₂H₅)C(O)N-piperidinyl |
| 296 | O | H | Cl | SCH(CH₃)C(O)N(CH₃)₂ |
| 297 | O | H | Cl | OCH₂C(CH₃)=NOCH₃ |
| 298 | O | H | Cl | SCH₂C≡N |
| 299 | O | H | Cl | SCH₂CO₂CH(CH₃)CO₂CH₃ |
| 300 | O | H | Cl | SCH₂CO₂CH₂C≡CH |
| 301 | O | H | Cl | CO₂CH₃ |
| 302 | O | H | Cl | CO₂C₂H₅ |

| No. | X | G | A | E |
|---|---|---|---|---|
| 303 | O | H | Cl | CO₂-cyclopentyl |
| 304 | O | H | Cl | SCH₂CO₂CH₂CH₂OCH₃ |
| 305 | S | H | Cl | OCH(CH₃)₂ |
| 306 | S | H | Cl | SCH₂C≡CH |
| 307 | S | H | Cl | SCH₂CO₂H |
| 308 | S | H | Cl | SCH₂CO₂CH₃ |
| 309 | S | H | Cl | SCH₂CO₂C₂H₅ |
| 310 | S | H | Cl | SCH₂CO₂CH(CH₃)₂ |
| 311 | S | H | Cl | SCH₂CO₂CH₂(CH₂)₂CH₃ |
| 312 | S | H | Cl | SCH₂CO₂-cyclopentyl |
| 313 | S | H | Cl | SCH(CH₃)CO₂CH₃ |
| 314 | S | H | Cl | SCH(CH₃)CO₂C₂H₅ |
| 315 | S | H | Cl | SCH₂C(O)N(CH₃)₂ |
| 316 | S | H | Cl | SCH₂C(O)N(C₂H₅)₂ |
| 317 | S | H | Cl | SH |
| 318 | S | H | Cl | OH |
| 319 | S | H | Cl | CO₂H |
| 320 | S | H | Cl | tetrahydropyran-2-ylthio |
| 321 | S | H | Cl | OCH₂CO₂H |
| 322 | S | H | Cl | OCH₂CO₂CH₃ |
| 323 | S | H | Cl | OCH₂CO₂C₂H₅ |
| 324 | S | H | Cl | OCH(CH₃)CO₂CH₃ |
| 325 | S | H | Cl | OCH(CH₃)CO₂C₂H₅ |
| 326 | S | H | Cl | SCH(C₂H₅)CO₂CH₃ |
| 327 | S | H | Cl | SCH(C₂H₅)C(O)N-piperidinyl |
| 328 | S | H | Cl | SCH(CH₃)C(O)N(CH₃)₂ |
| 329 | S | H | Cl | OCH₂C(CH₃)=NOCH₃ |
| 330 | S | H | Cl | SCH₂C≡N |
| 331 | S | H | Cl | SCH₂CO₂CH(CH₃)CO₂CH₃ |
| 332 | S | H | Cl | SCH₂CO₂CH₂C≡CH |
| 333 | S | H | Cl | CO₂CH₃ |
| 334 | S | H | Cl | CO₂C₂H₅ |
| 335 | S | H | Cl | CO₂-cyclopentyl |
| 336 | S | H | Cl | SCH₂CO₂CH₂CH₂OCH₃ |
| 337 | O | Cl | Cl | OCH(CH₃)₂ |
| 338 | O | Cl | Cl | SCH₂C≡CH |
| 339 | O | Cl | Cl | SCH₂CO₂H |
| 340 | O | Cl | Cl | SCH₂CO₂CH₃ |
| 341 | O | Cl | Cl | SCH₂CO₂C₂H₅ |
| 342 | O | Cl | Cl | SCH₂CO₂CH(CH₃)₂ |
| 343 | O | Cl | Cl | SCH₂CO₂CH₂(CH₂)₂CH₃ |

TABLE 1-continued

[Structure: bicyclic compound with G, A, E, X substituents on phenyl-imine-thiazolidinone fused with tetrahydropyridazine containing C=C]

| No. | X | G | A | E |
|---|---|---|---|---|
| 344 | O | Cl | Cl | SCH₂CO₂-cyclopentyl |
| 345 | O | Cl | Cl | SCH(CH₃)CO₂CH₃ |
| 346 | O | Cl | Cl | SCH(CH₃)CO₂C₂H₅ |
| 347 | O | Cl | Cl | SCH₂C(O)N(CH₃)₂ |
| 348 | O | Cl | Cl | SCH₂C(O)N(C₂H₅)₂ |
| 349 | O | Cl | Cl | SH |
| 350 | O | Cl | Cl | OH |
| 351 | O | Cl | Cl | CO₂H |
| 352 | O | Cl | Cl | S-tetrahydropyran-2-yl |
| 353 | O | Cl | Cl | OCH₂CO₂H |
| 354 | O | Cl | Cl | OCH₂CO₂CH₃ |
| 355 | O | Cl | Cl | OCH₂CO₂C₂H₅ |
| 356 | O | Cl | Cl | OCH(CH₃)CO₂CH₃ |
| 357 | O | Cl | Cl | OCH(CH₃)CO₂C₂H₅ |
| 358 | O | Cl | Cl | SCH(C₂H₅)CO₂CH₃ |
| 359 | O | Cl | Cl | SCH(C₂H₅)C(O)N-piperidinyl |
| 360 | O | Cl | Cl | SCH(CH₃)C(O)N(CH₃)₂ |
| 361 | O | Cl | Cl | OCH₂C(CH₃)=NOCH₃ |
| 362 | O | Cl | Cl | SCH₂C≡N |
| 363 | O | Cl | Cl | SCH₂CO₂CH(CH₃)CO₂CH₃ |
| 364 | O | Cl | Cl | SCH₂CO₂CH₂C≡CH |
| 365 | O | Cl | Cl | CO₂CH₃ |
| 366 | O | Cl | Cl | CO₂C₂H₅ |
| 367 | O | Cl | Cl | CO₂-cyclopentyl |
| 368 | O | Cl | Cl | SCH₂CO₂CH₂CH₂OCH₃ |
| 369 | S | Cl | Cl | OCH(CH₃)₂ |
| 370 | S | Cl | Cl | SCH₂C≡CH |
| 371 | S | Cl | Cl | SCH₂CO₂H |
| 372 | S | Cl | Cl | SCH₂CO₂CH₃ |
| 373 | S | Cl | Cl | SCH₂CO₂C₂H₅ |
| 374 | S | Cl | Cl | SCH₂CO₂CH(CH₃)₂ |
| 375 | S | Cl | Cl | SCH₂CO₂CH₂(CH₂)₂CH₃ |
| 376 | S | Cl | Cl | SCH₂CO₂-cyclopentyl |
| 377 | S | Cl | Cl | SCH(CH₃)CO₂CH₃ |
| 378 | S | Cl | Cl | SCH(CH₃)CO₂C₂H₅ |
| 379 | S | Cl | Cl | SCH₂C(O)N(CH₃)₂ |
| 380 | S | Cl | Cl | SCH₂C(O)N(C₂H₅)₂ |
| 381 | S | Cl | Cl | SH |
| 382 | S | Cl | Cl | OH |
| 383 | S | Cl | Cl | CO₂H |
| 384 | S | Cl | Cl | S-tetrahydropyran-2-yl |
| 385 | S | Cl | Cl | OCH₂CO₂H |
| 386 | S | Cl | Cl | OCH₂CO₂CH₃ |
| 387 | S | Cl | Cl | OCH₂CO₂C₂H₅ |
| 388 | S | Cl | Cl | OCH(CH₃)CO₂CH₃ |
| 389 | S | Cl | Cl | OCH(CH₃)CO₂C₂H₅ |
| 390 | S | Cl | Cl | SCH(C₂H₅)CO₂CH₃ |
| 391 | S | Cl | Cl | SCH(C₂H₅)C(O)N-piperidinyl |
| 392 | S | Cl | Cl | SCH(CH₃)C(O)N(CH₃)₂ |
| 393 | S | Cl | Cl | OCH₂C(CH₃)=NOCH₃ |
| 394 | S | Cl | Cl | SCH₂C≡N |
| 395 | S | Cl | Cl | SCH₂CO₂CH(CH₃)CO₂CH₃ |
| 396 | S | Cl | Cl | SCH₂CO₂CH₂C≡CH |
| 397 | S | Cl | Cl | CO₂CH₃ |
| 398 | S | Cl | Cl | CO₂C₂H₅ |
| 399 | S | Cl | Cl | CO₂-cyclopentyl |
| 400 | S | Cl | Cl | SCH₂CO₂CH₂CH₂OCH₃ |
| 401 | O | F | Br | OCH(CH₃)₂ |
| 402 | O | F | Br | SCH₂C≡CH |
| 403 | O | F | Br | SCH₂CO₂H |
| 404 | O | F | Br | SCH₂CO₂CH₃ |
| 405 | O | F | Br | SCH₂CO₂C₂H₅ |
| 406 | O | F | Br | SCH₂CO₂CH(CH₃)₂ |
| 407 | O | F | Br | SCH₂CO₂CH₂(CH₂)₂CH₃ |
| 408 | O | F | Br | SCH₂CO₂-cyclopentyl |
| 409 | O | F | Br | SCH(CH₃)CO₂CH₃ |
| 410 | O | F | Br | SCH(CH₃)CO₂C₂H₅ |
| 411 | O | F | Br | SCH₂C(O)N(CH₃)₂ |
| 412 | O | F | Br | SCH₂C(O)N(C₂H₅)₂ |
| 413 | O | F | Br | SH |
| 414 | O | F | Br | OH |
| 415 | O | F | Br | CO₂H |
| 416 | O | F | Br | S-tetrahydropyran-2-yl |
| 417 | O | F | Br | OCH₂CO₂H |
| 418 | O | F | Br | OCH₂CO₂CH₃ |
| 419 | O | F | Br | OCH₂CO₂C₂H₅ |
| 420 | O | F | Br | OCH(CH₃)CO₂CH₃ |
| 422 | O | F | Br | SCH(C₂H₅)CO₂CH₃ |

TABLE 1-continued

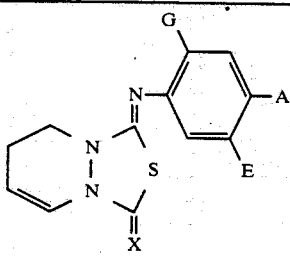

| No. | X | G | A | E |
|---|---|---|---|---|
| 423 | O | F | Br | |
| | | | | SCH(C$_2$H$_5$)C(O)N⟨piperidine⟩ |
| 424 | O | F | Br | SCH(CH$_3$)C(O)N(CH$_3$)$_2$ |
| 421 | O | F | Br | OCH(CH$_3$)CO$_2$C$_2$H$_5$ |
| 425 | O | F | Br | OCH$_2$C(CH$_3$)=NOCH$_3$ |
| 426 | O | F | Br | SCH$_2$C≡N |
| 427 | O | F | Br | SCH$_2$CO$_2$CH(CH$_3$)CO$_2$CH$_3$ |
| 428 | O | F | Br | SCH$_2$CO$_2$CH$_2$C≡CH |
| 429 | O | F | Br | CO$_2$CH$_3$ |
| 430 | O | F | Br | CO$_2$C$_2$H$_5$ |
| 431 | O | F | Br | CO$_2$–⟨cyclopentyl⟩ |
| 432 | O | F | Br | SCH$_2$CO$_2$CH$_2$CH$_2$OCH$_3$ |
| 433 | S | F | Br | OCH(CH$_3$)$_2$ |
| 434 | S | F | Br | SCH$_2$C≡CH |
| 435 | S | F | Br | SCH$_2$CO$_2$H |
| 436 | S | F | Br | SCH$_2$CO$_2$CH$_3$ |
| 437 | S | F | Br | SCH$_2$CO$_2$C$_2$H$_5$ |
| 438 | S | F | Br | SCH$_2$CO$_2$CH(CH$_3$)$_2$ |
| 439 | S | F | Br | SCH$_2$CO$_2$CH$_2$(CH$_2$)$_2$CH$_3$ |
| 440 | S | F | Br | SCH$_2$CO$_2$–⟨cyclopentyl⟩ |
| 441 | S | F | Br | SCH(CH$_3$)CO$_2$CH$_3$ |
| 442 | S | F | Br | SCH(CH$_3$)CO$_2$C$_2$H$_5$ |
| 443 | S | F | Br | SCH$_2$C(O)N(CH$_3$)$_2$ |
| 444 | S | F | Br | SCH$_2$C(O)N(C$_2$H$_5$)$_2$ |
| 445 | S | F | Br | SH |
| 446 | S | F | Br | OH |
| 447 | S | F | Br | CO$_2$H |
| 448 | S | F | Br | ⟨tetrahydropyran-2-ylthio⟩ |
| 449 | S | F | Br | OCH$_2$CO$_2$H |
| 450 | S | F | Br | OCH$_2$CO$_2$CH$_3$ |
| 451 | S | F | Br | OCH$_2$CO$_2$C$_2$H$_5$ |
| 452 | S | F | Br | OCH(CH$_3$)CO$_2$CH$_3$ |
| 453 | S | F | Br | OCH(CH$_3$)CO$_2$C$_2$H$_5$ |
| 454 | S | F | Br | SCH(C$_2$H$_5$)CO$_2$CH$_3$ |
| 455 | S | F | Br | SCH(C$_2$H$_5$)C(O)N⟨piperidine⟩ |
| 456 | S | F | Br | SCH(CH$_3$)C(O)N(CH$_3$)$_2$ |
| 457 | S | F | Br | OCH$_2$C(CH$_3$)=NOCH$_3$ |
| 458 | S | F | Br | SCH$_2$C≡N |
| 459 | S | F | Br | SCH$_2$CO$_2$CH(CH$_3$)CO$_2$CH$_3$ |
| 460 | S | F | Br | SCH$_2$CO$_2$CH$_2$C≡CH |
| 461 | S | F | Br | CO$_2$CH$_3$ |
| 462 | S | F | Br | CO$_2$C$_2$H$_5$ |

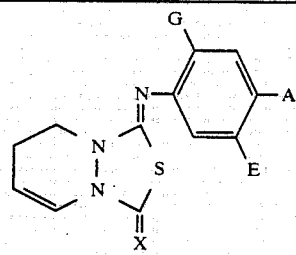

| No. | X | G | A | E |
|---|---|---|---|---|
| 463 | S | F | Br | CO$_2$–⟨cyclopentyl⟩ |
| 464 | S | F | Br | SCH$_2$CO$_2$CH$_2$CH$_2$OCH$_3$ |
| 465 | O | F | NO$_2$ | OCH(CH$_3$)$_2$ |
| 466 | O | F | NO$_2$ | SCH$_2$C≡CH |
| 467 | O | F | NO$_2$ | SCH$_2$CO$_2$H |
| 468 | O | F | NO$_2$ | SCH$_2$CO$_2$CH$_3$ |
| 469 | O | F | NO$_2$ | SCH$_2$CO$_2$C$_2$H$_5$ |
| 470 | O | F | NO$_2$ | SCH$_2$CO$_2$CH(CH$_3$)$_2$ |
| 471 | O | F | NO$_2$ | SCH$_2$CO$_2$CH$_2$(CH$_2$)$_3$CH$_3$ |
| 472 | O | F | NO$_2$ | SCH$_2$CO$_2$–⟨cyclopentyl⟩ |
| 473 | O | F | NO$_2$ | SCH(CH$_3$)CO$_2$CH$_3$ |
| 474 | O | F | NO$_2$ | SCH(CH$_3$)CO$_2$C$_2$H$_5$ |
| 475 | O | F | NO$_2$ | SCH$_2$C(O)N(CH$_3$)$_2$ |
| 476 | O | F | NO$_2$ | SCH$_2$C(O)N(C$_2$H$_5$)$_2$ |
| 477 | O | F | NO$_2$ | SH |
| 478 | O | F | NO$_2$ | OH |
| 479 | O | F | NO$_2$ | CO$_2$H |
| 480 | O | F | NO$_2$ | ⟨tetrahydropyran-2-ylthio⟩ |
| 481 | O | F | NO$_2$ | OCH$_2$CO$_2$H |
| 482 | O | F | NO$_2$ | OCH$_2$CO$_2$CH$_3$ |
| 483 | O | F | NO$_2$ | OCH$_2$CO$_2$C$_2$H$_5$ |
| 484 | O | F | NO$_2$ | OCH(CH$_3$)CO$_2$CH$_3$ |
| 485 | O | F | NO$_2$ | OCH(CH$_3$)CO$_2$C$_2$H$_5$ |
| 486 | O | F | NO$_2$ | SCH(C$_2$H$_5$)CO$_2$CH$_3$ |
| 487 | O | F | NO$_2$ | SCH(C$_2$H$_5$)C(O)N⟨piperidine⟩ |
| 488 | O | F | NO$_2$ | SCH(CH$_3$)C(O)N(CH$_3$)$_2$ |
| 489 | O | F | NO$_2$ | OCH$_2$C(CH$_3$)=NOCH$_3$ |
| 490 | O | F | NO$_2$ | SCH$_2$C≡N |
| 491 | O | F | NO$_2$ | SCH$_2$CO$_2$CH(CH$_3$)CO$_2$CH$_3$ |
| 492 | O | F | NO$_2$ | SCH$_2$CO$_2$CH$_2$C≡CH |
| 493 | O | F | NO$_2$ | CO$_2$CH$_3$ |
| 494 | O | F | NO$_2$ | CO$_2$C$_2$H$_5$ |
| 495 | O | F | NO$_2$ | CO$_2$–⟨cyclopentyl⟩ |
| 496 | O | F | NO$_2$ | SCH$_2$CO$_2$CH$_2$CH$_2$OCH$_3$ |
| 497 | S | F | NO$_2$ | OCH(CH$_3$)$_2$ |
| 498 | S | F | NO$_2$ | SCH$_2$C≡CH |
| 499 | S | F | NO$_2$ | SCH$_2$CO$_2$H |
| 500 | S | F | NO$_2$ | SCH$_2$CO$_2$CH$_3$ |
| 501 | S | F | NO$_2$ | SCH$_2$CO$_2$C$_2$H$_5$ |
| 502 | S | F | NO$_2$ | SCH$_2$CO$_2$CH(CH$_3$)$_2$ |
| 503 | S | F | NO$_2$ | SCH$_2$CO$_2$CH$_2$(CH$_2$)$_2$CH$_3$ |

TABLE 1-continued

[Structure: bicyclic ring system with G and A substituents on phenyl ring, N=C linkage, S, E group, and X substituent]

| No. | X | G | A | E |
|---|---|---|---|---|
| 504 | S | F | NO₂ | SCH₂CO₂-cyclopentyl |
| 505 | S | F | NO₂ | SCH(CH₃)CO₂CH₃ |
| 506 | S | F | NO₂ | SCH(CH₃)CO₂C₅H₅ |
| 507 | S | F | NO₂ | SCH₂C(O)N(CH₃)₂ |
| 508 | S | F | NO₂ | SCH₂C(O)N(C₂H₅)₂ |
| 509 | S | F | NO₂ | SH |
| 510 | S | F | NO₂ | OH |
| 511 | S | F | NO₂ | CO₂H |
| 512 | S | F | NO₂ | S-(tetrahydropyran-2-yl) |
| 513 | S | F | NO₂ | OCH₂CO₂H |
| 514 | S | F | NO₂ | OCH₂CO₂CH₃ |
| 515 | S | F | NO₂ | OCH₂CO₂C₂H₅ |
| 516 | S | F | NO₂ | OCH(CH₃)CO₂CH₃ |
| 517 | S | F | NO₂ | OCH(CH₃)CO₂C₂H₅ |
| 518 | S | F | NO₂ | SCH(C₂H₅)CO₂CH₃ |
| 519 | S | F | NO₂ | SCH(C₂H₅)C(O)N(piperidinyl) |
| 520 | S | F | NO₂ | SCH(CH₃)C(O)N(CH₃)₂ |
| 521 | S | F | NO₂ | OCH₂C(CH₃)=NOCH₃ |
| 522 | S | F | NO₂ | SCH₂C≡N |
| 523 | S | F | NO₂ | SCH₂CO₂CH(CH₃)CO₂CH₃ |
| 524 | S | F | NO₂ | SCH₂CO₂CH₂C≡CH |
| 525 | S | F | NO₂ | CO₂CH₃ |
| 526 | S | F | NO₂ | CO₂C₂H₅ |
| 527 | S | F | NO₂ | CO₂-cyclopentyl |
| 528 | S | F | NO₂ | SCH₂CO₂CH₂CH₂OCH₃ |
| 529 | O | H | Cl | NH₂ |
| 530 | S | H | Cl | NH₂ |
| 531 | O | H | Cl | C≡N |
| 532 | S | H | Cl | C≡N |
| 533 | O | H | Cl | S-(γ-butyrolactone-α-yl) |
| 534 | S | H | Cl | S-(γ-butyrolactone-α-yl) |
| 535 | O | H | Cl | OCH₂CH₂OCH₃ |
| 536 | S | H | Cl | OCH₂CH₂OCH₃ |
| 537 | O | H | Cl | OCH₂C≡N |
| 538 | S | H | Cl | OCH₂C≡N |
| 539 | O | H | Cl | O-(tetrahydropyran-2-yl) |
| 540 | S | H | Cl | O-(tetrahydropyran-2-yl) |
| 541 | O | H | Cl | OCH₂CON(CH₃)₂ |
| 542 | S | H | Cl | OCH₂CON(CH₃)₂ |
| 543 | O | H | Cl | SCH(CH₃)CO₂-cyclopentyl |
| 544 | S | H | Cl | SCH(CH₃)CO₂-cyclopentyl |
| 545 | O | Cl | Cl | NH₂ |
| 546 | S | Cl | Cl | NH₂ |
| 547 | O | Cl | Cl | C≡N |
| 548 | S | Cl | Cl | C≡N |
| 549 | O | Cl | Cl | S-(γ-butyrolactone-α-yl) |
| 550 | S | Cl | Cl | S-(γ-butyrolactone-α-yl) |
| 551 | O | Cl | Cl | OCH₂CH₂OCH₃ |
| 552 | S | Cl | Cl | OCH₂CH₂OCH₃ |
| 553 | O | Cl | Cl | OCH₂C≡N |
| 554 | S | Cl | Cl | OCH₂C≡N |
| 555 | O | Cl | Cl | O-(tetrahydropyran-2-yl) |
| 556 | S | Cl | Cl | O-(tetrahydropyran-2-yl) |
| 557 | O | Cl | Cl | OCH₂CON(CH₃)₂ |
| 558 | S | Cl | Cl | OCH₂CON(CH₃)₂ |

TABLE 1-continued

| No. | X | G | A | E |
|---|---|---|---|---|
| 559 | O | Cl | Cl | SCH(CH$_3$)CO$_2$-cyclopentyl |
| 560 | S | Cl | Cl | SCH(CH$_3$)CO$_2$-cyclopentyl |
| 561 | O | F | Cl | OCH$_2$C≡N |
| 562 | O | F | Cl | 2-tetrahydropyranyloxy (O in ring) |
| 563 | O | F | Cl | 2-(tetrahydrothiopyranyl)oxy |
| 564 | O | F | Cl | OCH$_2$CO$_2$CH(CH$_3$)CO$_2$CH$_3$ |
| 565 | O | F | Cl | OCH$_2$CO$_2$CH(CH$_3$)CO$_2$C$_2$H$_5$ |
| 566 | O | F | Cl | OCH$_2$CO$_2$C(CH$_3$)$_3$ |
| 567 | O | F | Cl | OCH$_2$CON(CH$_3$)$_2$ |
| 568 | O | F | Cl | OCH$_2$CON(C$_2$H$_5$)$_2$ |
| 569 | O | F | Cl | OCH$_2$CON(piperidinyl) |
| 570 | O | F | Cl | OCH(CH$_3$)CO$_2$CH$_3$ |
| 571 | O | F | Cl | OCH(CH$_3$)CO$_2$C$_2$H$_5$ |
| 572 | O | F | Cl | OCH(CH$_3$)CO$_2$-cyclopentyl |
| 573 | O | F | Cl | OCH(CH$_3$)CON(CH$_3$)$_2$ |
| 574 | O | F | Cl | OCH(C$_2$H$_5$)CO$_2$CH$_3$ |
| 575 | O | F | Cl | OCH(C$_2$H$_5$)CON(CH$_3$)$_2$ |
| 576 | O | F | Cl | OCH(C$_2$H$_5$)CON(piperidinyl) |
| 577 | O | F | Cl | OCH$_2$COCH$_3$ |
| 578 | O | F | Cl | OCH$_2$COC$_2$H$_5$ |
| 579 | O | F | Cl | OCH$_2$C(CH$_3$)=NOH |
| 580 | O | F | Cl | OCH$_2$C(CH$_3$)=NOCH$_3$ |
| 581 | O | F | Cl | OCH$_2$C(CH$_3$)=NOC$_2$H$_5$ |
| 582 | O | F | Cl | OCH$_2$C(CH$_3$)=NOCOCH$_3$ |
| 583 | O | F | Cl | OCH$_2$-C(CH$_3$)(1,3-dioxolan-2-yl) |
| 584 | O | F | Cl | OCH$_2$-C(CH$_3$)(1,3-dithiolan-2-yl) |
| 585 | O | F | Cl | (tetrahydrofuran-2-one-3-yl)oxy |
| 586 | O | F | Cl | OCH(CH(CH$_3$)$_2$)CO$_2$CH$_3$ |
| 587 | O | F | Cl | OCH$_2$CO$_2$CH$_2$CH$_2$OCH$_3$ |
| 588 | O | F | Cl | OCH$_2$CO$_2$CH$_2$CH=CH$_2$ |
| 589 | O | F | Cl | OCH$_2$CO$_2$CH$_2$C≡CH |
| 590 | O | F | Cl | OCH$_2$CO$_2$CH$_2$CH$_2$Cl |
| 591 | O | F | Cl | OCH$_2$CO$_2$CH$_2$CF$_3$ |
| 592 | O | F | Cl | OCH$_2$C(O)SCH$_3$ |
| 593 | O | F | Cl | OCH$_2$C(O)SC$_2$H$_5$ |
| 594 | O | F | Cl | OCH$_2$C(O)S-cyclopentyl |
| 595 | O | F | Cl | OCH$_2$CS$_2$CH$_3$ |
| 596 | O | F | Cl | OCH(CH$_3$)C(O)SCH$_3$ |
| 597 | O | F | Cl | OCH(CH$_3$)C(O)SC$_2$H$_5$ |
| 598 | O | F | Cl | OCH(C$_2$H$_5$)C(O)SCH$_3$ |
| 599 | O | F | Cl | OCH(C$_2$H$_5$)C(O)SC$_2$H$_5$ |
| 600 | O | F | Cl | OCH$_2$CSN(CH$_3$)$_2$ |
| 601 | O | F | Cl | OCH$_2$CSN(C$_2$H$_5$)$_2$ |
| 602 | O | F | Cl | OCH$_2$CSN(piperidinyl) |
| 603 | O | F | Cl | OCH(CH$_3$)CSN(CH$_3$)$_2$ |
| 604 | O | F | Cl | OCH(CH(CH$_3$)$_2$)C(O)SCH$_3$ |
| 605 | O | F | Cl | OCH(CH$_2$CH$_2$CH$_3$)CO$_2$H |
| 606 | O | F | Cl | SCH$_2$C≡N |
| 607 | O | F | Cl | 2-(tetrahydropyranyl)thio |
| 608 | O | F | Cl | 2-(tetrahydrothiopyranyl)thio |
| 609 | O | F | Cl | SCH$_2$CO$_2$C(CH$_3$)$_3$ |
| 610 | O | F | Cl | SCH$_2$CO$_2$CH$_2$CO$_2$CH$_3$ |
| 611 | O | F | Cl | SCH$_2$CO$_2$CH$_2$CO$_2$C$_2$H$_5$ |
| 612 | O | F | Cl | SCH$_2$CO$_2$CH(CH$_3$)CO$_2$CH$_3$ |
| 613 | O | F | Cl | SCH$_2$CO$_2$CH(CH$_3$)CO$_2$C$_2$H$_5$ |
| 614 | O | F | Cl | SCH$_2$CO$_2$CH$_2$CH$_2$Cl |
| 615 | O | F | Cl | SCH$_2$CO$_2$CH$_2$CH$_2$Br |
| 616 | O | F | Cl | SCH$_2$CO$_2$CH$_2$CF$_3$ |
| 617 | O | F | Cl | SCH$_2$CO$_2$CH$_2$CH=CH$_2$ |
| 618 | O | F | Cl | SCH$_2$CO$_2$CH$_2$C≡CH |
| 619 | O | F | Cl | SCH$_2$CO$_2$CH(CH$_3$)C≡CH |
| 620 | O | F | Cl | SCH$_2$CO$_2$CH$_2$CH$_2$OCH$_3$ |

TABLE 1-continued

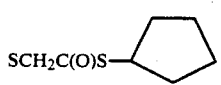

| No. | X | G | A | E |
|---|---|---|---|---|
| 621 | O | F | Cl | SCH₂CO₂CH₂CH₂OC₂H₅ |
| 622 | O | F | Cl | SCH₂C(O)SCH₃ |
| 623 | O | F | Cl | SCH₂C(O)SC₂H₅ |
| 624 | O | F | Cl | SCH₂CS₂CH₃ |
| 625 | O | F | Cl | SCH₂C(O)S-cyclopentyl |
| 626 | O | F | Cl | SCH₂CON(CH₃)₂ |
| 627 | O | F | Cl | SCH₂CON(C₂H₅)₂ |
| 628 | O | F | Cl | SCH₂CONH(CH₃) |
| 629 | O | F | Cl | SCH₂CONH(C₂H₅) |
| 630 | O | F | Cl | SCH₂CON-piperidinyl |
| 631 | O | F | Cl | SCH₂CSN(CH₃)₂ |
| 632 | O | F | Cl | SCH₂CSN(C₂H₅)₂ |
| 633 | O | F | Cl | SCH₂CSN-piperidinyl |
| 634 | O | F | Cl | SCH₂CONHCH₂C≡CH |
| 635 | O | F | Cl | SCH₂CON-pyrrolidinyl |
| 636 | O | F | Cl | SCH₂CSN-pyrrolidinyl |
| 637 | O | F | Cl | SCH₂CS₂-cyclopentyl |
| 638 | O | F | Cl | SCH(CH₃)CO₂H |
| 639 | O | F | Cl | SCH(CH₃)CO₂CH₃ |
| 640 | O | F | Cl | SCH(CH₃)CO₂C₂H₅ |
| 641 | O | F | Cl | SCH(CH₃)CO₂CH₂CH₃ |
| 642 | O | F | Cl | SCH(CH₃)CO₂CH(CH₃)₂ |
| 643 | O | F | Cl | SCH(CH₃)CO₂CH₂(CH₂)₂CH₃ |
| 644 | O | F | Cl | SCH(CH₃)CO₂-cyclopentyl |
| 645 | O | F | Cl | SCH(CH₃)CO₂CH₂CH₂Cl |
| 646 | O | F | Cl | SCH(CH₃)CO₂CH₂CH=CH₂ |
| 647 | O | F | Cl | SCH(CH₃)CO₂CH₂C≡CH |
| 648 | O | F | Cl | SCH(CH₃)CO₂CH₂CH₂OCH₃ |
| 649 | O | F | Cl | SCH(CH₃)C(O)SCH₃ |
| 650 | O | F | Cl | SCH(CH₃)CON(CH₃)₂ |
| 651 | O | F | Cl | SCH(CH₃)CON(C₂H₅)₂ |
| 652 | O | F | Cl | SCH(CH₃)CON-pyrrolidinyl |
| 653 | O | F | Cl | SCH(CH₃)CON-piperidinyl |
| 654 | O | F | Cl | SCH(CH₃)CONHCH₂C≡CH |
| 655 | O | F | Cl | SCH(CH₃)CSN(CH₃)₂ |
| 656 | O | F | Cl | SCH(CH₃)CO₂CH₂CO₂CH₃ |
| 657 | O | F | Cl | SCH(CH₃)CO₂CH₂CO₂C₂H₅ |
| 658 | O | F | Cl | SCH(CH₃)CO₂CH(CH₃)CO₂CH₃ |
| 659 | O | F | Cl | SCH(CH₃)CO₂CH(CH₃)CO₂C₂H₅ |
| 660 | O | F | Cl | SCH(C₂H₅)CO₂H |
| 661 | O | F | Cl | SCH(C₂H₅)CO₂CH₃ |
| 662 | O | F | Cl | SCH(C₂H₅)CO₂C₂H₅ |
| 663 | O | F | Cl | SCH(C₂H₅)CO₂CH(CH₃)₂ |
| 664 | O | F | Cl | SCH(C₂H₅)CO₂CH₂(CH₂)₂CH₃ |
| 665 | O | F | Cl | SCH(C₂H₅)CO₂C(CH₃)₃ |
| 666 | O | F | Cl | SCH(C₂H₅)CO₂-cyclopentyl |
| 667 | O | F | Cl | SCH(C₂H₅)CO₂-cyclohexyl |
| 668 | O | F | Cl | SCH(C₂H₅)CO₂CH₂CH₂Cl |
| 669 | O | F | Cl | SCH(C₂H₅)CO₂CH₂CH=CH₂ |
| 670 | O | F | Cl | SCH(C₂H₅)CO₂CH₂C≡CH |
| 671 | O | F | Cl | SCH(C₂H₅)CON(CH₃)₂ |
| 672 | O | F | Cl | SCH(C₂H₅)CON(C₂H₅)₂ |
| 673 | O | F | Cl | SCH(C₂H₅)CONHCH₃ |
| 674 | O | F | Cl | SCH(C₂H₅)CON-pyrrolidinyl |
| 675 | O | F | Cl | SCH(C₂H₅)CON-piperidinyl |
| 676 | O | F | Cl | SCH(C₂H₅)C(O)SCH₃ |
| 677 | O | F | Cl | SCH(C₂H₅)CSN(CH₃)₂ |
| 678 | O | F | Cl | SCH(C₂H₅)CSN-piperidinyl |
| 679 | O | F | Cl | SCH(CH₂CH₂CH₃)CO₂H |
| 680 | O | F | Cl | SCH(CH₂CH₂CH₃)CO₂CH₃ |
| 681 | O | F | Cl | SCH(CH₂CH₂CH₃)CO₂C₂H₅ |
| 682 | O | F | Cl | SCH(CH(CH₃)₂)CO₂CH₃ |
| 683 | O | F | Cl | SCH(CH(CH₃)₂)CO₂C₂H₅ |

TABLE 1-continued

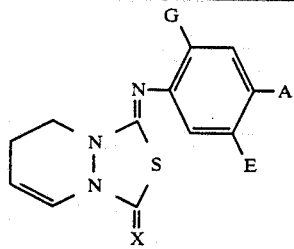

| No. | X | G | A | E |
|---|---|---|---|---|
| 684 | O | F | Cl | SCH(CH(CH₃)₂CO₂-cyclopentyl |
| 685 | O | F | Cl | SCH(CH(CH₃)₂)CON(CH₃)₂ |
| 686 | O | F | Cl | (S-tetrahydrofuranone) |
| 687 | O | F | Cl | (S-tetrahydropyranone) |
| 688 | O | F | Cl | SCH₂COCH₃ |
| 689 | O | F | Cl | SCH₂COC₂H₅ |
| 690 | O | F | Cl | SCH₂COCH(CH₃)₂ |
| 691 | O | F | Cl | SCH₂COCH₂CH₂CH₃ |
| 692 | O | F | Cl | SCH₂C(CH₃)=NOH |
| 693 | O | F | Cl | SCH₂C(CH₃)=NOCH₃ |
| 694 | O | F | Cl | SCH₂C(CH₃)=NOC₂H₅ |
| 695 | O | F | Cl | SCH₂C(CH₃)=NOCH₂CO₂CH |
| 696 | O | F | Cl | SCH₂C(C₂H₅)=NOCH₃ |
| 697 | O | F | Cl | SCH₂C(CH₃)=NOCOCH₃ |
| 698 | O | F | Cl | SCH₂C(C₂H₅)=NOCH₂CO₂CH₃ |
| 699 | O | F | Cl | SCH₂C(C₂H₅)=NOCH(CH₃)₂ |
| 700 | O | F | Cl | SCH₂-C(CH₃)(O-)(O-) dioxolane |
| 701 | O | F | Cl | SCH₂-C(C₂H₅)(O-)(O-) dioxolane |
| 702 | O | F | Cl | SCH₂-C(CH(CH₃)₂)(O-)(O-) dioxolane |
| 703 | O | F | Cl | SCH₂-C(CH₃)(S-)(S-) dithiolane |
| 704 | O | F | Cl | SCH₂-C(C₂H₅)(S-)(S-) dithiolane |
| 705 | O | F | Cl | SCH₂-C(CH(CH₃)₂)(S-)(S-) dithiolane |
| 706 | O | Cl | Cl | OCH₂C≡CH |
| 707 | O | F | Br | OCH₂C≡CH |
| 708 | O | F | NO₂ | OCH₂C≡CH |
| 709 | O | Cl | Cl | SCH(CH₃)₂ |

TABLE 1-continued

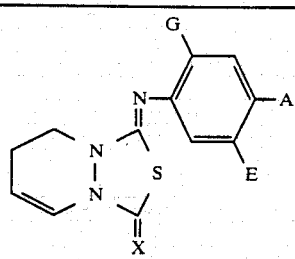

| No. | X | G | A | E |
|---|---|---|---|---|
| 710 | O | F | Br | SCH(CH₃)₂ |
| 711 | O | F | NO₂ | SCH(CH₃)₂ |
| 712 | O | F | Cl | CO₂C(CH₃)₃ |
| 713 | O | F | Br | CO₂C₂H₅ |
| 714 | O | Cl | Cl | CO₂C₂H₅ |
| 715 | O | F | NO₂ | CO₂C₂H₅ |
| 716 | O | H | Cl | CO₂CH₃ |
| 717 | O | H | Cl | CO₂C₂H₅ |
| 718 | O | H | Cl | CO₂CH(CH₃)₂ |
| 719 | O | H | Cl | CO₂C(CH₃)₃ |
| 720 | O | H | Cl | CO₂-cyclopentyl |
| 721 | O | H | Cl | CO₂H |
| 722 | S | F | Cl | OCH₂C≡N |
| 723 | S | F | Cl | (tetrahydropyran-O) |
| 724 | S | F | Cl | (tetrahydrothiopyran-O) |
| 725 | S | F | Cl | OCH₂CO₂CH(CH₃)CO₂CH₃ |
| 726 | S | F | Cl | OCH₂CO₂CH(CH₃)CO₂C₂H₅ |
| 727 | S | F | Cl | OCH₂CO₂C(CH₃)₃ |
| 728 | S | F | Cl | OCH₂CON(CH₃)₂ |
| 729 | S | F | Cl | OCH₂CON(C₂H₅)₂ |
| 730 | S | F | Cl | OCH₂CON(piperidine) |
| 731 | S | F | Cl | OCH(CH₃)CO₂CH₃ |
| 732 | S | F | Cl | OCH(CH₃)CO₂C₂H₅ |
| 733 | S | F | Cl | OCH(CH₃)CO₂-cyclopentyl |
| 734 | S | F | Cl | OCH(CH₃)CON(CH₃)₂ |
| 735 | S | F | Cl | OCH(C₂H₅)CO₂CH₃ |
| 736 | S | F | Cl | OCH(C₂H₅)CON(CH₃)₂ |
| 737 | S | F | Cl | OCH(C₂H₅)CON(piperidine) |
| 738 | S | F | Cl | OCH₂COCH₃ |
| 739 | S | F | Cl | OCH₂COC₂H₅ |
| 740 | S | F | Cl | OCH₂C(CH₃)=NOH |
| 741 | S | F | Cl | OCH₂C(CH₃)=NOCH₃ |
| 742 | S | F | Cl | OCH₂C(CH₃)=NOC₂H₅ |
| 743 | S | F | Cl | OCH₂C(CH₃)=NOCOCH₃ |

TABLE 1-continued

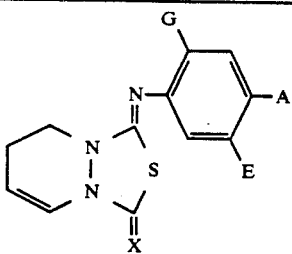

| No. | X | G | A | E |
|---|---|---|---|---|
| 744 | S | F | Cl | OCH₂–C(CH₃)(O-CH₂-CH₂-O) (1,3-dioxolane) |
| 745 | S | F | Cl | OCH₂–C(CH₃)(S-CH₂-CH₂-S) (1,3-dithiolane) |
| 746 | S | F | Cl | 3-oxy-tetrahydrofuran-2-one |
| 747 | S | F | Cl | OCH(CH(CH₃)₂)CO₂CH₃ |
| 748 | S | F | Cl | OCH₂CO₂CH₂CH₂OCH₃ |
| 749 | S | F | Cl | OCH₂CO₂CH₂CH=CH₂ |
| 750 | S | F | Cl | OCH₂CO₂CH₂C≡CH |
| 751 | S | F | Cl | OCH₂CO₂CH₂CH₂Cl |
| 752 | S | F | Cl | OCH₂CO₂CH₂CF₃ |
| 753 | S | F | Cl | OCH₂C(O)SCH₃ |
| 754 | S | F | Cl | OCH₂C(O)SC₂H₅ |
| 755 | S | F | Cl | OCH₂C(O)S-cyclopentyl |
| 756 | S | F | Cl | OCH₂CS₂CH₃ |
| 757 | S | F | Cl | OCH(CH₃)C(O)SC₂H₅ |
| 758 | S | F | Cl | OCH(CH₃)C(O)SC₂H₅ |
| 759 | S | F | Cl | OCH(C₂H₅)C(O)SCH₃ |
| 760 | S | F | Cl | OCH(C₂H₅)C(O)SC₂H₅ |
| 761 | S | F | Cl | OCH₂CSN(CH₃)₂ |
| 762 | S | F | Cl | OCH₂CSN(C₂H₅)₂ |
| 763 | S | F | Cl | OCH₂CSN-piperidinyl |
| 764 | S | F | Cl | OCH(CH₃)CSN(CH₃)₂ |
| 765 | S | F | Cl | OCH(CH(CH₃)₂)C(O)SCH₃ |
| 766 | S | F | Cl | OCH(CH₂CH₂CH₃)CO₂CH₃ |
| 767 | S | F | Cl | SCH₂C≡N |
| 768 | S | F | Cl | tetrahydropyran-2-ylthio |
| 769 | S | F | Cl | tetrahydrothiopyran-2-ylthio |
| 770 | S | F | Cl | SCH₂CO₂C(CH₃)₃ |
| 771 | S | F | Cl | SCH₂CO₂CH₂CO₂CH₃ |
| 772 | S | F | Cl | SCH₂CO₂CH₂CO₂C₂H₅ |
| 773 | S | F | Cl | SCH₂CO₂CH(CH₃)CO₂CH₃ |
| 774 | S | F | Cl | SCH₂CO₂CH(CH₃)CO₂C₂H₅ |

TABLE 1-continued

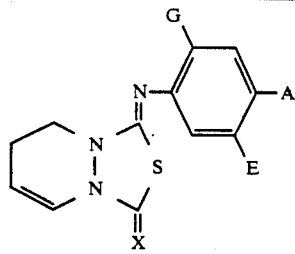

| No. | X | G | A | E |
|---|---|---|---|---|
| 775 | S | F | Cl | SCH₂CO₂CH₂CH₂Cl |
| 776 | S | F | Cl | SCH₂CO₂CH₂CH₂Br |
| 777 | S | F | Cl | SCH₂CO₂CH₂CF₃ |
| 778 | S | F | Cl | SCH₂CO₂CH₂CH=CH₂ |
| 779 | S | F | Cl | SCH₂CO₂CH₂C≡CH |
| 780 | S | F | Cl | SCH₂CO₂CH(CH₃)C≡CH |
| 781 | S | F | Cl | SCH₂CO₂CH₂CH₂OCH₃ |
| 782 | S | F | Cl | SCH₂CO₂CH₂CH₂OC₂H₅ |
| 783 | S | F | Cl | SCH₂C(O)SCH₃ |
| 784 | S | F | Cl | SCH₂C(O)SC₂H₅ |
| 785 | S | F | Cl | SCH₂CS₂CH₃ |
| 786 | S | F | Cl | SCH₂C(O)S-cyclopentyl |
| 787 | S | F | Cl | SCH₂CON(CH₃)₂ |
| 788 | S | F | Cl | SCH₂CON(C₂H₅)₂ |
| 789 | S | F | Cl | SCH₂CONH(CH₃) |
| 790 | S | F | Cl | SCH₂CONH(C₂H₅) |
| 791 | S | F | Cl | SCH₂CON-piperidinyl |
| 792 | S | F | Cl | SCH₂CSN(CH₃)₂ |
| 793 | S | F | Cl | SCH₂CSN(C₂H₅)₂ |
| 794 | S | F | Cl | SCH₂CSN-piperidinyl |
| 795 | S | F | Cl | SCH₂CONHCH₂C≡CH |
| 796 | S | F | Cl | SCH₂CON-pyrrolidinyl |
| 797 | S | F | Cl | SCH₂CSN-pyrrolidinyl |
| 798 | S | F | Cl | SCH₂CS₂-cyclopentyl |
| 799 | S | F | Cl | SCH(CH₃)CO₂H |
| 800 | S | F | Cl | SCH(CH₃)CO₂CH₃ |
| 801 | S | F | Cl | SCH(CH₃)CO₂C₂H₅ |
| 802 | S | F | Cl | SCH(CH₃)CO₂CH₂CH₂CH₃ |
| 803 | S | F | Cl | SCH(CH₃)CO₂CH(CH₃)₂ |
| 804 | S | F | Cl | SCH(CH₃CO₂CH₂(CH₂)₂CH₃ |
| 805 | S | F | Cl | SCH(CH₃)CO₂-cyclopentyl |
| 806 | S | F | Cl | SCH(CH₃)CO₂CH₂CH₂Cl |
| 807 | S | F | Cl | SCH(CH₃)CO₂CH₂CH=CH₂ |

TABLE 1-continued

Structure (compounds 808–839):

An bicyclic system with N–N, S, =N-aryl (G, A, E substituents on aryl), and X substituent.

| No. | X | G | A | E |
|-----|---|---|---|---|
| 808 | S | F | Cl | SCH(CH$_3$)CO$_2$CH$_2$C≡CH |
| 809 | S | F | Cl | SCH(CH$_3$)CO$_2$CH$_2$CH$_2$OCH$_3$ |
| 810 | S | F | Cl | SCH(CH$_3$)C(O)SCH$_3$ |
| 811 | S | F | Cl | SCH(CH$_3$)CON(CH$_3$)$_2$ |
| 812 | S | F | Cl | SCH(CH$_3$)CON(C$_2$H$_5$)$_2$ |
| 813 | S | F | Cl | SCH(CH$_3$)CON(pyrrolidinyl) |
| 814 | S | F | Cl | SCH(CH$_3$)CON(piperidinyl) |
| 815 | S | F | Cl | SCH(CH$_3$)CONHCH$_2$C≡CH |
| 816 | S | F | Cl | SCH(CH$_3$)CSN(CH$_3$)$_2$ |
| 817 | S | F | Cl | SCH(CH$_3$)CO$_2$CH$_2$CO$_2$CH$_3$ |
| 818 | S | F | Cl | SCH(CH$_3$)CO$_2$CH$_2$CO$_2$C$_2$H$_5$ |
| 819 | S | F | Cl | SCH(CH$_3$)CO$_2$CH(CH$_3$)CO$_2$CH$_3$ |
| 820 | S | F | Cl | SCH(CH$_3$)CO$_2$CH(CH$_3$)CO$_2$C$_2$H$_5$ |
| 821 | S | F | Cl | SCH(C$_2$H$_5$)CO$_2$H |
| 822 | S | F | Cl | SCH(C$_2$H$_5$)CO$_2$CH$_3$ |
| 823 | S | F | Cl | SCH(C$_2$H$_5$)CO$_2$C$_2$H$_5$ |
| 824 | S | F | Cl | SCH(C$_2$H$_5$)CO$_2$CH(CH$_3$)$_2$ |
| 825 | S | F | Cl | SCH(C$_2$H$_5$)CO$_2$CH$_2$(CH$_2$)$_2$CH$_3$ |
| 826 | S | F | Cl | SCH(C$_2$H$_5$)CO$_2$C(CH$_3$)$_3$ |
| 827 | S | F | Cl | SCH(C$_2$H$_5$)CO$_2$-cyclopentyl |
| 828 | S | F | Cl | SCH(C$_2$H$_5$)CO$_2$-cyclohexyl |
| 829 | S | F | Cl | SCH(C$_2$H$_5$)CO$_2$CH$_2$CH$_2$Cl |
| 830 | S | F | Cl | SCH(C$_2$H$_5$)CO$_2$CH$_2$CH=CH$_2$ |
| 831 | S | F | Cl | SCH(C$_2$H$_5$)CO$_2$CH$_2$C≡CH |
| 832 | S | F | Cl | SCH(C$_2$H$_5$)CON(CH$_3$)$_2$ |
| 833 | S | F | Cl | SCH(C$_2$H$_5$)CON(C$_2$H$_5$)$_2$ |
| 834 | S | F | Cl | SCH(C$_2$H$_5$)CONHCH$_3$ |
| 835 | S | F | Cl | SCH(C$_2$H$_5$)CON(pyrrolidinyl) |
| 836 | S | F | Cl | SCH(C$_2$H$_5$)CON(piperidinyl) |
| 837 | S | F | Cl | SCH(C$_2$H$_5$)C(O)SCH$_3$ |
| 838 | S | F | Cl | SCH(C$_2$H$_5$)CSN(CH$_3$)$_2$ |
| 839 | S | F | Cl | SCH(C$_2$H$_5$)CSN(piperidinyl) |

| No. | X | G | A | E |
|-----|---|---|---|---|
| 840 | S | F | Cl | SCH(CH$_2$CH$_2$CH$_3$)CO$_2$H |
| 841 | S | F | Cl | SCH(CH$_2$CH$_2$CH$_3$)CO$_2$CH$_3$ |
| 842 | S | F | Cl | SCH(CH$_2$CH$_2$CH$_3$)CO$_2$C$_2$H$_5$ |
| 843 | S | F | Cl | SCH(CH(CH$_3$)$_2$)CO$_2$CH$_3$ |
| 844 | S | F | Cl | SCH(CH(CH$_3$)$_2$)CO$_2$C$_2$H$_5$ |
| 845 | S | F | Cl | SCH(CH(CH$_3$)$_2$)CO$_2$-cyclopentyl |
| 846 | S | F | Cl | SCH(CH(CH$_3$)$_2$)CON(CH$_3$)$_2$ |
| 847 | S | F | Cl | γ-thiobutyrolactone-S |
| 848 | S | F | Cl | δ-thiovalerolactone-S |
| 849 | S | F | Cl | SCH$_2$COCH$_3$ |
| 850 | S | F | Cl | SCH$_2$COC$_2$H$_5$ |
| 851 | S | F | Cl | SCH$_2$COCH(CH$_3$)$_2$ |
| 852 | S | F | Cl | SCH$_2$COCH$_2$CH$_2$CH$_3$ |
| 853 | S | F | Cl | SCH$_2$C(CH$_3$)=NOH |
| 854 | S | F | Cl | SCH$_2$C(CH$_3$)=NOCH$_3$ |
| 855 | S | F | Cl | SCH$_2$C(CH$_3$)=NOC$_2$H$_5$ |
| 856 | S | F | Cl | SCH$_2$C(CH$_3$)=NOCH$_2$CO$_2$CH$_3$ |
| 857 | S | F | Cl | SCH$_2$C(C$_2$H$_5$)=NOCH$_3$ |
| 858 | S | F | Cl | SCH$_2$C(CH$_3$)=NOCOCH$_3$ |
| 859 | S | F | Cl | SCH$_2$C(C$_2$H$_5$)=NOCH$_2$CO$_2$CH$_3$ |
| 860 | S | F | Cl | SCH$_2$C(C$_2$H$_5$)=NOCH$_2$(CH$_3$)$_2$ |
| 861 | S | F | Cl | SCH$_2$-C(CH$_3$)(OCH$_2$CH$_2$O) (1,3-dioxolane) |
| 862 | S | F | Cl | SCH$_2$-C(C$_2$H$_5$)(OCH$_2$CH$_2$O) |
| 863 | S | F | Cl | SCH$_2$-C(CH(CH$_3$)$_2$)(OCH$_2$CH$_2$O) |
| 864 | S | F | Cl | SCH$_2$-C(CH$_3$)(SCH$_2$CH$_2$S) (1,3-dithiolane) |
| 865 | S | F | Cl | SCH$_2$-C(C$_2$H$_5$)(SCH$_2$CH$_2$S) |

TABLE 1-continued

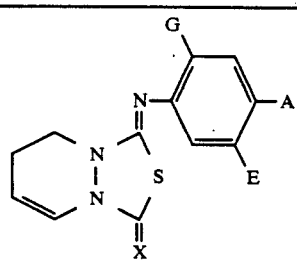

| No. | X | G | A | E |
|-----|---|---|---|---|
| 866 | S | F | Cl | SCH₂—C—CH(CH₃)₂ (dithiolane) |
| 867 | S | Cl | Cl | OCH₂C≡CH |
| 868 | S | F | Br | OCH₂C≡CH |
| 869 | S | F | NO₂ | OCH₂C≡CH |
| 870 | S | Cl | Cl | SCH(CH₃)₂ |
| 871 | S | F | Br | SCH(CH₃)₂ |
| 872 | S | F | NO₂ | SCH(CH₃)₂ |
| 873 | S | F | Cl | CO₂C(CH₃)₃ |
| 874 | S | F | Br | CO₂C₂H₅ |
| 875 | S | Cl | Cl | CO₂C₂H₅ |
| 876 | S | F | NO₂ | CO₂C₂H₅ |
| 877 | S | H | Cl | CO₂CH₃ |
| 878 | S | H | Cl | CO₂C₂H₅ |
| 879 | S | H | Cl | CO₂CH(CH₃)₂ |
| 880 | S | H | Cl | CO₂C(CH₃)₃ |
| 881 | S | H | Cl | CO₂-cyclopentyl |
| 882 | S | H | Cl | CO₂H |

TABLE 2

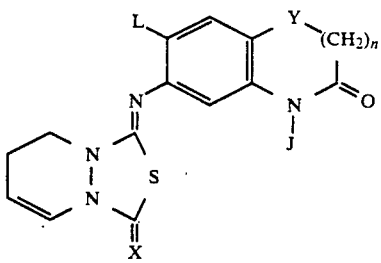

| No. | X | L | Y | n | J |
|-----|---|---|---|---|---|
| 1001 | O | F | O | 0 | H |
| 1002 | O | F | O | 0 | CH₃ |
| 1003 | O | F | O | 0 | C₂H₅ |
| 1004 | O | F | O | 0 | CH₂CH₂CH₃ |
| 1005 | O | F | O | 0 | CH(CH₃)₂ |
| 1006 | O | F | O | 0 | CH₂(CH₂)₂CH₃ |
| 1007 | O | F | O | 0 | CH-cyclopropyl |
| 1008 | O | F | O | 0 | CH-cyclobutyl |
| 1009 | O | F | O | 0 | CH-cyclopentyl |
| 1010 | O | F | O | 0 | CH-cyclohexyl |
| 1011 | O | F | O | 0 | CH₂-cyclopropyl |
| 1012 | O | F | O | 0 | CH₂-cyclobutyl |
| 1013 | O | F | O | 0 | CH₂-cyclopentyl |
| 1014 | O | F | O | 0 | CH₂-cyclohexyl |
| 1015 | O | F | O | 0 | CH=CH₂ |
| 1016 | O | F | O | 0 | CH₂CH=CH₂ |
| 1017 | O | F | O | 0 | CH₂C≡CH |
| 1018 | O | F | O | 0 | CH₂OCH₃ |
| 1019 | O | F | O | 0 | CH₂OC₂H₅ |
| 1020 | O | F | O | 0 | CH₂CH₂OCH₃ |
| 1021 | O | F | O | 0 | CH₂CH₂OC₂H₅ |
| 1022 | O | F | O | 0 | CH₂C≡N |
| 1023 | O | F | O | 0 | CH₂CO₂H |
| 1024 | O | F | O | 0 | CH₂CO₂CH₃ |
| 1025 | O | F | O | 0 | CH₂CO₂C₂H₅ |
| 1026 | O | F | O | 0 | CH₂CO₂CH₂CH₂CH₃ |
| 1027 | O | F | O | 0 | CH₂CO₂CH(CH₃)₂ |
| 1028 | O | F | O | 0 | CH₂CO₂CH₂(CH₂)₂CH₃ |
| 1029 | O | F | O | 0 | CH₂CO₂C(CH₃)₃ |
| 1030 | O | F | O | 0 | CH₂CO₂-cyclopropyl |
| 1031 | O | F | O | 0 | CH₂CO₂-cyclobutyl |
| 1032 | O | F | O | 0 | CH₂CO₂-cyclopentyl |
| 1033 | O | F | O | 0 | CH₂CO₂-cyclohexyl |

TABLE 2-continued

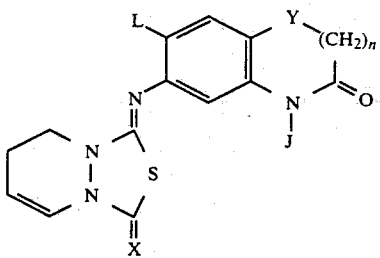

| No. | X | L | Y | n | J |
|---|---|---|---|---|---|
| 1034 | O | F | O | 0 | CH₂CO₂CH₂-cyclopropyl |
| 1035 | O | F | O | 0 | CH₂CO₂CH₂-cyclobutyl |
| 1036 | O | F | O | 0 | CH₂CO₂CH₂-cyclopentyl |
| 1037 | O | F | O | 0 | CH₂CO₂CH₂-cyclohexyl |
| 1038 | O | F | O | 0 | CH₂CH₂CO₂H |
| 1039 | O | F | O | 0 | CH₂CH₂CO₂CH₃ |
| 1040 | O | F | O | 0 | CH₂CH₂CO₂C₂H₅ |
| 1041 | O | F | O | 0 | CH₂CH₂CO₂CH₂CH₂CH₃ |
| 1042 | O | F | O | 0 | CH₂CH₂CO₂CH(CH₃)₂ |
| 1043 | O | F | O | 0 | CH₂CH₂CO₂C(CH₃)₃ |
| 1044 | O | F | O | 0 | CH₂CH₂CO₂-cyclopropyl |
| 1045 | O | F | O | 0 | CH₂CH₂CO₂-cyclobutyl |
| 1046 | O | F | O | 0 | CH₂CH₂CO₂-cyclopentyl |
| 1047 | O | F | O | 0 | CH₂CH₂CO₂-cyclohexyl |
| 1048 | O | F | O | 0 | CH₂CH₂CO₂CH₂-cyclopropyl |
| 1049 | O | F | O | 0 | CH₂CH₂CO₂CH₂-cyclobutyl |
| 1050 | O | F | O | 0 | CH₂CH₂CO₂CH₂-cyclopentyl |
| 1051 | O | F | O | 0 | CH₂CH₂CO₂CH₂-cyclohexyl |
| 1052 | O | F | O | 0 | CH₂CF₃ |
| 1053 | O | F | O | 0 | CH₂Cl |
| 1054 | O | F | O | 0 | CH₂C(Cl)=C(Cl)H |
| 1055 | O | F | O | 0 | CH₂C(Cl)=C(H)Cl |
| 1056 | O | F | O | 0 | CH₂C(Cl)=CH₂ |
| 1057 | O | F | O | 0 | CH₂C≡CBr |
| 1058 | O | F | O | 1 | H |
| 1059 | O | F | O | 1 | CH₃ |
| 1060 | O | F | O | 1 | C₂H₅ |
| 1061 | O | F | O | 1 | CH₂CH₂CH₃ |
| 1062 | O | F | O | 1 | CH(CH₃)₂ |
| 1063 | O | F | O | 1 | CH₂(CH₂)₂CH₃ |
| 1064 | O | F | O | 1 | CH-cyclopropyl |
| 1065 | O | F | O | 1 | CH-cyclobutyl |
| 1066 | O | F | O | 1 | CH-cyclopentyl |
| 1067 | O | F | O | 1 | CH-cyclohexyl |
| 1068 | O | F | O | 1 | CH₂-cyclopropyl |
| 1069 | O | F | O | 1 | CH₂-cyclobutyl |
| 1070 | O | F | O | 1 | CH₂-cyclopentyl |

TABLE 2-continued

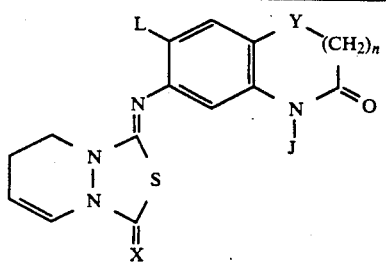

| No. | X | L | Y | n | J |
|---|---|---|---|---|---|
| 1071 | O | F | O | 1 | CH2-cyclohexyl |
| 1072 | O | F | O | 1 | CH=CH2 |
| 1073 | O | F | O | 1 | CH2CH=CH2 |
| 1074 | O | F | O | 1 | CH2C≡CH |
| 1075 | O | F | O | 1 | CH2OCH3 |
| 1076 | O | F | O | 1 | CH2OC2H5 |
| 1077 | O | F | O | 1 | CH2CH2OCH3 |
| 1078 | O | F | O | 1 | CH2CH2OC2H5 |
| 1079 | O | F | O | 1 | CH2C≡N |
| 1080 | O | F | O | 1 | CH2CO2H |
| 1081 | O | F | O | 1 | CH2CO2CH3 |
| 1082 | O | F | O | 1 | CH2CO2C2H5 |
| 1083 | O | F | O | 1 | CH2CO2CH2CH2CH3 |
| 1084 | O | F | O | 1 | CH2CO2CH(CH3)2 |
| 1085 | O | F | O | 1 | CH2CO2CH2(CH2)2CH3 |
| 1086 | O | F | O | 1 | CH2CO2C(CH3)3 |
| 1087 | O | F | O | 1 | CH2CO2-cyclopropyl |
| 1088 | O | F | O | 1 | CH2CO2-cyclobutyl |
| 1089 | O | F | O | 1 | CH2CO2-cyclopentyl |
| 1090 | O | F | O | 1 | CH2CO2-cyclohexyl |
| 1091 | O | F | O | 1 | CH2CO2CH2-cyclopropyl |
| 1092 | O | F | O | 1 | CH2CO2CH2-cyclobutyl |
| 1093 | O | F | O | 1 | CH2CO2CH2-cyclopentyl |
| 1094 | O | F | O | 1 | CH2CO2CH2-cyclohexyl |
| 1095 | O | F | O | 1 | CH2CH2CO2H |
| 1096 | O | F | O | 1 | CH2CH2CO2CH3 |
| 1097 | O | F | O | 1 | CH2CH2CO2C2H5 |
| 1098 | O | F | O | 1 | CH2CH2CO2CH2CH2CH3 |
| 1099 | O | F | O | 1 | CH2CH2CO2CH(CH3)2 |
| 1100 | O | F | O | 1 | CH2CH2CO2C(CH3)3 |
| 1101 | O | F | O | 1 | CH2CH2CO2-cyclopropyl |
| 1102 | O | F | O | 1 | CH2CH2CO2-cyclobutyl |
| 1103 | O | F | O | 1 | CH2CH2CO2-cyclopentyl |
| 1104 | O | F | O | 1 | CH2CH2CO2-cyclohexyl |
| 1105 | O | F | O | 1 | CH2CH2CO2CH2-cyclopropyl |
| 1106 | O | F | O | 1 | CH2CH2CO2CH2-cyclobutyl |
| 1107 | O | F | O | 1 | CH2CH2CO2CH2-cyclopentyl |
| 1108 | O | F | O | 1 | CH2CH2CO2CH2-cyclohexyl |
| 1109 | O | F | O | 1 | CH2CF3 |
| 1110 | O | F | O | 1 | CH2Cl |
| 1111 | O | F | O | 1 | CH2C(Cl)=C(Cl)(H) |
| 1112 | O | F | O | 1 | CH2C(Cl)=C(Cl)(H) |
| 1113 | O | F | O | 1 | CH2C(Cl)=CH2 |
| 1114 | O | F | O | 0 | CH2C≡CBr |
| 1115 | O | F | S | 0 | H |
| 1116 | O | F | S | 0 | CH3 |
| 1117 | O | F | S | 0 | C2H5 |

TABLE 2-continued

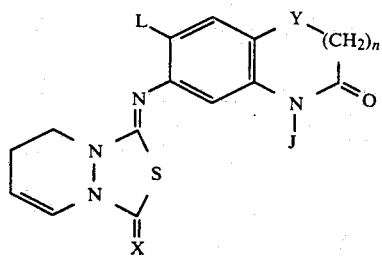

| No. | X | L | Y | n | J |
|---|---|---|---|---|---|
| 1118 | O | F | S | 0 | CH$_2$CH$_2$CH$_3$ |
| 1119 | O | F | S | 0 | CH(CH$_3$)$_2$ |
| 1120 | O | F | S | 0 | CH$_2$(CH$_2$)$_2$CH$_3$ |
| 1121 | O | F | S | 0 | CH-cyclopropyl |
| 1122 | O | F | S | 0 | CH-cyclobutyl |
| 1123 | O | F | S | 0 | CH-cyclopentyl |
| 1124 | O | F | S | 0 | CH-cyclohexyl |
| 1125 | O | F | S | 0 | CH$_2$-cyclopropyl |
| 1126 | O | F | S | 0 | CH$_2$-cyclobutyl |
| 1127 | O | F | S | 0 | CH$_2$-cyclopentyl |
| 1128 | O | F | S | 0 | CH$_2$-cyclohexyl |
| 1129 | O | F | S | 0 | CH=CH$_2$ |
| 1130 | O | F | S | 0 | CH$_2$CH=CH$_2$ |
| 1131 | O | F | S | 0 | CH$_2$C≡CH |
| 1132 | O | F | S | 0 | CH$_2$OCH$_3$ |
| 1133 | O | F | S | 0 | CH$_2$OC$_2$H$_5$ |
| 1134 | O | F | S | 0 | CH$_2$CH$_2$OCH$_3$ |
| 1135 | O | F | S | 0 | CH$_2$CH$_2$OC$_2$H$_5$ |
| 1136 | O | F | S | 0 | CH$_2$C≡N |
| 1137 | O | F | S | 0 | CH$_2$CO$_2$H |
| 1138 | O | F | S | 0 | CH$_2$CO$_2$CH$_3$ |
| 1139 | O | F | S | 0 | CH$_2$CO$_2$C$_2$H$_5$ |
| 1140 | O | F | S | 0 | CH$_2$CO$_2$CH$_2$CH$_2$CH$_3$ |
| 1141 | O | F | S | 0 | CH$_2$CO$_2$CH(CH$_3$)$_2$ |
| 1142 | O | F | S | 0 | CH$_2$CO$_2$CH$_2$(CH$_2$)$_2$CH$_3$ |
| 1143 | O | F | S | 0 | CH$_2$CO$_2$C(CH$_3$)$_3$ |
| 1144 | O | F | S | 0 | CH$_2$CO$_2$-cyclopropyl |

TABLE 2-continued

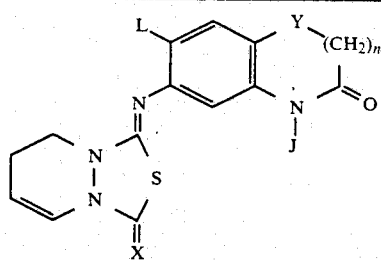

| No. | X | L | Y | n | J |
|---|---|---|---|---|---|
| 1145 | O | F | S | 0 | CH$_2$CO$_2$-cyclobutyl |
| 1146 | O | F | S | 0 | CH$_2$CO$_2$-cyclopentyl |
| 1147 | O | F | S | 0 | CH$_2$CO$_2$-cyclohexyl |
| 1148 | O | F | S | 0 | CH$_2$CO$_2$CH$_2$-cyclopropyl |
| 1149 | O | F | S | 0 | CH$_2$CO$_2$CH$_2$-cyclobutyl |
| 1150 | O | F | S | 0 | CH$_2$CO$_2$CH$_2$-cyclopentyl |
| 1151 | O | F | S | 0 | CH$_2$CO$_2$CH$_2$-cyclohexyl |
| 1152 | O | F | S | 0 | CH$_2$CH$_2$CO$_2$H |
| 1153 | O | F | S | 0 | CH$_2$CH$_2$CO$_2$CH$_3$ |
| 1154 | O | F | S | 0 | CH$_2$CH$_2$CO$_2$C$_2$H$_5$ |
| 1155 | O | F | S | 0 | CH$_2$CH$_2$CO$_2$CH$_2$CH$_2$CH$_3$ |
| 1156 | O | F | S | 0 | CH$_2$CH$_2$CO$_2$CH(CH$_3$)$_2$ |
| 1157 | O | F | S | 0 | CH$_2$CH$_2$CO$_2$C(CH$_3$)$_3$ |
| 1158 | O | F | S | 0 | CH$_2$CH$_2$CO$_2$-cyclopropyl |
| 1159 | O | F | S | 0 | CH$_2$CH$_2$CO$_2$-cyclobutyl |
| 1160 | O | F | S | 0 | CH$_2$CH$_2$CO$_2$-cyclopentyl |
| 1161 | O | F | S | 0 | CH$_2$CH$_2$CO$_2$-cyclohexyl |

TABLE 2-continued

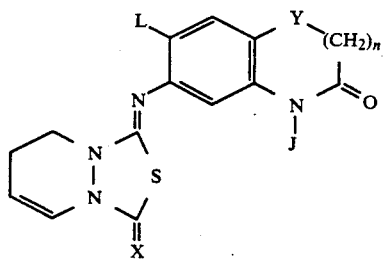

| No. | X | L | Y | n | J |
|---|---|---|---|---|---|
| 1162 | O | F | S | 0 | CH₂CH₂CO₂CH₂-cyclopropyl |
| 1163 | O | F | S | 0 | CH₂CH₂CO₂CH₂-cyclobutyl |
| 1164 | O | F | S | 0 | CH₂CH₂CO₂CH₂-cyclopentyl |
| 1165 | O | F | S | 0 | CH₂CH₂CO₂CH₂-cyclohexyl |
| 1166 | O | F | S | 0 | CH₂CF₃ |
| 1167 | O | F | S | 0 | CH₂Cl |
| 1168 | O | F | S | 0 | CH₂C(Cl)=CHCl (trans) |
| 1169 | O | F | S | 0 | CH₂C(Cl)=CHCl (cis) |
| 1170 | O | F | S | 0 | CH₂C(Cl)=CH₂ |
| 1171 | O | F | S | 0 | CH₂C≡CBr |
| 1172 | O | F | S | 1 | H |
| 1173 | O | F | S | 1 | CH₃ |
| 1174 | O | F | S | 1 | C₂H₅ |
| 1175 | O | F | S | 1 | CH₂CH₂CH₃ |
| 1176 | O | F | S | 1 | CH(CH₃)₂ |
| 1177 | O | F | S | 1 | CH₂(CH₂)₂CH₃ |
| 1178 | O | F | S | 1 | CH-cyclopropyl |
| 1179 | O | F | S | 1 | CH-cyclobutyl |
| 1180 | O | F | S | 1 | CH-cyclopentyl |
| 1181 | O | F | S | 1 | CH-cyclohexyl |

TABLE 2-continued

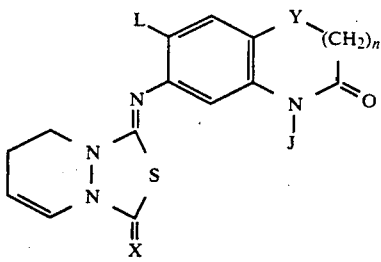

| No. | X | L | Y | n | J |
|---|---|---|---|---|---|
| 1182 | O | F | S | 1 | CH₂-cyclopropyl |
| 1183 | O | F | S | 1 | CH₂-cyclobutyl |
| 1184 | O | F | S | 1 | CH₂-cyclopentyl |
| 1185 | O | F | S | 1 | CH₂-cyclohexyl |
| 1186 | O | F | S | 1 | CH=CH₂ |
| 1187 | O | F | S | 1 | CH₂CH=CH₂ |
| 1188 | O | F | S | 1 | CH₂C≡CH |
| 1189 | O | F | S | 1 | CH₂OCH₃ |
| 1190 | O | F | S | 1 | CH₂OC₂H₅ |
| 1191 | O | F | S | 1 | CH₂CH₂OCH₃ |
| 1192 | O | F | S | 1 | CH₂CH₂OC₂H₅ |
| 1193 | O | F | S | 1 | CH₂C≡N |
| 1194 | O | F | S | 1 | CH₂CO₂H |
| 1195 | O | F | S | 1 | CH₂CO₂CH₃ |
| 1196 | O | F | S | 1 | CH₂CO₂C₂H₅ |
| 1197 | O | F | S | 1 | CH₂CO₂CH₂CH₂CH₃ |
| 1198 | O | F | S | 1 | CH₂CO₂CH(CH₃)₂ |
| 1199 | O | F | S | 1 | CH₂CO₂CH₂(CH₂)₂CH₃ |
| 1200 | O | F | S | 1 | CH₂CO₂C(CH₃)₃ |
| 1201 | O | F | S | 1 | CH₂CO₂-cyclopropyl |
| 1202 | O | F | S | 1 | CH₂CO₂-cyclobutyl |
| 1203 | O | F | S | 1 | CH₂CO₂-cyclopentyl |
| 1204 | O | F | S | 1 | CH₂CO₂-cyclohexyl |
| 1205 | O | F | S | 1 | CH₂CO₂CH₂-cyclopropyl |

TABLE 2-continued

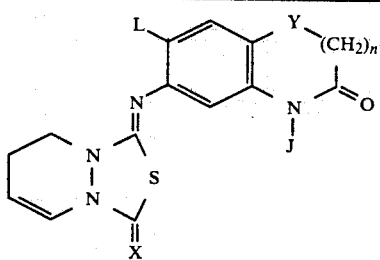

| No. | X | L | Y | n | J |
|---|---|---|---|---|---|
| 1206 | O | F | S | 1 | CH₂CO₂CH₂-cyclobutyl |
| 1207 | O | F | S | 1 | CH₂CO₂CH₂-cyclopentyl |
| 1208 | O | F | S | 1 | CH₂CO₂CH₂-cyclohexyl |
| 1209 | O | F | S | 1 | $CH_2CH_2CO_2H$ |
| 1210 | O | F | S | 1 | $CH_2CH_2CO_2CH_3$ |
| 1211 | O | F | S | 1 | $CH_2CH_2CO_2C_2H_5$ |
| 1212 | O | F | S | 1 | $CH_2CH_2CO_2CH_2CH_2CH_3$ |
| 1213 | O | F | S | 1 | $CH_2CH_2CO_2CH(CH_3)_2$ |
| 1214 | O | F | S | 1 | $CH_2CH_2CO_2C(CH_3)_3$ |
| 1215 | O | F | S | 1 | CH₂CH₂CO₂-cyclopropyl |
| 1216 | O | F | S | 1 | CH₂CH₂CO₂-cyclobutyl |
| 1217 | O | F | S | 1 | CH₂CH₂CO₂-cyclopentyl |
| 1218 | O | F | S | 1 | CH₂CH₂CO₂-cyclohexyl |
| 1219 | O | F | S | 1 | CH₂CH₂CO₂CH₂-cyclopropyl |
| 1220 | O | F | S | 1 | CH₂CH₂CO₂CH₂-cyclobutyl |
| 1221 | O | F | S | 1 | CH₂CH₂CO₂CH₂-cyclopentyl |
| 1222 | O | F | S | 1 | CH₂CH₂CO₂CH₂-cyclohexyl |

TABLE 2-continued

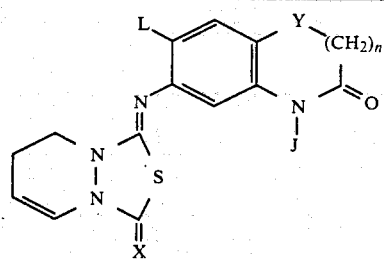

| No. | X | L | Y | n | J |
|---|---|---|---|---|---|
| 1223 | O | F | S | 1 | $CH_2CF_3$ |
| 1224 | O | F | S | 1 | $CH_2Cl$ |
| 1225 | O | F | S | 1 | CH₂–C(Cl)=C(Cl)H |
| 1226 | O | F | S | 1 | CH₂–C(Cl)=C(Cl)H (isomer) |
| 1227 | O | F | S | 1 | $CH_2C(Cl)=CH_2$ |
| 1228 | O | F | S | 1 | $CH_2C\equiv CBr$ |
| 1229 | S | F | O | 0 | H |
| 1230 | S | F | O | 0 | $CH_3$ |
| 1231 | S | F | O | 0 | $C_2H_5$ |
| 1232 | S | F | O | 0 | $CH_2CH_2CH_3$ |
| 1233 | S | F | O | 0 | $CH(CH_3)_2$ |
| 1234 | S | F | O | 0 | $CH_2(CH_2)_2CH_3$ |
| 1235 | S | F | O | 0 | CH-cyclopropyl |
| 1236 | S | F | O | 0 | CH-cyclobutyl |
| 1237 | S | F | O | 0 | CH-cyclopentyl |
| 1238 | S | F | O | 0 | CH-cyclohexyl |
| 1239 | S | F | O | 0 | CH₂-cyclopropyl |
| 1240 | S | F | O | 0 | CH₂-cyclobutyl |
| 1241 | S | F | O | 0 | CH₂-cyclopentyl |
| 1242 | S | F | O | 0 | CH₂-cyclohexyl |

TABLE 2-continued

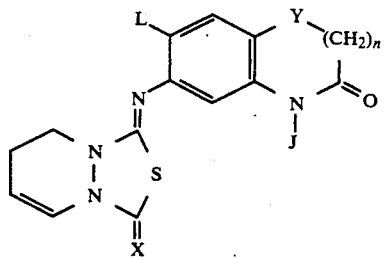

| No. | X | L | Y | n | J |
|---|---|---|---|---|---|
| 1243 | S | F | O | 0 | CH=CH$_2$ |
| 1244 | S | F | O | 0 | CH$_2$CH=CH$_2$ |
| 1245 | S | F | O | 0 | CH$_2$C≡CH |
| 1246 | S | F | O | 0 | CH$_2$OCH$_3$ |
| 1247 | S | F | O | 0 | CH$_2$OC$_2$H$_5$ |
| 1248 | S | F | O | 0 | CH$_2$CH$_2$OCH$_3$ |
| 1249 | S | F | O | 0 | CH$_2$CH$_2$OC$_2$H$_5$ |
| 1250 | S | F | O | 0 | CH$_2$C≡N |
| 1251 | S | F | O | 0 | CH$_2$CO$_2$H |
| 1252 | S | F | O | 0 | CH$_2$CO$_2$CH$_3$ |
| 1253 | S | F | O | 0 | CH$_2$CO$_2$C$_2$H$_5$ |
| 1254 | S | F | O | 0 | CH$_2$CO$_2$CH$_2$CH$_3$ |
| 1255 | S | F | O | 0 | CH$_2$CO$_2$CH(CH$_3$)$_2$ |
| 1256 | S | F | O | 0 | CH$_2$CO$_2$CH$_2$(CH$_2$)$_2$CH$_3$ |
| 1257 | S | F | O | 0 | CH$_2$CO$_2$C(CH$_3$)$_3$ |
| 1258 | S | F | O | 0 | CH$_2$CO$_2$–cyclopropyl |
| 1259 | S | F | O | 0 | CH$_2$CO$_2$–cyclobutyl |
| 1260 | S | F | O | 0 | CH$_2$CO$_2$–cyclopentyl |
| 1261 | S | F | O | 0 | CH$_2$CO$_2$–cyclohexyl |
| 1262 | S | F | O | 0 | CH$_2$CO$_2$CH$_2$–cyclopropyl |
| 1263 | S | F | O | 0 | CH$_2$CO$_2$CH$_2$–cyclobutyl |
| 1264 | S | F | O | 0 | CH$_2$CO$_2$CH$_2$–cyclopentyl |
| 1265 | S | F | O | 0 | CH$_2$CO$_2$CH$_2$–cyclohexyl |
| 1266 | S | F | O | 0 | CH$_2$CH$_2$CO$_2$H |
| 1267 | S | F | O | 0 | CH$_2$CH$_2$CO$_2$CH$_3$ |
| 1268 | S | F | O | 0 | CH$_2$CH$_2$CO$_2$C$_2$H$_5$ |
| 1269 | S | F | O | 0 | CH$_2$CH$_2$CO$_2$CH$_2$CH$_3$ |
| 1270 | S | F | O | 0 | CH$_2$CH$_2$CO$_2$CH(CH$_3$)$_2$ |
| 1271 | S | F | O | 0 | CH$_2$CH$_2$CO$_2$C(CH$_3$)$_3$ |

TABLE 2-continued

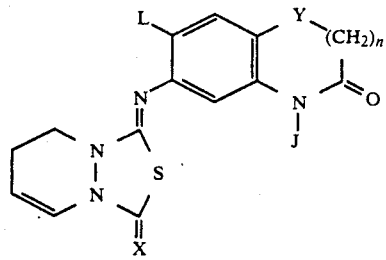

| No. | X | L | Y | n | J |
|---|---|---|---|---|---|
| 1272 | S | F | O | 0 | CH$_2$CH$_2$CO$_2$–cyclopropyl |
| 1273 | S | F | O | 0 | CH$_2$CH$_2$CO$_2$–cyclobutyl |
| 1274 | S | F | O | 0 | CH$_2$CH$_2$CO$_2$–cyclopentyl |
| 1275 | S | F | O | 0 | CH$_2$CH$_2$CO$_2$–cyclohexyl |
| 1276 | S | F | O | 0 | CH$_2$CH$_2$CO$_2$CH$_2$–cyclopropyl |
| 1277 | S | F | O | 0 | CH$_2$CH$_2$CO$_2$CH$_2$–cyclobutyl |
| 1278 | S | F | O | 0 | CH$_2$CH$_2$CO$_2$CH$_2$–cyclopentyl |
| 1279 | S | F | O | 0 | CH$_2$CH$_2$CO$_2$CH$_2$–cyclohexyl |
| 1280 | S | F | O | 0 | CH$_2$CF$_3$ |
| 1281 | S | F | O | 0 | CH$_2$Cl |
| 1282 | S | F | O | 0 | CH$_2$C(Cl)=C(Cl)H |
| 1283 | S | F | O | 0 | CH$_2$C(Cl)=C(Cl)H (isomer) |
| 1284 | S | F | O | 0 | CH$_2$C(Cl)=CH$_2$ |
| 1285 | S | F | O | 0 | CH$_2$C≡CBr |
| 1286 | S | F | O | 1 | H |
| 1287 | S | F | O | 1 | CH$_3$ |
| 1288 | S | F | O | 1 | C$_2$H$_5$ |
| 1289 | S | F | O | 1 | CH$_2$CH$_2$CH$_3$ |
| 1290 | S | F | O | 1 | CH(CH$_3$)$_2$ |
| 1291 | S | F | O | 1 | CH$_2$(CH$_2$)$_2$CH$_3$ |

TABLE 2-continued

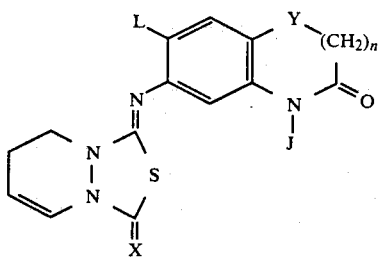

| No. | X | L | Y | n | J |
|---|---|---|---|---|---|
| 1292 | S | F | O | 1 | CH-cyclopropyl |
| 1293 | S | F | O | 1 | CH-cyclobutyl |
| 1294 | S | F | O | 1 | CH-cyclopentyl |
| 1295 | S | F | O | 1 | CH-cyclohexyl |
| 1296 | S | F | O | 1 | CH₂-cyclopropyl |
| 1297 | S | F | O | 1 | CH₂-cyclobutyl |
| 1298 | S | F | O | 1 | CH₂-cyclopentyl |
| 1299 | S | F | O | 1 | CH₂-cyclohexyl |
| 1300 | S | F | O | 1 | CH=CH₂ |
| 1301 | S | F | O | 1 | CH₂CH=CH₂ |
| 1302 | S | F | O | 1 | CH₂C≡CH |
| 1303 | S | F | O | 1 | CH₂OCH₃ |
| 1304 | S | F | O | 1 | CH₂OC₂H₅ |
| 1305 | S | F | O | 1 | CH₂CH₂OCH₃ |
| 1306 | S | F | O | 1 | CH₂CH₂OC₂H₅ |
| 1307 | S | F | O | 1 | CH₂C≡N |
| 1308 | S | F | O | 1 | CH₂CO₂H |
| 1309 | S | F | O | 1 | CH₂CO₂CH₃ |
| 1310 | S | F | O | 1 | CH₂CO₂C₂H₅ |
| 1311 | S | F | O | 1 | CH₂CO₂CH₂CH₂CH₃ |
| 1312 | S | F | O | 1 | CH₂CO₂CH(CH₃)₂ |
| 1313 | S | F | O | 1 | CH₂CO₂CH₂(CH₂)₂CH₃ |
| 1314 | S | F | O | 1 | CH₂CO₂C(CH₃)₃ |
| 1315 | S | F | O | 1 | CH₂CO₂-cyclopropyl |
| 1316 | S | F | O | 1 | CH₂CO₂-cyclobutyl |
| 1317 | S | F | O | 1 | CH₂CO₂-cyclopentyl |
| 1318 | S | F | O | 1 | CH₂CO₂-cyclohexyl |
| 1319 | S | F | O | 1 | CH₂CO₂CH₂-cyclopropyl |
| 1320 | S | F | O | 1 | CH₂CO₂CH₂-cyclobutyl |
| 1321 | S | F | O | 1 | CH₂CO₂CH₂-cyclopentyl |
| 1322 | S | F | O | 1 | CH₂CO₂CH₂-cyclohexyl |
| 1323 | S | F | O | 1 | CH₂CH₂CO₂H |
| 1324 | S | F | O | 1 | CH₂CH₂CO₂CH₃ |
| 1325 | S | F | O | 1 | CH₂CH₂CO₂C₂H₅ |
| 1326 | S | F | O | 1 | CH₂CH₂CO₂CH₂CH₂CH₃ |
| 1327 | S | F | O | 1 | CH₂CH₂CO₂CH(CH₃)₂ |
| 1328 | S | F | O | 1 | CH₂CH₂CO₂C(CH₃)₃ |
| 1329 | S | F | O | 1 | CH₂CH₂CO₂-cyclopropyl |
| 1330 | S | F | O | 1 | CH₂CH₂CO₂-cyclobutyl |
| 1331 | S | F | O | 1 | CH₂CH₂CO₂-cyclopentyl |
| 1332 | S | F | O | 1 | CH₂CH₂CO₂-cyclohexyl |

TABLE 2-continued

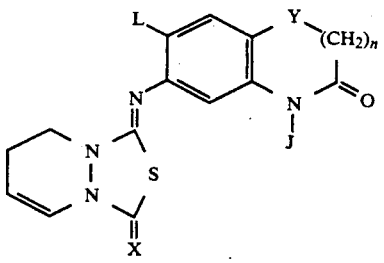

| No. | X | L | Y | n | J |
|---|---|---|---|---|---|
| 1333 | S | F | O | 1 | CH₂CH₂CO₂CH₂-cyclopropyl |
| 1334 | S | F | O | 1 | CH₂CH₂CO₂CH₂-cyclobutyl |
| 1335 | S | F | O | 1 | CH₂CH₂CO₂CH₂-cyclopentyl |
| 1336 | S | F | O | 1 | CH₂CH₂CO₂CH₂-cyclohexyl |
| 1337 | S | F | O | 1 | CH₂CF₃ |
| 1338 | S | F | O | 1 | CH₂Cl |
| 1339 | S | F | O | 1 | CH₂-C(Cl)=C(Cl)H |
| 1340 | S | F | O | 1 | CH₂-C(Cl)=C(H)Cl |
| 1341 | S | F | O | 1 | CH₂C(Cl)=CH₂ |
| 1342 | S | F | O | 1 | CH₂C≡CBr |
| 1343 | S | F | S | 0 | H |
| 1344 | S | F | S | 0 | CH₃ |
| 1345 | S | F | S | 0 | C₂H₅ |
| 1346 | S | F | S | 0 | CH₂CH₂CH₃ |
| 1347 | S | F | S | 0 | CH(CH₃)₂ |
| 1348 | S | F | S | 0 | CH₂(CH₂)₂CH₃ |
| 1349 | S | F | S | 0 | CH-cyclopropyl |
| 1350 | S | F | S | 0 | CH-cyclobutyl |
| 1351 | S | F | S | 0 | CH-cyclopentyl |
| 1352 | S | F | S | 0 | CH-cyclohexyl |

TABLE 2-continued

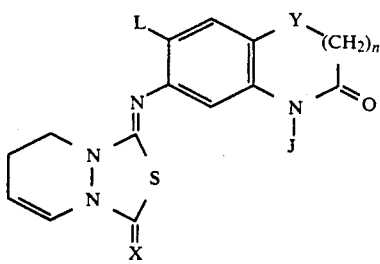

| No. | X | L | Y | n | J |
|---|---|---|---|---|---|
| 1353 | S | F | S | 0 | CH₂-cyclopropyl |
| 1354 | S | F | S | 0 | CH₂-cyclobutyl |
| 1355 | S | F | S | 0 | CH₂-cyclopentyl |
| 1356 | S | F | S | 0 | CH₂-cyclohexyl |
| 1357 | S | F | S | 0 | CH=CH₂ |
| 1358 | S | F | S | 0 | CH₂CH=CH₂ |
| 1359 | S | F | S | 0 | CH₂C≡CH |
| 1360 | S | F | S | 0 | CH₂OCH₃ |
| 1361 | S | F | S | 0 | CH₂OC₂H₅ |
| 1362 | S | F | S | 0 | CH₂CH₂OCH₃ |
| 1363 | S | F | S | 0 | CH₂CH₂OC₂H₅ |
| 1364 | S | F | S | 0 | CH₂C≡N |
| 1365 | S | F | S | 0 | CH₂CO₂H |
| 1366 | S | F | S | 0 | CH₂CO₂CH₃ |
| 1367 | S | F | S | 0 | CH₂CO₂C₂H₅ |
| 1368 | S | F | S | 0 | CH₂CO₂CH₂CH₂CH₃ |
| 1369 | S | F | S | 0 | CH₂CO₂CH(CH₃)₂ |
| 1370 | S | F | S | 0 | CH₂CO₂CH₂(CH₂)₂CH₃ |
| 1371 | S | F | S | 0 | CH₂CO₂C(CH₃)₃ |
| 1372 | S | F | S | 0 | CH₂CO₂-cyclopropyl |
| 1373 | S | F | S | 0 | CH₂CO₂-cyclobutyl |
| 1374 | S | F | S | 0 | CH₂CO₂-cyclopentyl |
| 1375 | S | F | S | 0 | CH₂CO₂-cyclohexyl |
| 1376 | S | F | S | 0 | CH₂CO₂CH₂-cyclopropyl |

TABLE 2-continued

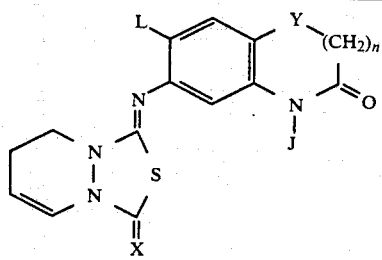

| No. | X | L | Y | n | J |
|---|---|---|---|---|---|
| 1377 | S | F | S | 0 | CH₂CO₂CH₂-cyclobutyl |
| 1378 | S | F | S | 0 | CH₂CO₂CH₂-cyclopentyl |
| 1379 | S | F | S | 0 | CH₂CO₂CH₂-cyclohexyl |
| 1380 | S | F | S | 0 | CH₂CH₂CO₂H |
| 1381 | S | F | S | 0 | CH₂CH₂CO₂CH₃ |
| 1382 | S | F | S | 0 | CH₂CH₂CO₂C₂H₅ |
| 1383 | S | F | S | 0 | CH₂CH₂CO₂CH₂CH₂CH₃ |
| 1384 | S | F | S | 0 | CH₂CH₂CO₂CH(CH₃)₂ |
| 1385 | S | F | S | 0 | CH₂CH₂CO₂C(CH₃)₃ |
| 1386 | S | F | S | 0 | CH₂CH₂CO₂-cyclopropyl |
| 1387 | S | F | S | 0 | CH₂CH₂CO₂-cyclobutyl |
| 1388 | S | F | S | 0 | CH₂CH₂CO₂-cyclopentyl |
| 1389 | S | F | S | 0 | CH₂CH₂CO₂-cyclohexyl |
| 1390 | S | F | S | 0 | CH₂CH₂CO₂CH₂-cyclopropyl |
| 1391 | S | F | S | 0 | CH₂CH₂CO₂CH₂-cyclobutyl |
| 1392 | S | F | S | 0 | CH₂CH₂CO₂CH₂-cyclopentyl |
| 1393 | S | F | S | 0 | CH₂CH₂CO₂CH₂-cyclohexyl |

TABLE 2-continued

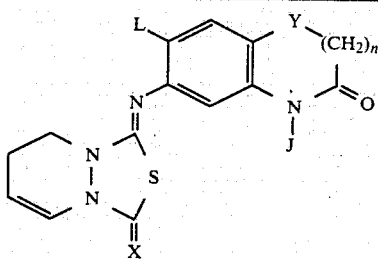

| No. | X | L | Y | n | J |
|---|---|---|---|---|---|
| 1394 | S | F | S | 0 | CH₂CF₃ |
| 1395 | S | F | S | 0 | CH₂Cl |
| 1396 | S | F | S | 0 | CH₂C(Cl)=C(Cl)H |
| 1397 | S | F | S | 0 | CH₂C(Cl)=C(Cl)H (isomer) |
| 1398 | S | F | S | 0 | CH₂C(Cl)=CH₂ |
| 1399 | S | F | S | 0 | CH₂C≡CBr |
| 1400 | S | F | S | 1 | H |
| 1401 | S | F | S | 1 | CH₃ |
| 1402 | S | F | S | 1 | C₂H₅ |
| 1403 | S | F | S | 1 | CH₂CH₂CH₃ |
| 1404 | S | F | S | 1 | CH(CH₃)₂ |
| 1405 | S | F | S | 1 | CH₂(CH₂)₂CH₃ |
| 1406 | S | F | S | 1 | CH-cyclopropyl |
| 1407 | S | F | S | 1 | CH-cyclobutyl |
| 1408 | S | F | S | 1 | CH-cyclopentyl |
| 1409 | S | F | S | 1 | CH-cyclohexyl |
| 1410 | S | F | S | 1 | CH₂-cyclopropyl |
| 1411 | S | F | S | 1 | CH₂-cyclobutyl |
| 1412 | S | F | S | 1 | CH₂-cyclopentyl |
| 1413 | S | F | S | 1 | CH₂-cyclohexyl |

TABLE 2-continued

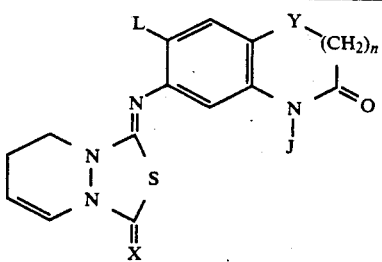

| No. | X | L | Y | n | J |
|---|---|---|---|---|---|
| 1414 | S | F | S | 1 | CH=CH$_2$ |
| 1415 | S | F | S | 1 | CH$_2$CH=CH$_2$ |
| 1416 | S | F | S | 1 | CH$_2$C≡CH |
| 1417 | S | F | S | 1 | CH$_2$OCH$_3$ |
| 1418 | S | F | S | 1 | CH$_2$OC$_2$H$_5$ |
| 1419 | S | F | S | 1 | CH$_2$CH$_2$OCH$_3$ |
| 1420 | S | F | S | 1 | CH$_2$CH$_2$OC$_2$H$_5$ |
| 1421 | S | F | S | 1 | CH$_2$C≡N |
| 1422 | S | F | S | 1 | CH$_2$CO$_2$H |
| 1423 | S | F | S | 1 | CH$_2$CO$_2$CH$_3$ |
| 1424 | S | F | S | 1 | CH$_2$CO$_2$C$_2$H$_5$ |
| 1425 | S | F | S | 1 | CH$_2$CO$_2$CH$_2$CH$_2$CH$_3$ |
| 1426 | S | F | S | 1 | CH$_2$CO$_2$CH(CH$_3$)$_2$ |
| 1427 | S | F | S | 1 | CH$_2$CO$_2$CH$_2$(CH$_2$)$_2$CH$_3$ |
| 1428 | S | F | S | 1 | CH$_2$CO$_2$C(CH$_3$)$_3$ |
| 1429 | S | F | S | 1 | CH$_2$CO$_2$–cyclopropyl |
| 1430 | S | F | S | 1 | CH$_2$CO$_2$–cyclobutyl |
| 1431 | S | F | S | 1 | CH$_2$CO$_2$–cyclopentyl |
| 1432 | S | F | S | 1 | CH$_2$CO$_2$–cyclohexyl |
| 1433 | S | F | S | 1 | CH$_2$CO$_2$CH$_2$–cyclopropyl |
| 1434 | S | F | S | 1 | CH$_2$CO$_2$CH$_2$–cyclobutyl |
| 1435 | S | F | S | 1 | CH$_2$CO$_2$CH$_2$–cyclopentyl |
| 1436 | S | F | S | 1 | CH$_2$CO$_2$CH$_2$–cyclohexyl |
| 1437 | S | F | S | 1 | CH$_2$CH$_2$CO$_2$H |
| 1438 | S | F | S | 1 | CH$_2$CH$_2$CO$_2$CH$_3$ |
| 1439 | S | F | S | 1 | CH$_2$CH$_2$CO$_2$C$_2$H$_5$ |
| 1440 | S | F | S | 1 | CH$_2$CH$_2$CO$_2$CH$_2$CH$_2$CH$_3$ |
| 1441 | S | F | S | 1 | CH$_2$CH$_2$CO$_2$CH(CH$_3$)$_2$ |
| 1442 | S | F | S | 1 | CH$_2$CH$_2$CO$_2$C(CH$_3$)$_3$ |

TABLE 2-continued

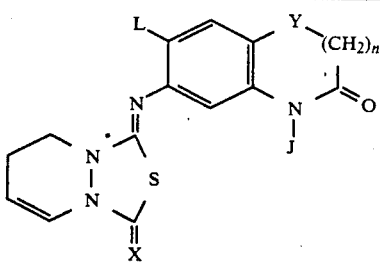

| No. | X | L | Y | n | J |
|---|---|---|---|---|---|
| 1443 | S | F | S | 1 | CH$_2$CH$_2$CO$_2$–cyclopropyl |
| 1444 | S | F | S | 1 | CH$_2$CH$_2$CO$_2$–cyclobutyl |
| 1445 | S | F | S | 1 | CH$_2$CH$_2$CO$_2$–cyclopentyl |
| 1446 | S | F | S | 1 | CH$_2$CH$_2$CO$_2$–cyclohexyl |
| 1447 | S | F | S | 1 | CH$_2$CH$_2$CO$_2$CH$_2$–cyclopropyl |
| 1448 | S | F | S | 1 | CH$_2$CH$_2$CO$_2$CH$_2$–cyclobutyl |
| 1449 | S | F | S | 1 | CH$_2$CH$_2$CO$_2$CH$_2$–cyclopentyl |
| 1450 | S | F | S | 1 | CH$_2$CH$_2$CO$_2$CH$_2$–cyclohexyl |
| 1451 | S | F | S | 1 | CH$_2$CF$_3$ |
| 1452 | S | F | S | 1 | CH$_2$Cl |
| 1453 | S | F | S | 1 | CH$_2$–C(Cl)=C(Cl)(H) |
| 1454 | S | F | S | 1 | CH$_2$–C(Cl)=C(Cl)(H) |
| 1455 | S | F | S | 1 | CH$_2$C(Cl)=CH$_2$ |
| 1456 | S | F | S | 1 | CH$_2$C≡CBr |
| 1457 | O | H | O | 0 | CH$_2$CH=CH$_2$ |
| 1458 | O | H | O | 1 | CH$_2$C≡CH |
| 1459 | O | H | O | 1 | CH$_2$CO$_2$C$_2$H$_5$ |
| 1460 | O | H | S | 0 | C$_2$H$_5$ |
| 1461 | O | H | S | 1 | CH$_2$C≡CH |

TABLE 2-continued

[Structure showing bicyclic compound with substituents L, Y(CH2)n, N, S, X, J]

| No. | X | L | Y | n | J |
|-----|---|---|---|---|---|
| 1462 | O | H | S | 1 | CH₂CO₂-cyclopentyl |
| 1463 | O | H | S | 1 | C₂H₅ |
| 1464 | S | H | O | 0 | CH₂CH=CH₂ |
| 1465 | S | H | O | 1 | CH₂C≡CH |
| 1466 | S | H | O | 1 | C₂H₅ |
| 1467 | S | H | S | 0 | CH-cyclohexyl |
| 1468 | S | H | S | 1 | CH₂C≡N |
| 1469 | S | H | S | 1 | CH₂C(Cl)=CH₂ |
| 1470 | S | H | S | 1 | CH₂C≡CBr |
| 1471 | O | Cl | O | 0 | CH₂CH=CH₂ |
| 1472 | O | Cl | O | 1 | CH₂C≡CH |
| 1473 | O | Cl | O | 1 | CH₂CO₂CH₃ |
| 1474 | O | Cl | S | 0 | C₂H₅ |
| 1475 | S | Cl | S | 1 | CH₂C≡CH |
| 1476 | S | Cl | S | 1 | CH₂CO₂-cyclopentyl |
| 1477 | S | Cl | S | 1 | CH₂C≡N |
| 1478 | O | Br | O | 0 | CH-cyclopentyl |
| 1479 | O | Br | O | 1 | CH₂C(Cl)=CH₂ |
| 1480 | S | Br | S | 0 | H |
| 1481 | S | Br | S | 1 | CH₂C≡CBr |
| 1482 | O | I | O | 1 | C₂H₅ |
| 1483 | S | I | S | 1 | CH₂C≡CH |

When the compound of the present invention is to be used as a herbicide, it is usually mixed with a suitable carrier, for instance, a solid carrier such as clay, talc, bentonite or diatomaceous earth or fine silica powder, or a liquid carrier such as water, an alcohol (such as isopropanol, butanol, benzyl alcohol or furfuryl alcohol), an aromatic hydrocarbon (such as toluene or xylene), an ether (such as anisole), a ketone (such as cyclohexanone or isophorone), an ester (such as butyl acetate), an acid amide (such as N-methylpyrrolidone) or a halogenated hydrocarbon (such as chlorobenzene). If desired, a surfactant, an emulsifier, a dispersant, a penetrating agent, a spreader, a thickener, an anti-freezing agent, a coagulation preventing agent or a stabilizer may be added to prepare an optical formulation such as a liquid formulation, an emulsible concentrate, a wettable powder, a flowable, a granular wettable powder (dry flowable), a dust or a granule.

Further, if desired, other herbicides, various insecticides, bacteriocides, plant regulating agents, synergism agents or antidotes may be incorporated at the time of the preparation of the formulations or at the time of the application of the herbicides. Especially, by the combined use with other herbicides, the cost may be reduced by a reduction in the amount for application, or the herbicidal spectrum can be enlarged or a higher herbicidal effect can be expected due to the synergistic effects of the combined active agents. In such a case, the components of the present invention may be combined with a plurality of known herbicides. Preferred chemicals which may be used in combination with the compounds of the present invention include, for example, bentazone: 3-isopropyl-1H-2,1,3-benzothiadiazin-4(3H)-one 2,2-dioxide, acifluorfen-sodium: sodium 5-[2-chloro-4-(trifluoromethyl)phenoxy]-2-nitrobenzoate, fomesafen: 5-[2-chloro-4-(trifluoromethyl)phenoxy]-N-methylsulfonyl-2-nitrobenzamide, lactofen: 1'-(carboethoxy)ethyl-5-[2-chloro-4-(trifluoromethyl)phenoxy]-2-nitrobenzoate), metribuzin: 4-amino-6-tert-butyl-3-methylthio-1,2,4-triazin-5(4H)one), imazaquin: 2-(4-isopropyl-4-methyl-5-oxo-2-imidazolin-2-yl)quinoline-3-carboxylic acid, sethoxydim: 2-(1-ethoxyiminobutyl)-5-[2-(ethylthio)propyl]-3-hydroxy cyclohex-2-enone), imazethapyr: 5-ethyl-2-(4-isopropyl-4-methyl-5-oxo-2-imidazolin-2-yl)nicotinic acid, cycloxydim: 2-[1-(ethoxyimino)butyl]-3-hydroxy-5-thian-3-ylcyclohex-2-enone), linuron: 3-(3,4-dichlorophenyl)-1-methoxy-1-methylurea, quizalofop-ethyl: ethyl-2-[4-(6-chloro-2-quinoxanyloxy)phenoxy]propionate, dichlofop methyl: methyl-2-[4-(2,4-dichlorophenoxy)phenoxy]propionate, fluazifop-butyl: butyl-2-[4-(5-trifluoromethyl-2-pyridyloxy)phenoxy]propionate, fenoxaprop-ethyl: ethyl-2-[4-(6-chloro-2-benzoxazolyloxy)phenoxy]propionate, haloxyfop-methyl: methyl-2-[4-(3-chloro-5-trifluoromethyl-2-pyridyloxy)phenoxy]propionate, toxaphene: a reaction mixture of chlorinated camphene containing 67–69% chlorine, alachlor: 2-chloro-2',6'-diethyl-N-methoxymethylacetanilide, metolachlor: 2-chloro-N-(2-ethyl-6-methylphenyl)-N-(2-methoxy-1-methylethyl)acetamide, naptalam: N-1-naphtylphthalamic acid, 2,4-DB: 4-(2,4-dichlorophenoxy)butyric acid, MCPB: 4-(4-chloro-2-methylphenoxy)butyric acid, chlorimuron-ethyl: ethyl-2-[3-(4-chloro-6-methoxypyrimidin-2-yl)ureidosulfonyl]benzoate and dimethazone: 2-(2-chlorophenyl)methyl-4,4-dimethyl-3-isoxazolidinone. Other herbicides to be combined with the compound of the present invention includes compounds disclosed in Farm Chemicals Handbook (1987).

The dose varies depending upon the application site, the season for application, the method for application, the type of the crop plant, etc. In general, however, the dose is usually within a range of from 0.001 to 5 kg per hectare as the amount of the active ingredient.

Now, Formulation Examples of the herbicides containing the compounds of the present invention as active ingredients, will be given. However, it should be understood that the present invention is by no means restricted to such specific Examples. In the following Formulation Examples, "parts" means "parts by weight".

Wettable powder

Compound of the present invention: 5–80 parts
Solid carrier: 10–85 parts

Surfactant: 1-10 parts
Others: 1-5 parts
As "others", e.g. a coagulation preventing agent may be mentioned.

Emulsifiable concentrate

Compound of the present invention: 1-30 parts
Liquid carrier: 30-95 parts
Surfactant: 5-15 parts Flowable Compound of the present invention: 5-70 parts
Liquid carrier: 15-65 parts
Surfactant: 5-12 parts
Others: 5-30 parts
As "others", e.g. an anti-freezing agent and a thickener may be mentioned.

Granule

Compound of the present invention: 0.1-10 parts
Solid carrier: 90-99.99 parts
Others: 1-5 parts Granular wettable powder (dry flowable)

Compound of the present invention: 20-90 parts
Solid carrier: 10-60 parts
Surfactant: 1-20 parts

FORMULATION EXAMPLE 1: WETTABLE POWDER

Compound No. 15 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homogeneously pulverized and mixed to form a wettable powder.

FORMULATION EXAMPLE 2: WETTABLE POWDER

Compound No. 137 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homogeneously pulverized and mixed to form a wettable powder.

FORMULATION EXAMPLE 3: WETTABLE POWDER

Compound No. 1074 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homogeneously pulverized and mixed to form a wettable powder.

FORMULATION EXAMPLE 4: WETTABLE POWDER

Compound No. 1302 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homogeneously pulverized and mixed to form a wettable powder.

FORMULATION EXAMPLE 5: WETTABLE POWDER

Compound No. 1074 of the present invention: 40 parts
Zeeklite PFP (tradename for a kaolin-type clay, manufactured by Zeeklite Industries, Co., Ltd.): 53 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homogeneously pulverized and mixed to form a wettable powder.

FORMULATION EXAMPLE 6: EMULSIFIABLE CONCENTRATE

Compound No. 15 of the present invention: 3 parts
Xylene: 76 parts
Isophorone: 15 parts Sorpol 3005X (tradename for a mixture of a nonionic surfactant and an anionic surfactant, manufactured by Toho Chemical Co., Ltd.): 6 parts The above ingredients are homogeneously mixed to obtain an emulsifiable concentrate.

FORMULATION EXAMPLE 7: EMULSIFIABLE CONCENTRATE

Compound No. 1074 of the present invention: 3 parts
Xylene: 76 parts
Isophorone: 15 parts
Sorpol 3005X (tradename for a mixture of a nonionic surfactant and an anionic surfactant, manufactured by Toho Chemical Co., Ltd.): 6 parts The above ingredients are homogeneously mixed to obtain an emulsifiable concentrate.

FORMULATION EXAMPLE 8: EMULSIFIABLE CONCENTRATE

Compound No. 1302 of the present invention: 3 parts
Xylene: 76 parts
Isophorone: 15 parts
Sorpol 3005X (tradename for a mixture of a nonionic surfactant and an anionic surfactant, manufactured by Toho Chemical Co., Ltd.): 6 parts The above ingredients are homogeneously mixed to obtain an emulsifiable concentrate.

FORMULATION EXAMPLE 9: FLOWABLE

Compound No. 15 of the present invention: 35 parts
Agrizole S-711 (tradename for a nonionic surfactant, manufactured by Kao Corporation): 8 parts
Runox 1000C (tradename for an anionic surfactant, manufactured by Toho Chemical, Co., Ltd.): 0.5 parts
1% Rodopol water (tradename for a thickener, manufactured by Rhone-Poulenc): 20 parts
Ethylene glycol (anti-freezing agent): 8 parts
Water: 28.5 parts The above ingredients are homogeneously mixed to form a flowable.

FORMULATION EXAMPLE 10: FLOWABLE

Compound No. 1074 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 parts
1% Rodopol water (tradename for a thickener, manufactured by Rhone-Poulenc): 20 parts
Ethylene glycol (anti-freezing agent): 8 parts
Water: 28.5 parts The above ingredients are homogeneously mixed to form a flowable.

FORMULATION EXAMPLE 11: FLOWABLE

Compound No. 1302 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 parts
1% Rodopol water (tradename for a thickener, manufactured by Rhone-Poulenc): 20 parts
Ethylene glycol (anti-freezing agent): 8 parts
Water: 28.5 parts The above ingredients are homogeneously mixed to form a flowable.

FORMULATION EXAMPLE 12: GRANULE

Compound No. 1074 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 13: GRANULE

Compound No. 1302 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 14: WETTABLE POWDER

Compound No. 65 of the present invention: 50 parts
Zeeklite PFP (tradename for a kaolin-type clay, manufactured by Zeeklite Industries, Co., Ltd.): 43 parts
Sorpol 5050 (tradename for an anionic surfactant), manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder manufactured by Shionogi Pharmaceutical Co., Ltd.): 2 parts The above ingredients are homegenously pulverized and mixed to form a wettable powder.

FORMULATION EXAMPLE 15: WETTABLE POWDER

Compound No. 68 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homogenously pulverized and mixed to form a wettable powder.

FORMULATION EXAMPLE 16: WETTABLE POWDER

Compound No. 183 of the present invention: 50 parts
Zeeklite PFP (tradename for a kaolin-type clay, manufactured by Zeeklite Industries, Co., Ltd.): 43 parts Sorpol 5050 (tradename for an anionic surfactant, manufactured by Toho Chemical Co., Ltd.): 2 parts Runox 1000C (tradename for an anionic surfactant, manufactured by Toho Chemical Co., Ltd.): 3 parts Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 17: WETTABLE POWDER

Compound No. 184 of the present invention: 50 parts

Zeeklite PFP (tradename for a kaolin-type clay, manufactured by Zeeklite Industries, Co., Ltd.): 43 parts Sorpol 5050 (tradename for an anionic surfactant, manufactured by Toho Chemical Co., Ltd.): 2 parts Runox 1000C (tradename for an anionic surfactant, manufactured by Toho Chemical Co., Ltd.): 3 parts Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 18: WETTABLE POWDER

Compound No. 190 of the present invention: 40 parts

Zeeklite PFP (tradename for a kaolin-type clay, manufactured by Zeeklite Industries, Co., Ltd.): 53 parts Sorpol 5050 (tradename for an anionic surfactant, manufactured by Toho Chemical Co., Ltd.): 2 parts Runox 1000C (tradename for an anionic surfactant, manufactured by Toho Chemical Co., Ltd.): 3 parts Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 19: EMULSIFIABLE CONCENTRATE

Compound No. 65 of the present invention: 3 parts

Xylene 76 parts

Cyclohexanone: 15 parts

Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 20: EMULSIFIABLE CONCENTRATE

Compound No. 183 of the present invention: 3 parts

Xylene: 76 parts

Cyclohexanone: 15 parts

Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 21: EMULSIFIABLE CONCENTRATE

Compound No. 190 of the present invention: 3 parts

Xylene: 76 parts

Isophorone: 15 parts

Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 22: EMULSIFIABLE CONCENTRATE

Compound No. 68 of the present invention: 3 parts

Xylene: 76 parts

Isophorone: 15 parts

Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 23: FLOWABLE

Compound No. 62 of the present invention: 35 parts

Agrizole S-711 (tradename for a nonionic surfactant, manufactured by Kao Corporation): 8 parts Runox 1000C (tradename for an anionic surfactant, manufactured by Toho Chemical Co., Ltd.): 0.5 part 1% Rodopol water (tradename for a thickener, manufactured by Rhone-Poulenc): 20 parts Ethylene grycol (anti-freezing agent): 8 parts Water: 28.5 parts The above ingredients are homegenously mixed to obtain a flowable.

FORMULATION EXAMPLE 24: FLOWABLE

Compound No. 68 of the present invention: 35 parts

Agrizole S-711 (tradename for a nonionic surfactant, manufactured by Kao Corporation): 8 parts Runox 1000C (tradename for an anionic surfactant, manufactured by Toho Chemical Co., Ltd.): 0.5 part 1% Rodopol water (tradename for a thickener, manufactured by Rhone-Poulenc): 20 parts Ethylene grycol (anti-freezing agent): 8 parts Water: 28.5 parts The above ingredients are homegenously mixed to obtain a flowable.

FORMULATION EXAMPLE 25: FLOWABLE

Compound No. 183 of the present invention: 35 parts

Agrizole S-711 (tradename for a nonionic surfactant, manufactured by Kao Corporation): 8 parts Runox 1000C (tradename for an anionic surfactant, manufactured by Toho Chemical Co., Ltd.): 0.5 part 1% water (tradename for a thickener, manufactured by Rhone-Poulenc): 20 parts Ethylene grycol (anti-freezing agent): 8 parts Water: 28.5 parts The above ingredients are homegenously mixed to obtain a flowable.

FORMULATION EXAMPLE 26: FLOWABLE

Compound No. 184 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 8 parts
Water: 28.5 parts The above ingredients are homegenously mixed to obtain a flowable.

FORMULATION EXAMPLE 27: FLOWABLE

Compound No. 190 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 8 parts
Water: 28.5 parts The above ingredients are homegenously mixed to obtain a flowable.

FORMULATION EXAMPLE 28: GRANULE

Compound No. 61 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 29: GRANULE

Compound No. 190 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 30: GRANULE

Compound No. 86 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 31: WETTABLE POWDER

Compound No. 28 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 32: WETTABLE POWDER

Compound No. 86 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 33: WETTABLE POWDER

Compound No. 570 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 34: WETTABLE POWDER

Compound No. 644 of the present invention: 50 parts
Zeeklite PFP (tradename for a kaolin-type clay, manufactured by Zeeklite Industries, Co., Ltd.): 43 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 35: WETTABLE POWDER

Compound No. 773 of the present invention: 40 parts
Zeeklite PFP (tradename for a kaolin-type clay, manufactured by Zeeklite Industries, Co., Ltd.): 53 parts
Sorpol 5050 (tradename for an anionic surfactant, manufactured by Toho Chemical Co., Ltd.): 2 parts
Runox 1000C (tradename for an anionic surfactant, manufactured by Toho Chemical Co., Ltd.): 3 parts
Carplex #80 (tradename for coagulation-preventing agent composed of a mixture of a surfactant and fine silica powder, manufactured by Shionogi Pharmaceutical Co., Ltd.): 2 parts The above ingredients are homegenously pulverized and mixed to form a wettable powder.

FORMULATION EXAMPLE 36: EMULSIFIABLE CONCENTRATE

Compound No. 64 of the present invention: 3 parts
Xylene: 76 parts
Cyclohexanone: 15 parts
Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 37: EMULSIFIABLE CONCENTRATE

Compound No. 201 of the present invention: 3 parts
Xylene: 76 parts
Cyclohexanone: 15 parts
Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 38: EMULSIFIABLE CONCENTRATE

Compound No. 577 of the present invention: 3 parts
Xylene: 76 parts
Isophorone: 15 parts
Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 39: EMULSIFIABLE CONCENTRATE

Compound No. 640 of the present invention: 3 parts
Xylene: 76 parts
Isophorone: 15 parts
Sorpol 3005X (tradename for a mixture of a nonionic surfactant and an anionic surfactant, manufactured by Toho Chemical Co., Ltd.): 6 parts The above ingredients are homegenously mixed to obtain an emulsifiable concentrate.

FORMULATION EXAMPLE 40: FLOWABLE

Compound No. 308 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 8 parts
Water: 28.5 parts The above ingredients are homegenously mixed to obtain a flowable.

FORMULATION EXAMPLE 41: FLOWABLE

Compound No. 613 of the present invention: 35 parts
Agrizole S-711 (tradename for a nonionic surfactact, manufactured by Kao Corporation): 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 8 parts
Water: 28.5 parts The above ingredients are homegenously mixed to obtain a flowable.

FORMULATION EXAMPLE 42: FLOWABLE

Compound No. 661 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 8 parts
Water: 28.5 parts The above ingredients are homegenously mixed to obtain a flowable.

FORMULATION EXAMPLE 43: FLOWABLE

Compound No. 686 of the present invention: 35 parts
Agrizole S-711 (tradename for a nonionic surfactant, manufactured by Kao Corporation: 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 8 parts
Water: 8 parts The above ingredients are homegenously mixed to obtain a flowable.

FORMULATION EXAMPLE 44: FLOWABLE

Compound No. 800 of the present invention: 35 parts
Agrizole S-711 (tradename for a nonionic surfactant, manufactured by Kao Corporation): 8 parts
Runox 1000C (tradename for an anionic surfactant, manufactured by Toho Chemical Co., Ltd.): 0.5 part
1% Rodopol water (tradename for a thickener, manufactured by Rhone-Poulenc): 20 parts
Ethylene grycol (anti-freezing agent): 4 parts
Water: 28.5 parts The above ingredients are homegenously mixed to obtain a flowable.

FORMULATION EXAMPLE 45: GRANULE

Compound No. 308 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 46: GRANULE

Compound No. 613 of the present invention: 0.1 part
Bentonite: 55.0 parts
Talc: 44.9 parts The above ingredients are uniformly mixed and pulverized. A small amount of water is added thereto, and the mixture is stirred, mixed and kneaded, and then granurated by an extrusion granulator, followed by drying to obtain a granule.

FORMULATION EXAMPLE 47: GRANULAR WETTABLE POWDER (DRY FLOWABLE)

Compound No. 61 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename for coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 48: GRANULAR WETTABLE POWDER (DRY FLOWABLE)

Compound No. 62 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename for coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 49: GRANULAR WETTABLE POWDER (DRY FLOWABLE)

Compound No. 183 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename for coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 50: GRANULAR WETTABLE POWDER (DRY FLOWABLE)

Compound No. 201 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename for coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 51: Granular wettable powder (dry flowable)

Compound No. 308 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename for coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 52: Granular wettable powder (dry flowable)

Compound No. 612 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename for coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 53: GRANULAR WETTABLE POWDER (DRY FLOWABLE)

Compound No. 620 of the present invention: 75 parts
Isobam No. 1 (tradename for an anionic surfactant, manufactured by Kuraray Isoprene Chemical Co., Ltd.): 10 parts
Vanilex N (tradename for an anionic surfactant, manufactured by Sanyo Kokusaku Pulp K.K.): 5 parts
Carplex #80 (tradename coagulation-preventing agent composed of a mixture of a surfactant and fine silica powder, manufactured by Shionogi Pharmaceutical Co., Ltd.): 10 parts The above ingredients are homegenously finely pulverized and mixed to form a dry flowable.

FORMULATION EXAMPLE 54: GRANULAR WETTABLE POWDER (DRY FLOWABLE)

Compound No. 640 of the present invention: 75 parts
Isobam No. 1 (tradename for an anionic surfactant, manufactured by Kuraray Isoprene Chemical Co., Ltd.): 10 parts Vanilex N (tradename for an anionic surfactant, manufactured by Sanyo Kokusaku Pulp K.K.): 5 parts Carplex #80 (tradename for coagulation-preventing agent composed of a mixture of a surfactant and fine silica powder, manufactured by Shionogi Pharmaceutical Co., Ltd.): 10 parts The above ingredients are homogenously finely pulverized and mixed to form a dry flowable.

FORMULATION EXAMPLE 55: GRANULAR WETTABLE POWDER (DRY FLOWABLE)

Compound No. 686 of the present invention: 75 parts

Isobam No. 1 (tradename for an anionic surfactant, manufactured by Kuraray Isoprene Chemical Co., Ltd.): 10 parts Vanilex N (tradename for an anionic surfactant, manufactured by Sanyo Kokusaku Pulp K.K.): 5 parts Carplex #80 (tradename for coagulation-preventing agent composed of a mixture of a surfactant and fine silica powder, manufactured by Shionogi Pharmaceutical Co., Ltd.): 10 parts The above ingredients are homogenously finely pulverized and mixed to form a dry flowable.

FORMULATION EXAMPLE 56: GRANULAR WETTABLE POWDER (DRY FLOWABLE)

Compound No. 731 of the present invention: 75 parts

Isobam No. 1 (tradename for an anionic surfactant, manufactured by Kuraray Isoprene Chemical Co., Ltd.): 10 parts Vanilex N (tradename for an anionic surfactant, manufactured by Sanyo Kokusaku Pulp K.K.): 5 parts Carplex #80 (tradename for coagulation-preventing agent composed of a mixture of a surfactant and fine silica powder, manufactured by Shionogi Pharmaceutical Co., Ltd.): 10 parts The above ingredients are homogenously finely pulverized and mixed to form a dry flowable.

FORMULATION EXAMPLE 57: GRANULAR WETTABLE POWDER (DRY FLOWABLE)

Compound No. 822 of the present invention: 75 parts

Isobam No. 1 (tradename for an anionic surfactant, manufactured by Kuraray Isoprene Chemical Co., Ltd.): 10 parts Vanilex N (tradename for an anionic surfactant, manufactured by Sanyo Kokusaku Pulp K.K.): 5 parts Carplex #80 (tradename for coagulation-preventing agent composed of a mixture of a surfactant and fine silica powder, manufactured by Shionogi Pharmaceutical Co., Ltd.): 10 parts The above ingredients are homogenously finely pulverized and mixed to form a dry flowable.

FORMULATION EXAMPLE 58: GRANULAR WETTABLE POWDER (DRY FLOWABLE)

Compound No. 1074 of the present invention: 75 parts

Isobam No. 1 (tradename for an anionic surfactant, manufactured by Kuraray Isoprene Chemical Co., Ltd.): 10 parts Vanilex N (tradename for an anionic surfactant, manufactured by Sanyo Kokusaku Pulp K.K.): 5 parts Carplex #80 (tradename for coagulation-preventing agent composed of a mixture of a surfactant and fine silica powder, manufactured by Shionogi Pharmaceutical Co., Ltd.): 10 parts The above ingredients are homogenously finely pulverized and mixed to form a dry flowable.

In their use, the above wettable powders, dry flowables, emulsifireble concentrations or flowables are diluted with water from 50 to 1,000 times and applied so that the respective active ingredients will be from 0.001 to 5 kg per hectare.

The compounds of the present invention are applicable not only to agricultural fields such as upland fields, paddy fields and orchards, but also to non-agricultural fields such as athletic fields, vacant fields and railway sides for the control of various weeds. The dose in their application varies depending upon the application site, the season for application, the type of weeds to be controlled, the type of crop plants, etc. However, it is usually within a range of from 0.001 to 5 kg per hectare.

Now, the herbicidal activities of the compounds of the present invention will be described with respect to specific Test Examples.

TEST EXAMPLE 1: TEST ON THE HERBICIDAL EFFECTS IN SOIL TREATMENT

A plastic box having a length of 15 cm, a width of 22 cm and a depth of 6 cm was filled with a sterilized diluvial soil, and seeds of *Echinochloa crus-galli*, *Digitaria adscendens*, *Cyperus microiria*, *Solanum nigrum*, *Galinsoga ciliate*, *Rorippa indica*, *Zea mays* and *Glycine max* were sown. The soil was covered thereon in the thickness of about 1 cm, and then a herbicide solution was applied onto the surface of the soil uniformly so that the active ingredient was distributed at a predetermined concentration. The herbicide solution was prepared by diluting the wettable powder, the emulsifiable concentrate, the dry flowable or the flowable as described in the foregoing Formulation Examples with water and applied onto the entire soil surface by means of a small spray.

Three weeks after the application of the herbicidal solution, the herbicidal effects against each weed and *Zea mays* and *Glycine max* were determined on the basis of the following standard ratings. The results thereby obtained are shown in Table 3. Some of the compounds of the present invention have selectively for certain crop plants.

Standard ratings

5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate (\%)} = \left(1 - \frac{T}{N}\right) \times 100$$

where

T: Weight of the weed growth above the soil surface of the treated area

N: Weight of the weed grown above the soil surface of the non-treated area

TEST EXAMPLE 2: TEST ON THE HERBICIDAL EFFECTS IN FOLIAGE TREATMENT

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliate* and *Rorippa indica* were spot-wisely sown. Then, the soil was covered thereon in a thickness of about 1 cm. When the various plants grew to the 2 or 3 leaf stage, a herbicidal solution was uniformly sprayed on the foliages so that the active ingredient was applied in a predetermined concentration.

The herbicidal solution was prepared by diluting the wettable powder, the emulsifiable concentrate, the dry flowable or the flowable as described in the above Formulation Examples with water and applied onto the entire surface of the foliages of the weeds and the crop plants by a small spray. Four weeks after the application of the herbicide solution, the herbicidal effects against each weed were determined on the basis of the standard ratings described in Test Example 1. The results are shown in Table 4.

TEST EXAMPLE 3: TEST ON THE HERBICIDAL EFFECTS IN AN IRRIGATED CONDITION

A 1/5,000 are Wagner pot was filled with alluvial soil. Water was introduced and mixed to form an irrigated condition with water depth of 2 cm. Seeds of *Echinochloa oryzicola, Monochoria vaginalis, Rotala indica* and *Scirpus juncoides* were sown, and tubers of *Sagittaria pygmaea* were planted. Further, rice seedlings of 2.5 leaf stage were transplanted. Then, the pot was kept in a green house at a temperature of from 25° to 30° C. for the cultivation of the plants. Three days later, a diluted herbicidal solution was dropwise applied to the water surface in a predetermined dose by a measuring pipette. Three weeks after the dropwise application of the herbicide, the herbicidal effects against various weeds and rice were determined on the basis of the standard ratings described in Test Example 1. The results are shown in Table 5.

TEST EXAMPLE 4: TEST ON THE HERBICIDAL EFFECTS IN SOIL TREATMENT

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliate, Rorippa indicia, Oryza sativa, Zea mays Triticum aestivum, Glycine max* and *Cossipium herbaceum* were sown. The soil was covered thereon in the thickness of about 1 cm, and a herbicide solution was applied onto the surface of the soil uniformly so that the active ingredient was distributed at a predetermined concentration. The herbicide solution was prepared by diluting the wettable powder, the emulsifiable concentrate, the dry flowable or the flowable as described in the foregoing Formulation Examples with water and applied onto the entire soil surface by means of a small spray.

Three weeks after the application of the herbicidal solution, the herbicidal effects against each weed and *Oryza sativa, Zea mays, Triticum aestivum, Glycine max* and *Cossipium herbaceum* were determined on the basis of the standard ratings described in Test Example 1. The results thereby obtained are shown in Table 6.

TEST EXAMPLE 5: TEST ON THE HERBICIDAL EFFECTS IN FOLIAGE TREATMENT

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliate, Rorippa indica, Oryza sativa, Zea mays, Triticum aestivum* and *Glycine max* were spot-wisely sown. Then, the soil was covered thereon in a thickness of about 1 cm. When the various plants grew to the 2 or 3 leaf stage, a herbicidal solution was uniformly sprayed on the foliages so that the active ingredient was applied in a predetermined concentration.

The herbicidal solution was prepared by diluting the wettable powder, the emulsifiable concentrate, the dry folowable or the flowable as described in the above Formulation Examples with water and applied onto the entire surface of the foliages of the weeds and the crop plants by a small spray. Four weeks after the application of the herbicide solution, the herbicidal effects against each weed and phytotoxicity against each crop plant were determined on the basis of the standard ratings described in Test Example 1. The results are shown in Table 7.

TEST EXAMPLE 6: TEST FOR APPLICATION DURING CULTIVATION OF SOYBEAN (FOLIAGE TREATMENT)

A plastic box having a length of 30 cm, a width of 28 cm and a depth of 12 cm was filled with a sterilized diluvial soil, and seeds of *Glycine max, Xanthium pensylvanicum, Datura stramonium, Ipomoea purpurea, Abutilon theophrasti, Sida spinosa, Amaranthus retroflexus* and *Chenopodium album* were spot-wisely sown. Then, the soil was covered thereon in a thickness of about 1.5 cm. When the various plants grew to the 2 or 3 leaf stage, a herbicidal solution waw uniformly sprayed on the foliages so that the active ingredient is applied in a predetermined concentration.

The herbicidal solution was prepared by diluting the wettable powder, the emulsifiable concentrate, the dry folowable or the flowable as described in the above Formulation Examples with water and applied onto the entire surface of the foliages of the weeds and the crop plants by a small spray. Three weeks after the application of the herbicide solution, the herbicidal effects against each weed and the phytotoxicity against each crop plant were determined on the basis of the standard ratings described in Test Example 1. The results are shown in Table 8.

The symbols used in the following Tables have the following meanings:

| | | |
|---|---|---|
| N: | barnyardgrass: | *Echinochloa crus-galli* |
| M: | crabgrass: | *Digitaria adscendens* |
| K: | annual sedge: | *Cyperus microiria* |
| H: | black nightshade: | *Solanum nigrum* |
| D: | hairy galinsoga: | *Galinsoga ciliate* |
| I: | fieldcress: | *Rorippa indica* |
| R: | rice: | *Oryza sativa* |
| T: | corn: | *Zea mays* |
| W: | wheat: | *Triticum aestivum* |
| S,(8): | soybean: | *Glycine max* |
| C: | cotton: | *Cossipium herbaceum* |
| B: | sugar beet: | *Beta vulgaris* |
| (1): | common cocklebur: | *Xanthium pensylvanicum* |
| (2): | jimsonweed: | *Datura stramonium* |
| (3): | tall morningglory: | *Ipomoea purpurea* |
| (4): | velvetleaf: | *Abutilon theophrasti* |

-continued

| | | |
|---|---|---|
| (5): | prickly sida: | *Sida spinosa* |
| (6): | redroot pigweed: | *Amaranthus retroflexus* |
| (7): | common lambsquarters: | *Chenopodium album* |
| (8): | bulrush: | *Scirpus juncoides* |
| (9): | ducksalad: | *Monochoria Vaginalis* |
| (10): | toothcup | *Rotala indica* |
| (11): | arrowhead: | *Sagittaria pygmaea* |

Comparative compounds A and B referred to in Tables 3, 4, 5 and 8 are as follows:

Comparative compound A: benazolin

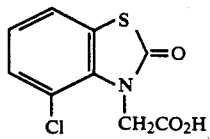

Comparative compound B: acifluorfen-sodium

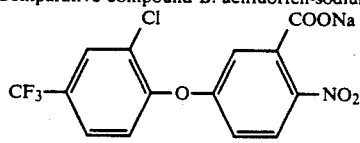

TABLE 3

| Compound No. | Amount (Kg/ha) | N | M | K | H | D | I | T | S |
|---|---|---|---|---|---|---|---|---|---|
| 15 | 0.02 | 4 | 4 | 5 | 5 | 5 | 5 | 0 | 0 |
| | 0.04 | 5 | 5 | 5 | 5 | 5 | 5 | 0 | 0 |
| | 0.08 | 5 | 5 | 5 | 5 | 5 | 5 | 0 | 0 |
| 137 | 0.02 | 4 | 3 | 5 | 5 | 5 | 5 | 0 | 0 |
| | 0.04 | 5 | 4 | 5 | 5 | 5 | 5 | 0 | 0 |
| | 0.08 | 5 | 5 | 5 | 5 | 5 | 5 | 0 | 0 |
| 1074 | 0.01 | 3 | 3 | 4 | 5 | 5 | 5 | 0 | 0 |
| | 0.02 | 4 | 4 | 5 | 5 | 5 | 5 | 0 | 0 |
| | 0.04 | 5 | 5 | 5 | 5 | 5 | 5 | 0 | 0 |
| 1302 | 0.02 | 2 | 2 | 4 | 5 | 5 | 5 | 0 | 0 |
| | 0.04 | 3 | 3 | 5 | 5 | 5 | 5 | 0 | 0 |
| | 0.08 | 4 | 4 | 5 | 5 | 5 | 5 | 0 | 0 |
| Comparative compound A | 0.16 | 0 | 0 | 0 | 0 | 0 | 0 | 0 | 0 |
| | 0.32 | 0 | 0 | 1 | 2 | 1 | 2 | 0 | 0 |
| | 0.63 | 1 | 0 | 3 | 3 | 2 | 3 | 0 | 1 |

TABLE 4

| Compound No. | Amount (Kg/ha) | N | M | K | H | D | I |
|---|---|---|---|---|---|---|---|
| 15 | 0.02 | 2 | 1 | 3 | 5 | 5 | 5 |
| | 0.04 | 4 | 2 | 4 | 5 | 5 | 5 |
| | 0.08 | 5 | 3 | 5 | 5 | 5 | 5 |
| 137 | 0.02 | 2 | 1 | 3 | 5 | 5 | 5 |
| | 0.04 | 4 | 2 | 4 | 5 | 5 | 5 |
| | 0.08 | 5 | 3 | 5 | 5 | 5 | 5 |
| 1074 | 0.02 | 3 | 2 | 3 | 5 | 5 | 5 |
| | 0.04 | 4 | 3 | 4 | 5 | 5 | 5 |
| | 0.08 | 5 | 4 | 5 | 5 | 5 | 5 |
| 1302 | 0.02 | 2 | 2 | 3 | 5 | 5 | 5 |
| | 0.04 | 3 | 3 | 4 | 5 | 5 | 5 |
| | 0.08 | 5 | 4 | 5 | 5 | 5 | 5 |
| Comparative compound A | 0.16 | 0 | 0 | 0 | 0 | 0 | 1 |
| | 0.32 | 0 | 0 | 0 | 1 | 1 | 2 |
| | 0.63 | 0 | 0 | 0 | 3 | 3 | 3 |

TABLE 5

| Compound No. | Amount (Kg/ha) | N | (8) | (9) | (10) | (11) | R* |
|---|---|---|---|---|---|---|---|
| 15 | 0.01 | 5 | 4 | 5 | 5 | 5 | 0 |
| | 0.02 | 5 | 5 | 5 | 5 | 5 | 0 |
| | 0.04 | 5 | 5 | 5 | 5 | 5 | 1 |
| 86 | 0.01 | 5 | 3 | 5 | 5 | 2 | 0 |
| | 0.02 | 5 | 5 | 5 | 5 | 3 | 0 |
| | 0.04 | 5 | 5 | 5 | 5 | 5 | 1 |
| 137 | 0.01 | 4 | 4 | 5 | 5 | 5 | 0 |
| | 0.02 | 5 | 5 | 5 | 5 | 5 | 0 |
| | 0.04 | 5 | 5 | 5 | 5 | 5 | 1 |
| 577 | 0.01 | 4 | 4 | 5 | 5 | 5 | 0 |
| | 0.02 | 5 | 5 | 5 | 5 | 5 | 0 |
| | 0.04 | 5 | 5 | 5 | 5 | 5 | 1 |
| 644 | 0.01 | 5 | 4 | 5 | 5 | 4 | 0 |
| | 0.02 | 5 | 5 | 5 | 5 | 5 | 0 |
| | 0.04 | 5 | 5 | 5 | 5 | 5 | 1 |
| 1074 | 0.01 | 5 | 4 | 5 | 5 | 5 | 0 |
| | 0.02 | 5 | 5 | 5 | 5 | 5 | 0 |
| | 0.04 | 5 | 5 | 5 | 5 | 5 | 1 |
| 1302 | 0.01 | 5 | 4 | 5 | 5 | 5 | 0 |
| | 0.02 | 5 | 5 | 5 | 5 | 5 | 0 |
| | 0.04 | 5 | 5 | 5 | 5 | 5 | 1 |
| Comparative compound A | 0.16 | 0 | 0 | 4 | 0 | — | 0 |
| | 0.32 | 0 | 0 | 5 | 1 | — | 0 |
| | 0.63 | 1 | 1 | 5 | 1 | — | 0 |

R*: transplanted

TABLE 6

| Compound No. | Amount (kg/ha) | N | M | K | H | D | I | R | T | W | S | C |
|---|---|---|---|---|---|---|---|---|---|---|---|---|
| 64 | 0.04 | 1 | 1 | 3 | 5 | 3 | 5 | 0 | 0 | 0 | 0 | 0 |
| | 0.08 | 2 | 2 | 4 | 5 | 4 | 5 | 0 | 0 | 0 | 0 | 0 |
| | 0.16 | 3 | 3 | 5 | 5 | 5 | 5 | 1 | 0 | 0 | 0 | 0 |
| 68 | 0.04 | 3 | 2 | 3 | 5 | 5 | 5 | 0 | 0 | 0 | 0 | 0 |
| | 0.08 | 4 | 3 | 4 | 5 | 5 | 5 | 0 | 0 | 0 | 0 | 0 |
| | 0.16 | 5 | 4 | 5 | 5 | 5 | 5 | 0 | 0 | 0 | 0 | 0 |
| 86 | 0.04 | 3 | 4 | 4 | 5 | 3 | 5 | 0 | 0 | 0 | 0 | 0 |
| | 0.08 | 4 | 5 | 5 | 5 | 4 | 5 | 0 | 0 | 0 | 0 | 0 |
| | 0.16 | 5 | 5 | 5 | 5 | 5 | 5 | 0 | 0 | 0 | 0 | 0 |
| 190 | 0.04 | 3 | 2 | 3 | 5 | 5 | 5 | 0 | 0 | 0 | 0 | 0 |
| | 0.08 | 4 | 3 | 4 | 5 | 5 | 5 | 0 | 0 | 0 | 0 | 0 |
| | 0.16 | 5 | 4 | 5 | 5 | 5 | 5 | 0 | 0 | 0 | 0 | 0 |
| 577 | 0.04 | 4 | 5 | 5 | 5 | 5 | 5 | 0 | 0 | 0 | 0 | 0 |
| | 0.08 | 5 | 5 | 5 | 5 | 5 | 5 | 0 | 0 | 0 | 0 | 0 |
| | 0.16 | 5 | 5 | 5 | 5 | 5 | 5 | 1 | 0 | 0 | 0 | 0 |
| 582 | 0.04 | 1 | 3 | 4 | 5 | 3 | 5 | 0 | 0 | 0 | 0 | 0 |
| | 0.08 | 2 | 4 | 5 | 5 | 4 | 5 | 0 | 0 | 0 | 0 | 0 |
| | 0.16 | 3 | 5 | 5 | 5 | 5 | 5 | 1 | 0 | 1 | 0 | 0 |
| 583 | 0.04 | 2 | 5 | 5 | 5 | 5 | 5 | 0 | 0 | 0 | 0 | 0 |
| | 0.08 | 3 | 5 | 5 | 5 | 5 | 5 | 0 | 0 | 0 | 0 | 0 |
| | 0.16 | 4 | 5 | 5 | 5 | 5 | 5 | 1 | 1 | 0 | 0 | 0 |
| 584 | 0.04 | 1 | 3 | 2 | 5 | 3 | 5 | 0 | 0 | 0 | 0 | 0 |
| | 0.08 | 2 | 4 | 3 | 5 | 4 | 5 | 0 | 0 | 0 | 0 | 0 |
| | 0.16 | 3 | 5 | 4 | 5 | 5 | 5 | 0 | 0 | 0 | 0 | 0 |
| 606 | 0.04 | 3 | 4 | 3 | 5 | 3 | 5 | 0 | 0 | 0 | 0 | 0 |
| | 0.08 | 4 | 5 | 4 | 5 | 4 | 5 | 0 | 0 | 0 | 0 | 0 |
| | 0.16 | 5 | 5 | 5 | 5 | 5 | 5 | 0 | 0 | 0 | 0 | 0 |
| 618 | 0.04 | 3 | 2 | 3 | 5 | 4 | 5 | 0 | 0 | 0 | 0 | 0 |
| | 0.08 | 4 | 3 | 4 | 5 | 5 | 5 | 0 | 0 | 0 | 0 | 0 |
| | 0.16 | 5 | 4 | 5 | 5 | 5 | 5 | 0 | 0 | 0 | 0 | 0 |
| 639 | 0.04 | 3 | 3 | 3 | 5 | 4 | 5 | 0 | 0 | 0 | 0 | 0 |
| | 0.08 | 4 | 4 | 4 | 5 | 5 | 5 | 0 | 0 | 0 | 0 | 0 |
| | 0.16 | 5 | 5 | 5 | 5 | 5 | 5 | 1 | 0 | 0 | 0 | 0 |
| 661 | 0.04 | 5 | 5 | 4 | 5 | 5 | 5 | 0 | 0 | 0 | 0 | 0 |
| | 0.08 | 5 | 5 | 5 | 5 | 5 | 5 | 0 | 0 | 0 | 0 | 0 |
| | 0.16 | 5 | 5 | 5 | 5 | 5 | 5 | 0 | 0 | 0 | 0 | 0 |
| 675 | 0.04 | 1 | 3 | 2 | 5 | 4 | 5 | 0 | 0 | 0 | 0 | 0 |
| | 0.08 | 2 | 5 | 3 | 5 | 5 | 5 | 0 | 0 | 0 | 0 | 0 |
| | 0.16 | 3 | 5 | 4 | 5 | 5 | 5 | 0 | 0 | 0 | 0 | 0 |
| 800 | 0.04 | 2 | 2 | 3 | 5 | 3 | 5 | 0 | 0 | 0 | 0 | 0 |
| | 0.08 | 3 | 3 | 4 | 5 | 4 | 5 | 0 | 0 | 0 | 0 | 0 |
| | 0.16 | 4 | 4 | 5 | 5 | 5 | 5 | 0 | 0 | 0 | 0 | 0 |
| 822 | 0.04 | 1 | 2 | 1 | 5 | 3 | 5 | 0 | 0 | 0 | 0 | 0 |
| | 0.08 | 2 | 3 | 2 | 5 | 4 | 5 | 0 | 0 | 0 | 0 | 0 |
| | 0.16 | 3 | 4 | 3 | 5 | 5 | 5 | 0 | 0 | 0 | 0 | 0 |

TABLE 7

| Compound No. | Amount (kg/ha) | N | M | K | H | D | I | R | T | W | S |
|---|---|---|---|---|---|---|---|---|---|---|---|
| 64 | 0.02 | 3 | 2 | 3 | 5 | 4 | 5 | 1 | 0 | 0 | 0 |
|  | 0.04 | 4 | 3 | 4 | 5 | 5 | 5 | 2 | 1 | 0 | 0 |
|  | 0.08 | 5 | 4 | 5 | 5 | 5 | 5 | 3 | 2 | 0 | 1 |
| 68 | 0.04 | 4 | 2 | 3 | 5 | 5 | 5 | 0 | 0 | 0 | 0 |
|  | 0.08 | 5 | 3 | 4 | 5 | 5 | 5 | 1 | 1 | 0 | 0 |
|  | 0.16 | 5 | 4 | 5 | 5 | 5 | 5 | 2 | 2 | 0 | 1 |
| 86 | 0.02 | 4 | 2 | 4 | 5 | 5 | 5 | 0 | 0 | 0 | 1 |
|  | 0.04 | 5 | 3 | 5 | 5 | 5 | 5 | 0 | 1 | 0 | 2 |
|  | 0.08 | 5 | 4 | 5 | 5 | 5 | 5 | 1 | 2 | 0 | 3 |
| 190 | 0.04 | 3 | 1 | 3 | 5 | 5 | 5 | 0 | 0 | 0 | 0 |
|  | 0.08 | 4 | 2 | 4 | 5 | 5 | 5 | 0 | 0 | 0 | 0 |
|  | 0.16 | 5 | 3 | 5 | 5 | 5 | 5 | 1 | 1 | 0 | 1 |
| 577 | 0.02 | 3 | 4 | 4 | 5 | 4 | 5 | 0 | 0 | 0 | 1 |
|  | 0.04 | 4 | 5 | 5 | 5 | 5 | 5 | 1 | 1 | 0 | 2 |
|  | 0.08 | 5 | 5 | 5 | 5 | 5 | 5 | 2 | 2 | 0 | 3 |
| 582 | 0.02 | 1 | 0 | 2 | 5 | 3 | 5 | 0 | 1 | 0 | 0 |
|  | 0.04 | 2 | 1 | 3 | 5 | 4 | 5 | 1 | 2 | 0 | 1 |
|  | 0.08 | 3 | 2 | 4 | 5 | 5 | 5 | 2 | 3 | 1 | 2 |
| 583 | 0.02 | 3 | 1 | 5 | 5 | 4 | 5 | 0 | 1 | 1 | 1 |
|  | 0.04 | 4 | 2 | 5 | 5 | 5 | 5 | 1 | 2 | 2 | 2 |
|  | 0.08 | 5 | 3 | 5 | 5 | 5 | 5 | 2 | 3 | 3 | 3 |
| 584 | 0.02 | 3 | 0 | 1 | 5 | 5 | 5 | 0 | 1 | 0 | 1 |
|  | 0.04 | 4 | 1 | 2 | 5 | 5 | 5 | 0 | 2 | 1 | 2 |
|  | 0.08 | 5 | 2 | 3 | 5 | 5 | 5 | 1 | 3 | 2 | 3 |
| 618 | 0.02 | 4 | 2 | 2 | 5 | 5 | 5 | 0 | 0 | 0 | 0 |
|  | 0.04 | 5 | 3 | 3 | 5 | 5 | 5 | 1 | 1 | 0 | 0 |
|  | 0.08 | 5 | 4 | 4 | 5 | 5 | 5 | 2 | 2 | 0 | 1 |
| 639 | 0.02 | 4 | 2 | 3 | 5 | 4 | 5 | 1 | 0 | 0 | 0 |
|  | 0.04 | 5 | 3 | 4 | 5 | 5 | 5 | 2 | 1 | 0 | 1 |
|  | 0.08 | 5 | 4 | 5 | 5 | 5 | 5 | 3 | 2 | 0 | 2 |
| 661 | 0.02 | 4 | 2 | 2 | 5 | 5 | 5 | 0 | 1 | 0 | 0 |
|  | 0.04 | 5 | 3 | 3 | 5 | 5 | 5 | 1 | 2 | 0 | 1 |
|  | 0.08 | 5 | 4 | 4 | 5 | 5 | 5 | 2 | 3 | 1 | 2 |
| 675 | 0.02 | 2 | 1 | 2 | 5 | 5 | 5 | 1 | 1 | 3 | 2 |
|  | 0.04 | 3 | 2 | 3 | 5 | 5 | 5 | 2 | 2 | 4 | 3 |
|  | 0.08 | 4 | 3 | 4 | 5 | 5 | 5 | 3 | 3 | 5 | 4 |
| 800 | 0.02 | 4 | 2 | 2 | 5 | 5 | 5 | 0 | 0 | 0 | 0 |
|  | 0.04 | 5 | 3 | 3 | 5 | 5 | 5 | 1 | 1 | 0 | 1 |
|  | 0.08 | 5 | 4 | 4 | 5 | 5 | 5 | 2 | 2 | 0 | 2 |
| 822 | 0.02 | 2 | 1 | 1 | 5 | 4 | 5 | 0 | 0 | 0 | 0 |
|  | 0.04 | 3 | 2 | 2 | 5 | 5 | 5 | 0 | 0 | 0 | 0 |
|  | 0.08 | 4 | 3 | 3 | 5 | 5 | 5 | 1 | 1 | 0 | 1 |

TABLE 8

| Compound No. | Amount (kg/ha) | (1) | (2) | (3) | (4) | (5) | (6) | (7) | (8) |
|---|---|---|---|---|---|---|---|---|---|
| 28 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 29 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 35 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 61 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 62 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 64 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 65 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 68 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 150 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 151 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 157 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 183 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 184 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 190 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 276 | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 308 | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 570 | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 612 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 613 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 618 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 1 |
| 620 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 1 |
| 639 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 1 |
| 640 | 0.005 | 5 | 5 | 5 | 5 | 5 | 5 | 5 | 0 |
|  | 0.01 | 5 | 5 | 5 | 5 | 5 | 5 | 5 | 0 |
|  | 0.02 | 5 | 5 | 5 | 5 | 5 | 5 | 5 | 1 |
| 644 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 1 |
| 686 | 0.01 | 4 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 1 |
| 731 | 0.02 | 4 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 767 | 0.01 | 4 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
| 773 | 0.01 | 4 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 774 | 0.01 | 4 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 779 | 0.01 | 4 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
|  | 0.08 | 5 | 5 | 5 | 5 | 5 | 5 | 5 | 0 |
| 781 | 0.01 | 4 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 0 |
| 800 | 0.01 | 5 | 5 | 5 | 5 | 5 | 5 | 5 | 0 |
|  | 0.02 | 5 | 5 | 5 | 5 | 5 | 5 | 5 | 0 |
|  | 0.04 | 5 | 5 | 5 | 5 | 5 | 5 | 5 | 1 |
| 805 | 0.01 | 4 | 5 | 5 | 5 | 5 | 5 | 5 | 0 |

TABLE 8-continued

| Compound No. | Amount (kg/ha) | (1) | (2) | (3) | (4) | (5) | (6) | (7) | (8) |
|---|---|---|---|---|---|---|---|---|---|
| | 0.02 | 5 | 5 | 5 | 5 | 5 | 5 | 5 | 0 |
| | 0.04 | 5 | 5 | 5 | 5 | 5 | 5 | 5 | 0 |
| 822 | 0.01 | 4 | 5 | 5 | 5 | 5 | 5 | 5 | 0 |
| | 0.02 | 5 | 5 | 5 | 5 | 5 | 5 | 5 | 0 |
| | 0.04 | 5 | 5 | 5 | 5 | 5 | 5 | 5 | 1 |
| 847 | 0.01 | 4 | 5 | 5 | 5 | 5 | 5 | 5 | 0 |
| | 0.02 | 5 | 5 | 5 | 5 | 5 | 5 | 5 | 0 |
| | 0.04 | 5 | 5 | 5 | 5 | 5 | 5 | 5 | 0 |
| Comparative compound B | 0.32 | 3 | 4 | 4 | 5 | 3 | 5 | 5 | 1 |
| | 0.63 | 5 | 5 | 5 | 5 | 4 | 5 | 5 | 2 |

What is claimed is:

1. A condensed heterocyclic derivative having the formula:

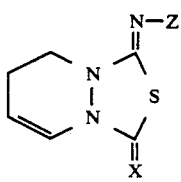
(I)

wherein X is an oxygen atom or a sulfur atom; and Z is

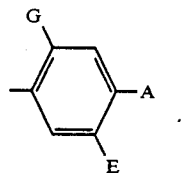

wherein G is a hydrogen atom or a halogen atom; A is a halogen atom or $NO_2$; E is a hydrogen atom, a halogen atom, $C\equiv N$, $NO_2$, $NH_2$, OH, SH, $OR_1$ (wherein $R_1$ is $C_1-C_5$ alkyl, $C_3-C_6$ cycloalkyl, $C_3-C_6$ cycloalkyl ($C_1-C_2$) alkyl, $C_2-C_4$ alkenyl, $C_3-C_4$ alkynyl,

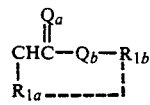

wherein each of Qa and Qb is an oxygen atom or a sulfur atom, $R_{1a}$ is a hydrogen atom or $C_1-C_3$ alkyl, $R_{1b}$ is a hydrogen atom, $C_1-C_5$ alkyl, $C_2-C_5$ alkenyl, $C_3-C_5$ alkynyl, $C_2-C_3$ haloalkyl, $C_1-C_2$ alkoxy ($C_1-C_2$) alkyl, $C_3-C_6$ cycloalkyl ($C_1-C_2$) alkyl, $C_3-C_6$ cycloalkyl, $CH_2CO_2$—($C_1-C_3$ alkyl) or $CH(CH_3)$—$CO_2$—($C_1-C_2$ alkyl), or $R_{1a}$ and $R_{1b}$ together form an alkylene group which in turn forms, together with

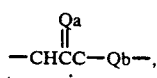

a 4-6 membered lactone ring,

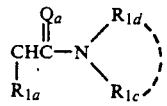

wherein $R_{1a}$ and Qa are as defined above, each of $R_{1c}$ an $R_{1d}$ is a hydrogen atom, $C_1-C_5$ alkyl, $C_2-C_5$ alkenyl, $C_3-C_5$ alkynyl, $C_2-C_5$ haloalkyl, $C_3-C_6$ cycloalkyl or $C_3-C_6$ cycloalkyl ($C_1-C_2$) alkyl, or $R_{1d}$ and $R_{1c}$ together form an alkylene group which in turn forms, together with the adjacent nitrogen atom, a 5-7 membered ring, $CH_2C\equiv N$, tetrahydropyranyl, tetrahydrothiopyranyl, $CH_2COR_{1e}$

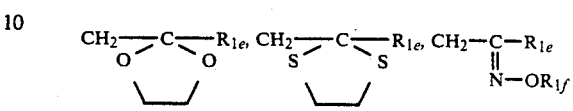

wherein $R_{1e}$ is $C_1-C_3$ alkyl, $R_{1f}$ is a hydrogen atom, $C_1-C_3$ alkyl, $CH_2CO_2$—($C_1-C_3$ alkyl) or $COCH_3$, or $C_1-C_2$ alkoxy ($C_1-C_2$ alkyl), $SR_3$ (wherein $R_3$ has the same meaning as $R_1$ defined above), $CO_2R_5$ (wherein $R_5$ is a hydrogen atom, $C_1-C_5$ alkyl, $C_3-C_6$ cycloalkyl, $C_3-C_6$ cycloalkyl ($C_1-C_2$) alkyl, $NHR_6$ (wherein $R_6$ is $C_1-C_5$ alkyl, $C_3-C_6$ cycloalkyl, $C_3-C_6$ cycloalkyl ($C_1-C_2$) alkyl, $C_2-C_4$ alkenyl or $C_3-C_4$ alkynyl), or $CH=NOR_7$ (wherein $R_7$ is a hydrogen atom, $C_1-C_5$ alkyl, $C_3-C_6$ cycloalkyl, $C_3-C_6$ cycloalkyl ($C_1-C_2$) alkyl, $C_2-C_4$ alkenyl or $C_3-C_4$ alkynyl).

2. The condensed heterocyclic derivative according to claim 1 having the formula:

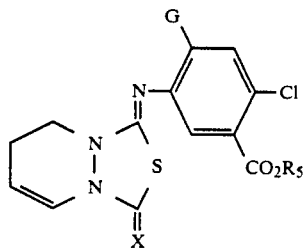

wherein X, G and $R_5$ are as defined in claim 1.

3. The condensed heterocyclic derivative according to claim 1, which is 9-(4-chloro-2-fluoro-5-ethoxycarbonylphenylimino)-8-thia-1,6-diazabicyclo[4.3.0]4-nonene-one.

4. The condensed heterocyclic derivative according to claim 1, which is 9-(4-chloro-2-fluoro-5-ethoxycarbonylphenylimino)-8-thia-1,6-diazabicyclo[4.3.0]4-nonene-7-thione.

5. The condensed heterocyclic derivative according to claim 1 having the formula:

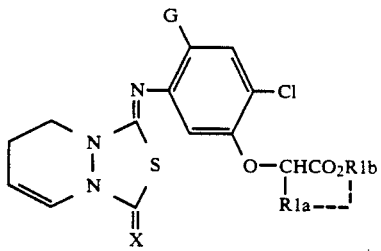

wherein X, G, R1a and R1b are as defined in claim 1.

6. The condensed heterocylic derivative according to claim 1, which is 9-[4-chloro-2-fluoro-5-(1-methoxycarbonylethoxy)phenylimino]-8-thia-1,6-diazabicyclo-[4.3.0]4-nonene-7-one.

7. The condensed heterocylic derivative according to claim 1, which is 9-[4-chloro-2-fluoro-5-(1-methoxycarbonylethoxy)phenylimino]-8-thia-1,6-diazabicyclo-[4.3.0]4-nonene-7-thione.

8. The condensed heterocyclic derivative according to claim 1 having the formula:

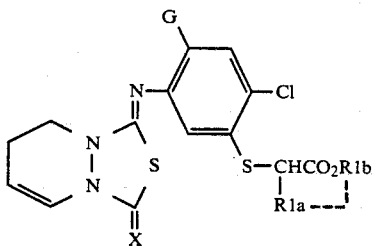

wherein X, G, R1a and R1b are defined in claim 1.

9. The condensed heterocyclic derivative according to claim 1, which is 9-(4-chloro-2-fluoro-5-methoxycarbonylmethylthiophenylimino)-8-thia-1,6-diazabicyclo[4.3.0]4-nonene-7-one.

10. The condensed heterocyclic derivative according to claim 1, which is 9-(4-chloro-2-fluoro-5-methoxycarbonylmethylthiophenylimino)-8-thia-1,6-diazabicyclo[4.3.0]4-nonene-7-thione.

11. The condensed heterocyclic derivative according to claim 1, which is 9-(4-chloro-2-fluoro-5-ethoxycarbonylmethylthiophenylimino)-8-thia-1,6-diazabicyclo[4.3.0]4-nonene-7-one.

12. The condensed heterocyclic derivative according to claim 1, which is 9-(4-chloro-2-fluoro-5-ethoxycarbonylmethylthiophenylimino)-8-thia-1,6-diazabicyclo[4.3.0]4-nonene-7-thione.

13. The condensed heterocyclic derivative according to claim 1, which is 9-(4-chloro-2-fluoro-5-cyclopentyloxycarbonylmethylthiophenylimino)-8-thia-1,6-diazabicyclo[4.3.0]4-nonene-7-one.

14. The condensed heterocyclic derivative according to claim 1, which is 9-(4-chloro-2-fluoro-5-cyclopentyloxycarbonylmethylthiophenylimino)-8-thia-1,6-diazabicyclo-[4.3.0]4-nonene-7-thione.

15. The condensed heterocyclic derivative according to claim 1, which is 9-(4-chloro-3-methoxycarbonylmethylthiophenylimino)-8-thia-1,6-diazabicyclo[4.3.0]4-nonene-7-one.

16. The condensed heterocyclic derivative according to claim 1, which is 9-(4-chloro-3-methoxycarbonylmethylthiophenylimino)-8-thia-1,6-diazabicyclo-[4.3.0]4-nonene-7-thione.

17. The condensed heterocyclic derivative according to claim 1 having the formula:

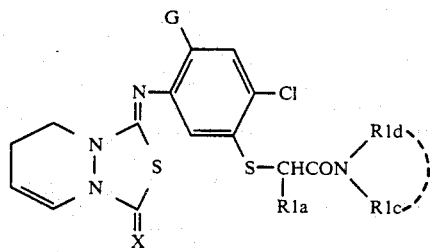

wherein X, G, R1a, R1c and R1d are as defined in claim 1.

18. A herbicide comprising a herbicidally effective amount of a condensed heterocyclic derivative of the formula I as defined in claim 1 and an agricultural carrier or diluent.

19. A method for controlling weeds, which comprises applying a herbicidally effective amount of a condensed heterocyclic derivative of the formula I as defined in claim 1 to a locus to be protected.

* * * * *